US011193128B2

(12) United States Patent
Rigo

(10) Patent No.: US 11,193,128 B2
(45) Date of Patent: Dec. 7, 2021

(54) COMPOSITIONS FOR MODULATING EXPRESSION OF C9ORF72 ANTISENSE TRANSCRIPT

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/554,115

(22) Filed: Aug. 28, 2019

(65) Prior Publication Data

US 2020/0239883 A1 Jul. 30, 2020

Related U.S. Application Data

(60) Division of application No. 15/848,389, filed on Dec. 20, 2017, which is a continuation-in-part of application No. 15/029,210, filed as application No. PCT/US2014/060530 on Oct. 14, 2014, now abandoned, and a continuation-in-part of application No. 15/029,039, filed as application No. PCT/US2014/060512 on Oct. 14, 2014, now abandoned.

(60) Provisional application No. 61/890,852, filed on Oct. 14, 2013, provisional application No. 61/890,849, filed on Oct. 14, 2013.

(51) Int. Cl.
*C12N 15/113* (2010.01)
*A61P 21/00* (2006.01)
*A61P 25/28* (2006.01)

(52) U.S. Cl.
CPC ............ *C12N 15/113* (2013.01); *A61P 21/00* (2018.01); *A61P 25/28* (2018.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3233* (2013.01); *C12N 2310/3341* (2013.01); *C12N 2310/341* (2013.01); *C12N 2310/351* (2013.01); *C12N 2320/32* (2013.01)

(58) Field of Classification Search
CPC ............ C12N 15/113; C12N 2310/322; C12N 2310/315; C12N 2310/11; C12N 2310/3341; C12N 2310/3231; A61P 21/00; A61P 25/28
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,188,897 A | 2/1993 | Suhadolnik et al. |
| 5,194,599 A | 3/1993 | Froehler |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |

(Continued)

FOREIGN PATENT DOCUMENTS

| | | |
|---|---|---|
| WO | WO 2002/062954 | 8/2002 |
| WO | WO 2005/063976 | 7/2005 |

(Continued)

OTHER PUBLICATIONS

Ash et al., "Unconventional translation of C9ORF72 GGGGCC expansion generates insoluble polypeptides specific to c9FTD/ASL." Neuron (2013) 77(4):639-646.

(Continued)

*Primary Examiner* — Richard A Schnizer

(74) *Attorney, Agent, or Firm* — McNeill Baur

(57) ABSTRACT

Disclosed herein are compositions and methods for reducing expression of C9ORF72 antisense transcript in an animal with C9ORF72 antisense transcript specific inhibitors. Such methods are useful to treat, prevent, or ameliorate neurodegenerative diseases in an individual in need thereof. Such C9ORF72 antisense transcript specific inhibitors include antisense compounds.

44 Claims, No Drawings

Specification includes a Sequence Listing.

(56) References Cited

U.S. PATENT DOCUMENTS

| | | |
|---|---|---|
| 5,185,444 A | 12/1993 | Summerton et al. |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddty et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'O |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,372,492 B1 | 4/2002 | Bennett et al. |
| 6,426,220 B1 | 7/2002 | Bennett et al. |
| 6,455,308 B1 * | 9/2002 | Freier .................. C12N 15/113 435/325 |
| 6,525,191 B1 | 2/2003 | Ramasamy |
| 6,531,584 B1 | 3/2003 | Cook et al. |
| 6,600,032 B1 | 7/2003 | Manoharan et al. |
| 6,660,720 B2 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,833,361 B2 | 12/2004 | Hong et al. |
| 6,906,182 B2 | 6/2005 | Ts'o et al. |
| 7,015,315 B1 | 3/2006 | Cook et al. |
| 7,034,133 B2 | 4/2006 | Wengel et al. |
| 7,053,207 B2 | 5/2006 | Wengel et al. |
| 7,101,993 B1 | 9/2006 | Cook et al. |
| 7,262,177 B2 | 8/2007 | Ts'o et al. |
| 7,399,845 B2 | 7/2008 | Seth et al. |
| 7,427,672 B2 | 9/2008 | Imanishi et al. |
| 7,491,805 B2 | 2/2009 | Vargeese et al. |
| 7,547,684 B2 | 6/2009 | Seth et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,106,022 B2 | 1/2012 | Manoharan et al. |
| 8,124,745 B2 | 2/2012 | Allerson et al. |
| 8,153,365 B2 | 4/2012 | Wengel et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,410,070 B2 | 4/2013 | Miller et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |

(56) References Cited

U.S. PATENT DOCUMENTS

| | | | |
|---|---|---|---|
| 10,174,323 B2 | 1/2019 | Krieg et al. | |
| 10,407,678 B2 | 9/2019 | Rigo | |
| 2003/0082807 A1 | 5/2003 | Wengel | |
| 2003/0158403 A1 | 8/2003 | Manoharan et al. | |
| 2003/0175906 A1 | 9/2003 | Manoharan et al. | |
| 2003/0207841 A1 | 11/2003 | Kaneko et al. | |
| 2003/0224377 A1 | 12/2003 | Wengel et al. | |
| 2004/0023917 A1* | 2/2004 | Bennett | C07H 21/00 514/44 A |
| 2004/0143114 A1 | 7/2004 | Imanishi et al. | |
| 2004/0171570 A1 | 9/2004 | Allerson et al. | |
| 2004/0192918 A1 | 9/2004 | Imanishi et al. | |
| 2004/0241651 A1* | 12/2004 | Olek | C12Q 1/6883 435/6.16 |
| 2004/0265230 A1 | 12/2004 | Martinez et al. | |
| 2005/0130923 A1 | 6/2005 | Bhat et al. | |
| 2005/0255487 A1 | 11/2005 | Khvorova et al. | |
| 2006/0148740 A1 | 7/2006 | Platenburg | |
| 2006/0286575 A1* | 12/2006 | Farrell | C12Q 1/6886 435/6.14 |
| 2008/0039618 A1 | 2/2008 | Allerson et al. | |
| 2010/0190837 A1 | 7/2010 | Migawa et al. | |
| 2010/0197762 A1 | 8/2010 | Swayze et al. | |
| 2011/0097716 A1* | 4/2011 | Natt | C12Q 1/6851 435/6.11 |
| 2011/0123520 A1 | 5/2011 | Manoharan et al. | |
| 2011/0213019 A1* | 9/2011 | Miller | A61K 31/7088 514/44 R |
| 2011/0294870 A1 | 12/2011 | Collard et al. | |
| 2013/0130378 A1 | 5/2013 | Manoharan et al. | |
| 2013/0203836 A1 | 8/2013 | Rajeev et al. | |
| 2014/0107330 A1 | 4/2014 | Freier et al. | |
| 2014/0303238 A1 | 10/2014 | Linsley | |
| 2015/0018540 A1 | 1/2015 | Prakash et al. | |
| 2015/0141320 A1 | 5/2015 | Krieg et al. | |
| 2015/0159160 A1* | 6/2015 | Krieg | A61P 43/00 514/44 A |
| 2015/0184153 A1 | 7/2015 | Freier et al. | |
| 2015/0191727 A1 | 7/2015 | Migawa et al. | |
| 2015/0267195 A1 | 9/2015 | Seth et al. | |
| 2015/0267197 A1 | 9/2015 | Bennett et al. | |
| 2015/0275212 A1 | 10/2015 | Albaek et al. | |
| 2016/0025747 A1 | 1/2016 | Ranum et al. | |
| 2016/0108396 A1 | 4/2016 | Jensen et al. | |
| 2016/0230172 A1 | 8/2016 | Rigo | |
| 2016/0237432 A1 | 8/2016 | Bennett et al. | |
| 2018/0016575 A1 | 1/2018 | Hansen et al. | |
| 2018/0023077 A1 | 1/2018 | Rigo | |
| 2018/0119142 A1 | 5/2018 | Rigo | |
| 2018/0142240 A1 | 5/2018 | Bennett et al. | |

FOREIGN PATENT DOCUMENTS

| | | | |
|---|---|---|---|
| WO | WO 2007/056113 | 5/2007 | |
| WO | WO 2012/012467 | 1/2012 | |
| WO | WO 2012/114111 | 8/2012 | |
| WO | WO-2013036833 A1 * | 3/2013 | C12Q 1/6883 |
| WO | WO-2013041577 A1 * | 3/2013 | C12Q 1/6883 |
| WO | WO 2013/082548 | 6/2013 | |
| WO | WO 2014/062691 | 4/2014 | |
| WO | WO 2015/057727 | 4/2015 | |
| WO | WO 2015/057738 | 4/2015 | |
| WO | WO 2016/112132 | 7/2016 | |
| WO | WO 2016/167780 | 10/2016 | |

OTHER PUBLICATIONS

Baughn et al., "Sense and Anti-Sense RNA Foci in c9ALS/FTD: More Light in a House of Mirrors" Annals of Neurology (Oct. 14, 2013) 74(17): pS60.

Blitterswijk et al., "How do C9ORF72 repeat expansions cause amyotrophic lateral sclerosis and frontotemporal dementia: can we learn from other noncoding repeat expansion disorders?" Curr Opin Neurol. (2012) 25(6):689-700.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Ciura et al., "Loss of function of C9orf72 causes motor deficits in a zebrafish model of Amyotrophic Lateral Sclerosis" Annals of Neurology (2013).

Cleveland, D.W., "Gene silencing therapy for human neurodegenerative disease" Oral Presentation, 10th Brain Research Conference, Chicago, IL, Oct. 15, 2015.

Crooke, ST., et al., "Antisense Drug Technology" Second Edition, CRC Press (2008) Chapters 1-28,.

Dejesus-Hernandez et al., "Expanded GGGGCC Hexanucleotide Repeat in Noncoding Region of C9QRF72 Causes Chromosome 9p-Linked FTD and ALS" Neuron (2011) 72:245-256,.

Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.

Extended European Search Report for Application No. 14854291.3 dated Apr. 24, 2017.

Extended European Search Report for Application No. 14854442.2 dated May 17, 2017.

Gautschi et al., "Activity of a novel bcl-2/bcl-xLbispecific antisense oligonucleotide against tumors of diverse histologic origins" J. Natl. Cancer Inst. (2001) 93:463-471.

Gendron et al., "Antisense transcripts of the expanded C9ORF72 hexanucleotide repeat form nuclear RNA foci and undergo repeat-associated non-ATG translation in c9FTD/ALS." Acta Nuropathol (2013) 126(6):829-844.

Gendron et al., "c9RAN Translation: a potential therapeutic target for the treatment of amyotrophic lateral sclerosis and frontotemporal dementia." Expert Opin. Ther. Targets (2013) 17(9):991-995.

Gendron et al., "Disease Mechanisms of C9ORF72 Repeat Expansions" Cold Spring Harbor Perspect Med (Jan. 27, 2017) doi: 10.1101/schperspec.a024224.

Hirtz et al., "How common are the "common" neurologic disorders?" Neurology (2007) 68:326-337.

International Search Report for application No. PCT/US2014/060512 dated Jan. 21, 2015.

International Search Report for application No. PCT/US2014/060530 dated Jan. 21, 2015.

International Search Report for application No. PCT/US2015/026218 dated Oct. 23, 2015.

International Search Report for application No. PCT/US2016/012381 dated May 17, 2016.

Jiang et al. "Gain of Toxicity from ALS/FTG-Linked Repeat Expansions in C9ORF72 Is Alleviated by Antisense Oligonucleotides Targeting GGGCC-Containing RNAs." Neuron (2016) 90:535-550.

Jiang et al., "Bidirectional Transcriptional Inhibition as Therapy for ALS/FTD Caused by Repeat Expansion in C9orf72" Neuron (2016) 92:1160-1163.

Johnson et al., "Exome sequencing reveals VCP mutations as a cause of familial ALS" Neuron (2010) 68:857-864.

Kwiatkowski et al., "Mutations in the FUS/TLS gene on chromosome 16 cause familial amyotrophic lateral sclerosis" Science (2009) 323:1205-1208.

Laaksovirta et al., "Chromosome 9p21 in amyotrophic lateral sclerosis in Finland: a genome-wide association study" Lancet Neurol, (2010) 9:978-985.

Lagier-Tourenne C, et al. "Targeted degradation of sense and antisense C9orf72 RNA foci as therapy for ALS and frontotemporal degeneration" PNAS (2013) 110(47):E4530-E4539.

Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.

(56) References Cited

OTHER PUBLICATIONS

Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.
Lillo et al., "Frontotemporal dementia and motor neurone disease: overlapping clinic-pathological disorders" J. Clin. Neurosci. (2009) 16:1131-1135.
Maher et al., "Comparative hybrid arrest by tandem antisense oligodeoxy ribonucleotides or oligodeoxyribonucleoside methylpbosphonates in a cell-free system" Nucl. Acid. Res. (1998) 16(8):3341-3358.
Maruyama et al., "Mutations of optineurin in amyotrophic lateral sclerosis" Nature (2010) 465:223-226.
Mori et al., "The C9orf72 GGGGCC repeat is translated into aggregating dipeptide-repeat proteins in FTLD/ALS." Science (2013) 339:1335-1338.
Mori et al., Supplemental Material for "The C9orf72 GGGGCC repeat is translated into aggregating dipeptide-repeat proteins in FTLD/ALS." Science (2013) 339:1335-1338.
Morita et al., "A locus on chromosome 9p confers susceptibility to ALS and frontotemporal dementia" Neurology (2006) 66:839-844.
Mulders et al. "Triplet-repeat oligonucleotide-mediated reversal of RNA toxicity in myotonic dystrophy." Proc. Nat. Acad. Sci. USA (2009) 106(33):13915-13920.
NCBI Reference AC255463 *Homo sapiens* crhromosome 9 clone 174779_ABC12_000049116500_D6. (Jul. 16, 2014) [Retreived from the internet Aug. 17, 2016: <http://www.ncbi.nlm.nih.gov/nuccore/AC255463.1>].
Neumann et al., "Ubiquitinated TDP-43 in frontotemporal lobar degeneration and amyotrophic lateral sclerosis" Science (2006) 314:130-133.
Pearson et al., "Familial frontotemporal dementia with amyotrophic lateral sclerosis and a shared haplotype on chromosome 9p" J. Nerol. (2011) 258:647-655.
Picher-Martel et al., "From Animal Models to Human Disease: A Genetic Approach for Personalized Medicine in ALS" Acta Neuropathologica Communications (2016) 4(70): 1-29.
Renton et al., "A hexanucleotide repeat expansion in C9orf72 is the cause of chromosome 9p21-linked ASL-FTD," Neuron (2011) 72(2):257-268.
Riboldi et al., "Antisense oligonucleotide therapy for the treatment of C9ORF72 ALS/FTD diseases." Mol Nuerobiol (2014) 50(3):721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22): 1688-1700.
Sareen et al., "Targeting RNA foci in iPSC-derived motor neurons from ALS patients with a C9ORF72 repeat expansion," Sci Tran Med (2013) 5(208): 1-13.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Sha et al., "Treatment implications of C9ORF72" Alzheimers Res Ther (2012) 4(6): 46.
Sreedharan et al., "TDP-43 mutations in familial and sporadic amyotrophic lateral sclerosis" Science (2008) 319:1668-1672.
Todd et al., "RNA-Mediated Neurodegeneration in Repeat Expansion Disorders." Annals of Neurology (2010) 67:291-300.
Vance et al., "Familial amyotrophic lateral sclerosis with frontotemporal dementia is linked to a locus on chromosome 9p13.2-21.3" Brain (2006) 129:868-876.
Woolf et al., "Specificity of antisense oligonucleotides in vivo" PNAS (1992) 89: 7305-7309.
Xu et al., "Expanded GGGGCC repeat RNA associated with amyotrophic lateral sclerosis and frontotemporal dementia causes neurodegeneration" Proceedings National Academy of Sciences PNAS (2013) 110(19): 7778-7783.
Zu et al., "RNA proteins and RNA foci from antisense transcripts in C9ORF72 ALS and frontotemporal dementia" PNAS (2013) E4968-E4977.

* cited by examiner

SEQUENCE LISTING

<160> NUMBER OF SEQ ID NOS: 94

<210> SEQ ID NO 1
<211> LENGTH: 3339
<212> TYPE: DNA
<213> ORGANISM: Homo sapiens

<400> SEQUENCE: 1
acgtaaccta cggtgtcccg ctaggaaaga gaggtgcgtc aaacagcgac aagttccgcc    60

```
cacgtaaaag atgacgcttg gtgtgtcagc cgtccctgct gcccggttgc ttctcttttg    120
ggggcgggt  ctagcaagag caggtgtggg tttaggagat atctccggag catttggata    180
atgtgacagt tggaatgcag tgatgtcgac tctttgccca ccgccatctc cagctgttgc    240
caagacagag attgctttaa gtggcaaatc acctttatta gcagctactt ttgcttactg    300
ggacaatatt cttggtccta gagtaaggca catttgggct ccaaagacag aacaggtact    360
tctcagtgat ggagaaataa cttttcttgc caaccacact ctaaatggag aaatccttcg    420
aaatgcagag agtggtgcta tagatgtaaa gttttttgtc ttgtctgaaa agggagtgat    480
tattgtttca ttaatctttg atggaaactg gaatggggat cgcagcacat atggactatc    540
aattatactt ccacagacag aacttagttt ctacctccca cttcatagag tgtgtgttga    600
tagattaaca catataatcc ggaaaggaag aatatggatg cataaggaaa gacaagaaaa    660
tgtccagaag attatcttag aaggcacaga gagaatggaa gatcagggtc agagtattat    720
tccaatgctt actggagaag tgattcctgt aatggaactg ctttcatcta tgaaatcaca    780
cagtgttcct gaagaaatag atatagctga tacagtactc aatgatgatg atattggtga    840
cagctgtcat gaaggctttc ttctcaatgc catcagctca cacttgcaaa cctgtggctg    900
ttccgttgta gtaggtagca gtgcagagaa agtaaataag atagtcagaa cattatgcct    960
ttttctgact ccagcagaga gaaaatgctc caggttatgt gaagcagaat catcatttaa    1020
atatgagtca gggctctttg tacaaggcct gctaaaggat tcaactggaa gctttgtgct    1080
gcctttccgg caagtcatgt atgctccata tcccaccaca cacatagatg tggatgtcaa    1140
tactgtgaag cagatgccac cctgtcatga acatatttat aatcagcgta gatacatgag    1200
atccgagctg acagccttct ggagagccac ttcagaagaa gacatggctc aggatacgat    1260
catctacact gacgaaagct ttactcctga tttgaatatt tttcaagatg tcttacacag    1320
agacactcta gtgaaagcct tcctggatca ggtctttcag ctgaaacctg gcttatctct    1380
cagaagtact ttccttgcac agtttctact tgtccttcac agaaaagcct tgacactaat    1440
aaaatatata gaagacgata cgcagaaggg aaaaaagccc tttaaatctc ttcggaacct    1500
gaagatagac cttgatttaa cagcagaggg cgatcttaac ataataatgg ctctggctga    1560
gaaaattaaa ccaggcctac actcttttat ctttggaaga cctttctaca ctagtgtgca    1620
agaacgagat gttctaatga cttttttaaat gtgtaactta ataagcctat tccatcacaa    1680
tcatgatcgc tggtaaagta gctcagtggt gtggggaaac gttccctgg  atcatactcc    1740
agaattctgc tctcagcaat tgcagttaag taagttacac tacagttctc acaagagcct    1800
gtgaggggat gtcaggtgca tcattacatt gggtgtctct tttcctagat ttatgctttt    1860
gggatacaga cctatgttta caatataata aatattattg ctatcttta  aagatataat    1920
aataggatgt aaacttgacc acaactactg ttttttgaa  atacatgatt catggtttac    1980
atgtgtcaag gtgaaatctg agttggcttt tacagatagt tgactttcta tcttttggca    2040
ttctttggtg tgtagaatta ctgtaatact tctgcaatca actgaaaact agagcctttta   2100
aatgatttca attccacaga agaaagtgaa gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa    2280
ccacagttag ggtgttttgt ttattttatt gttcttgcta ttgttgatat tctatgtagt    2340
tgagctctgt aaaaggaaat tgtatttttat gtttagtaa ttgttgccaa ctttttaaat    2400
taattttcat tattttgag  ccaaattgaa atgtgcacct cctgtgcctt ttttctcctt    2460
```

```
agaaaatcta attacttgga acaagttcag atttcactgg tcagtcattt tcatcttgtt    2520
ttcttcttgc taagtcttac catgtacctg ctttggcaat cattgcaact ctgagattat    2580
aaaatgcctt agagaatata ctaactaata agatcttttt ttcagaaaca gaaaatagtt    2640
ccttgagtac ttccttcttg catttctgcc tatgttttg aagttgttgc tgtttgcctg     2700
caataggcta taaggaatag caggagaaat tttactgaag tgctgttttc ctaggtgcta    2760
ctttggcaga gctaagttat cttttgtttt cttaatgcgt ttggaccatt ttgctggcta    2820
taaaataact gattaatata attctaacac aatgttgaca ttgtagttac acaaacacaa    2880
ataaatattt tatttaaaat tctggaagta atataaaagg gaaatatat ttataagaaa     2940 gggataaagg taatagagcc cttctgcccc ccacccacca aatttacaca acaaaatgac    3000
atgttcgaat gtgaaaggtc ataatagctt tcccatcatg aatcagaaag atgtggacag    3060
cttgatgttt tagacaacca ctgaactaga tgactgttgt actgtagctc agtcatttaa    3120
aaaatatata aatactacct tgtagtgtcc catactgtgt tttttacatg gtagattctt    3180
atttaagtgc taactggtta ttttctttgg ctggtttatt gtactgttat acagaatgta    3240
agttgtacag tgaaataagt tattaaagca tgtgtaaaca ttgttatata tcttttctcc    3300
taaatggaga attttgaata aaatatattt gaaattttg                           3339
```

<210> SEQ ID NO 2
<211> LENGTH: 30001
<212> TYPE: DNA
<213> ORGANISM: Homo sapiens

<400> SEQUENCE: 2

```
caaagaaaag ggggaggttt tgttaaaaaa gagaaatgtt acatagtgct ctttgagaaa      60
attcattggc actattaagg atctgaggag ctggtgagtt tcaactggtg agtgatggtg     120
gtagataaaa ttagagctgc agcaggtcat tttagcaact attagataaa actggtctca     180
ggtcacaacg ggcagttgca gcagctggac ttggagagaa ttacactgtg ggagcagtgt     240
catttgtcct aagtgctttt ctaccccta cccccactat tttagttggg tataaaaaga     300
atgacccaat ttgtatgatc aactttcaca aagcatagaa cagtaggaaa agggtctgtt     360
tctgcagaag gtgtagacgt tgagagccat tttgtgtatt tattcctccc tttcttcctc     420
ggtgaatgat taaaacgttc tgtgtgattt ttagtgatga aaaagattaa atgctactca     480
ctgtagtaag tgccatctca cacttgcaga tcaaaaggca cacagtttaa aaaacctttg    540
tttttttaca catctgagtg gtgtaaatgc tactcatctg tagtaagtgg aatctataca    600
cctgcagacc aaaagacgca aggtttcaaa aatctttgtg ttttttacac atcaaacaga    660
atggtacgtt tttcaaaagt taaaaaaaaa caactcatcc acatattgca actagcaaaa    720
atgacattcc ccagtgtgaa aatcatgctt gagagaattc ttacatgtaa aggcaaaatt    780
gcgatgactt tgcaggggac cgtgggattc ccgcccgcag tgccggagct gtcccctacc    840
agggtttgca gtggagtttt gaatgcactt aacagtgtct tacggtaaaa acaaaatttc    900
atccaccaat tatgtgttga gcgcccactg cctaccaagc acaaacaaaa ccatcaaaaa    960
ccacgaaatc gtcttcactt tctccagatc cagcagcctc ccctattaag gttcgcacac   1020
gctattgcgc caacgctcct ccagagcggg tcttaagata aagaacagg acaagttgcc     1080 ccgcccatt tcgctagcct cgtgagaaaa cgtcatcgca catagaaaac agacagacgt     1140
aacctacggt gtcccgctag gaaagagagg tgcgtcaaac agcgacaagt tccgcccacg   1200
```

```
taaaagatga cgcttggtgt gtcagccgtc cctgctgccc ggttgcttct cttttggggg    1260
cggggtctag caagagcagg tgtgggttta ggaggtgtgt gtttttgttt ttcccaccct    1320
ctctccccac tacttgctct cacagtactc gctgagggtg aacaagaaaa gacctgataa    1380
agattaacca gaagaaaaca aggagggaaa caaccgcagc ctgtagcaag ctctggaact    1440
caggagtcgc gcgctagggg ccggggccgg ggccggggcg tggtcggggc gggcccgggg    1500
gcgggcccgg ggcggggctg cggttgcggt gcctgcgccc gcggcggcgg aggcgcaggc    1560
ggtggcgagt gggtgagtga ggaggcggca tcctggcggg tggctgtttg gggttcggct    1620
gccgggaaga ggcgcgggta gaagcggggg ctctcctcag agctcgacgc attttttactt    1680
tccctctcat ttctctgacc gaagctgggt gtcgggcttt cgcctctagc gactggtgga    1740
attgcctgca tccgggcccc gggcttcccg gcggcggcgg cggcggcggc ggcgcaggga    1800
caagggatgg ggatctggcc tcttccttgc tttcccgccc tcagtacccg agctgtctcc    1860
ttcccgggga cccgctggga gcgctgccgc tgcgggctcg agaaaaggga gcctcgggta    1920
ctgagaggcc tcgcctgggg gaaggccgga gggtgggcgg cgcgcggctt ctgcggacca    1980
agtcggggtt cgctaggaac ccgagacggt ccctgccggc gaggagatca tgcgggatga    2040
gatggggtg tggagacgcc tgcacaattt cagcccaagc ttctagagag tggtgatgac    2100
ttgcatatga gggcagcaat gcaagtcggt gtgctcccca ttctgtggga catgacctgg    2160
ttgcttcaca gctccgagat gacacagact tgcttaaagg aagtgactat tgtgacttgg    2220
gcatcacttg actgatggta atcagttgtc taaagaagtg cacagattac atgtccgtgt    2280
gctcattggg tctatctggc cgcgttgaac accaccaggc tttgtattca gaaacaggag    2340
ggaggtcctg cactttccca ggaggggtgg cccttttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaag atactgttaa gatatgattt ttctcagact ttgggaaact    2580
tttaacataa tctgtgaata tcacagaaac aagactatca tatagggggat attaataacc    2640
tggagtcaga atacttgaaa tacggtgtca tttgacacgg gcattgttgt caccacctct    2700
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
ttttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctcttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttggagggct gaggcaggag ggtcatttga gcccaagagt ttgaagttac cgagagctat    3480
gatcctgcca gtgcattcca gcctggatga caaaacgaga ccctgtctct aaaaaacaag    3540
aagtgagggc tttatgattg tagaatttc actacaatag cagtggacca accacctttc    3600
```

```
taaataccaa tcagggaaga gatggttgat tttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatcttgg cttccctcaa aagactggct aatgtttggt    3840
aactctctgg agtagacagc actacatgta cgtaagatag gtacataaac aactattggt    3900
tttgagctga ttttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tcttttttgtt tgtttgtttg tttgttttttt tcttgaggca    4140 gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg ctaattttt tgtattttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc atttttttttt tcttattctg    4440 ttaggagtga gagtgtaact agcagtataa tagttcaatt ttcacaacgt ggtaaaagtt    4500
tccctataat tcaatcagat tttgctccag ggttcagttc tgttttagga aatacttttta    4560 ttttcagttt aatgatgaaa tattagagtt gtaatattgc ctttatgatt atccaccttt    4620
ttaacctaaa agaatgaaag aaaaatatgt ttgcaatata atttttatggt tgtatgttaa    4680 cttaattcat tatgttggcc tccagtttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttttgaa    4920 attacaaata cacgtgttaa aactgtcgtt gtgttcaacc atttctgtac atacttagag    4980
ttaactgttt tgccaggctc tgtatgccta ctcataatat gataaaagca ctcatctaat    5040
gctctgtaaa tagaagtcag tgcttttccat cagactgaac tctcttgaca agatgtggat    5100
gaaattcttt aagtaaaatt gtttactttg tcatacatttt acagatcaaa tgttagctcc    5160
caaagcaatc atatggcaaa gataggtata tcatagtttg cctattagct gctttgtatt    5220
gctattatta taaatagact tcacagtttt agacttgctt aggtgaaatt gcaattcttt    5280
ttactttcag tcttagataa caagtcttca attatagtac aatcacacat tgcttaggaa    5340
tgcatcatta ggcgattttg tcattatgca aacatcatag agtgtactta cacaaaccta    5400
gatagtatag cctttatgta cctaggccgt atggtatagt ctgttgctcc taggccacaa    5460
acctgtacaa ctgttactgt actgaatact atagacagtt gtaacacagt ggtaaatatt    5520
tatctaaata tatgcaaaca gagaaaaggt acagtaaaag tatggtataa aagataatgg    5580
tatacctgtg taggccactt accacgaatg gagcttgcag gactagaagt tgctctgggt    5640
gagtcagtga gtgagtggtg aattaatgtg aaggcctaga acactgtaca ccactgtaga    5700
ctataaacac agtacgctga agctacacca aatttatctt aacagttttt cttcaataaa    5760
aaattataac tttttaactt tgtaaacttt ttaattttttt aacttttaaa atacttagct    5820
tgaaacacaa atacattgta tagctataca aaaatatttt ttctttgtat ccttattcta    5880
gaagcttttt tctatttttct attttaaatt tttttttttta cttgttagtc gttttttgtta    5940
```

```
aaaactaaaa cacacacact ttcacctagg catagacagg attaggatca tcagtatcac    6000
tcccttccac ctcactgcct tccacctcca catcttgtcc cactggaagg tttttagggg    6060
caataacaca catgtagctg tcacctatga taacagtgct ttctgttgaa tacctcctga    6120
aggacttgcc tgaggctgtt ttacatttaa cttaaaaaaa aaaaagtag aaggagtgca     6180 ctctaaaata acaataaaag gcatagtata gtgaatacat aaaccagcaa tgtagtagtt    6240
tattatcaag tgttgtacac tgtaataatt gtatgtgcta tactttaaat aacttgcaaa    6300
atagtactaa gaccttatga tggttacagt gtcactaagg caatagcata ttttcaggtc    6360
cattgtaatc taatgggact accatcatat atgcagtcta ccattgactg aaacgttaca    6420
tggcacataa ctgtatttgc aagaatgatt tgttttacat taatatcaca taggatgtac    6480 cttttagag tggtatgttt atgtggatta agatgtacaa gttgagcaag ggaccaaga     6540 gccctgggtt ctgtcttgga tgtgagcgtt tatgttcttc tcctcatgtc tgttttctca    6600
ttaaattcaa aggcttgaac gggcccctatt tagcccttct gttttctacg tgttctaaat   6660
aactaaagct tttaaattct agccatttag tgtagaactc tctttgcagt gatgaaatgc    6720
tgtattggtt tcttggctag catattaaat attttatct tgtcttgat acttcaatgt     6780 cgttttaaac atcaggatcg ggcttcagta ttctcataac cagagagttc actgaggata    6840
caggactgtt tgcccatttt ttgttatggc tccagacttg tggtatttcc atgtcttttt    6900
tttttttttt ttttttgacc tttagcggc tttaaagtat ttctgttgtt aggtgttgta    6960
ttacttttct aagattactt aacaaagcac cacaaactga gtggctttaa caacagcaa    7020 tttattctct cacaattcta gaagctagaa gtccgaaatc aaagtgttga caggggcatg    7080
atcttcaaga gagaagactc tttccttgcc tcttcctggc ttctggtggt taccagcaat    7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgacccattt taacatgat tacacttatt     7320 tctagataag gtcacattca cgtacaccaa gggttaggaa ttgaacatat ctttttgggg    7380
gacacaattc aacccacaag tgtcagtctc tagctgagcc tttcccttcc tgttttctc    7440 ctttttagtt gctatgggtt aggggccaaa tctccagtca tactagaatt gcacatggac    7500
tggatatttg ggaatactgc gggtctattc tatgagcttt agtatgtaac atttaatatc    7560
agtgtaaaga agccctttttt taagttattt ctttgaattt ctaaatgtat gccctgaata   7620
taagtaacaa gttaccatgt cttgtaaaat gatcatatca acaaacattt aatgtgcacc    7680
tactgtgcta gttgaatgtc tttatcctga taggagataa caggattcca catctttgac    7740
ttaagaggac aaaccaaata tgtctaaatc atttggggtt ttgatggata tctttaaatt    7800
gctgaaccta atcattggtt tcatatgtca ttgtttagat atctccggag catttggata    7860
atgtgacagt tggaatgcag tgatgtcgac tctttgccca ccgccatctc cagctgttgc    7920
caagacagag attgctttaa gtggcaaatc acctttatta gcagctactt ttgcttactg    7980
ggacaatatt cttggtccta gagtaaggca catttgggct ccaaagacag aacaggtact    8040
tctcagtgat ggagaaataa cttttcttgc caaccacact ctaaatggag aaatccttcg    8100
aaatgcagag agtggtgcta tagatgtaaa gttttttgtc ttgtctgaaa agggagtgat    8160
tattgtttca ttaatctttg atggaaactg gaatggggat cgcagcacat atggactatc    8220
aattatactt ccacagacag aacttagttt ctacctccca cttcatagag tgtgtgttga    8280
tagattaaca catataatcc ggaaaggaag aatatggatg cataaggtaa gtgattttc    8340
```

```
agcttattaa tcatgttaac ctatctgttg aaagcttatt ttctggtaca tataaatctt    8400
atttttttaa ttatatgcag tgaacatcaa acaataaatg ttatttattt tgcatttacc    8460
ctattagata caaatacatc tggtctgata cctgtcatct tcatattaac tgtggaaggt    8520
acgaaatggt agctccacat tatagatgaa aagctaaagc ttagacaaat aaagaaactt    8580
ttagaccctg gattcttctt gggagccttt gactctaata cctttttgttt ccctttcatt    8640 gcacaattct gtcttttgct tactactatg tgtaagtata acagttcaaa gtaatagttt    8700
cataagctgt tggtcatgta gcctttggtc tctttaacct ctttgccaag ttcccaggtt    8760
cataaaatga ggaggttgaa tggaatggtt cccaagagaa ttccttttaa tcttacagaa    8820
attattgttt tcctaaatcc tgtagttgaa tatataatgc tatttacatt tcagtatagt    8880
tttgatgtat ctaaagaaca cattgaattc tccttcctgt gttccagttt gatactaacc    8940
tgaaagtcca ttaagcatta ccagttttaa aaggcttttg cccaatagta aggaaaaata    9000
atatctttta aaagaataat tttttactat gtttgcaggc ttacttcctt ttttctcaca    9060
ttatgaaact cttaaaatca ggagaatctt ttaaacaaca tcataatgtt taatttgaaa    9120
agtgcaagtc attcttttcc tttttgaaac tatgcagatg ttacattgac tgttttctgt    9180
gaagttatct ttttttcact gcagaataaa ggttgttttg atttattttt gtattgttta    9240
tgagaacatg catttgttgg gttaatttcc taccccctgcc cccatttttt ccctaaagta    9300
gaaagtattt ttcttgtgaa ctaaattact acacaagaac atgtctattg aaaaataagc    9360
aagtatcaaa atgttgtggg ttgttttttt aaataaattt tctcttgctc aggaaagaca    9420
agaaaatgtc cagaagatta tcttagaagg cacagagaga atggaagatc aggtatatgc    9480
aaattgcata ctgtcaaatg ttttttctcac agcatgtatc tgtataaggt tgatggctac    9540
atttgtcaag gccttggaga catacgaata agcctttaat ggagctttta tggaggtgta    9600
cagaataaac tggaggaaga tttccatatc ttaaacccaa agagttaaat cagtaaacaa    9660
aggaaaatag taattgcatc tacaaattaa tatttgctcc ctttttttttt ctgtttgccc    9720 agaataaatt ttggataact tgttcatagt aaaaataaaa aaaattgtct ctgatatgtt    9780 cttaaggta ctacttctcg aacctttccc tagaagtagc tgtaacagaa ggagagcata    9840 tgtaccctg aggtatctgt ctggggtgta ggcccaggtc cacacaatat ttcttctaag    9900
tcttatgttt atcgttaag actcatgcaa tttacatttt attccataac tatttagta    9960 ttaaaatttg tcagtgatat ttcttaccct ctcctctagg aaaatgtgcc atgtttatcc    10020
cttggctttg aatgccctc aggaacagac actaagagtt tgagaagcat ggttacaagg    10080
gtgtggcttc ccctgcggaa actaagtaca gactatttca ctgtaaagca gagaagttct    10140
tttgaaggag aatctccagt gaagaaagag ttcttcactt ttacttccat ttcctcttgt    10200
gggtgaccct caatgctcct tgtaaaactc caatatttta aacatggctg ttttgccttt    10260
ctttgcttct ttttagcatg aatgagacag atgatacttt aaaaaagtaa ttaaaaaaaa    10320
aaacttgtga aaatacatgg ccataataca gaacccaata caatgatctc ctttaccaaa    10380
ttgttatgtt tgtacttttg tagatagctt tccaattcag agacagttat tctgtgtaaa    10440
ggtctgactt aacaagaaaa gatttcccctt tacccaaaga atcccagtcc ttatttgctg    10500
gtcaataagc agggtcccca ggaatggggt aactttcagc accctctaac ccactagtta    10560
ttagtagact aattaagtaa acttatcgca agttgaggaa acttagaacc aactaaaatt    10620 ctgctttttac tgggatttttg ttttttcaaa ccagaaacct ttacttaagt tgactactat    10680
```

```
taatgaattt tggtctctct tttaagtgct cttcttaaaa atgttatctt actgctgaga    10740
agttcaagtt tgggaagtac aaggaggaat agaaacttaa gagattttct tttagagcct    10800
cttctgtatt tagccctgta ggattttttt tttttttttt tttttggtg ttgttgagct    10860 tcagtgaggc tattcattca cttatactga taatgtctga gatactgtga atgaaatact    10920
atgtatgctt aaacctaaga ggaaatattt tcccaaaatt attcttccg aaaaggagga    10980 gttgcctttt gattgagttc ttgcaaatct cacaacgact ttattttgaa caatactgtt    11040
tggggatgat gcattagttt gaaacaactt cagttgtagc tgtcatctga taaaattgct    11100
tcacagggaa ggaaatttaa cacggatcta gtcattattc ttgttagatt gaatgtgtga    11160
attgtaattg taaacaggca tgataattat tactttaaaa actaaaaaca gtgaatagtt    11220
agttgtggag gttactaaag gatggttttt ttttaaataa aactttcagc attatgcaaa    11280
tgggcatatg gcttaggata aaacttccag aagtagcatc acatttaaat tctcaagcaa    11340
cttaataata tggggctctg aaaaactggt taaggttact ccaaaaatgg ccctgggtct    11400
gacaaagatt ctaacttaaa gatgcttatg aagactttga gtaaaatcat ttcataaaat    11460
aagtgaggaa aaacaactag tattaaaattc atcttaaata atgtatgatt taaaaaatat    11520
gtttagctaa aaatgcatag tcatttgaca atttcattta tatctcaaaa aatttactta    11580
accaagttgg tcacaaaact gatgagactg gtggtggtag tgaataaatg agggaccatc    11640
catatttgag acactttaca tttgtgatgt gttatactga attttcagtt tgattctata    11700
gactacaaat ttcaaaatta caatttcaag atgtaataag tagtaatatc ttgaaatagc    11760
tctaaaggga atttttctgt tttattgatt cttaaaatat atgtgctgat tttgatttgc    11820
atttgggtag attatacttt tatgagtatg gaggttaggt attgattcaa gttttcctta    11880
cctatttggt aaggatttca aagtctttt gtgcttggtt ttcctcattt ttaaatatga    11940
aatatattga tgacctttaa caaattttt ttatctcaaa ttttaaagga gatcttttct    12000
aaaagaggca tgatgactta atcattgcat gtaacagtaa acgataaacc aatgattcca    12060
tactctctaa agaataaaag tgagctttag ggccgggcat ggtcagaaat ttgacaccaa    12120
cctggccaac atggcgaaac cccgtctcta ctaaaaatac aaaaatcagc cgggcatggt    12180
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa agaaagaata aaagtgagct ttggattgca    12360
tataaatcct ttagacatgt agtagacttg tttgatactg tgtttgaaca aattacgaag    12420
tattttcatc aaagaatgtt attgtttgat gttatttta tttttttattg cccagcttct    12480 ctcatattac gtgattttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660 ttttgggggtt atagtattat tatgtatatt attaatattc taattttaat agtaaggact    12720
ttgtcataca tactattcac atacagtatt agccacttta gcaaataagc acacacaaaa    12780 tcctggatttt tatggcaaaa cagaggcatt tttgatcagt gatgacaaaa ttaaattcat    12840
tttgtttatt tcattacttt tataattcct aaaagtggga ggatcccagc tcttatagga    12900
gcaattaata tttaatgtag tgtctttga aacaaaactg tgtgccaaag tagtaaccat    12960
taatggaagt ttacttgtag tcacaaattt agtttcctta atcatttgtt gaggactttt    13020
tgaatcacac actatgagtg ttaagagata cctttaggaa actattcttg ttgttttctg    13080
```

```
atttttgtcat ttaggttagt ctcctgattc tgacagctca gaagaggaag ttgttcttgt   13140
aaaaattgtt taacctgctt gaccagcttt cacatttgtt cttctgaagt ttatggtagt   13200
gcacagagat tgttttttgg ggagtcttga ttctcggaaa tgaaggcagt gtgttatatt   13260
gaatccagac ttccgaaaac ttgtatatta aaagtgttat ttcaacacta tgttacagcc   13320
agactaattt ttttatttt tgatgcattt tagatagctg atacagtact caatgatgat   13380
gatattggtg acagctgtca tgaaggcttt cttctcaagt aagaattttt cttttcataa   13440
aagctggatg aagcagatac catcttatgc tcacctatga caagatttgg aagaaagaaa   13500
ataacagact gtctacttag attgttctag ggacattacg tatttgaact gttgcttaaa   13560
tttgtgttat ttttcactca ttatatttct atatatattt ggtgttattc catttgctat   13620
ttaaagaaac cgagtttcca tcccagacaa gaaatcatgg cccccttgctt gattctggtt   13680 tcttgttta cttctcatta aagctaacag aatcctttca tattaagttg tactgtagat   13740
gaacttaagt tatttaggcg tagaacaaaa ttattcatat ttatactgat ctttttccat   13800
ccagcagtgg agtttagtac ttaagagttt gtgcccttaa accagactcc ctggattaat   13860
gctgtgtacc cgtgggcaag gtgcctgaat tctctataca cctatttcct catctgtaaa   13920
atggcaataa tagtaatagt acctaatgtg tagggttgtt ataagcattg agtaagataa   13980
ataatataaa gcacttagaa cagtgcctgg aacataaaaa cacttaataa tagctcatag   14040
ctaacatttc ctatttacat ttcttctaga aatagccagt atttgttgag tgcctacatg   14100
ttagttcctt tactagttgc tttacatgta ttatcttata ttctgtttta aagtttcttc   14160
acagttacag attttcatga aatttttactt ttaataaaag agaagtaaaa gtataaagta   14220
ttcactttta tgttcacagt cttttccttt aggctcatga tggagtatca gaggcatgag   14280
tgtgtttaac ctaagagcct taatggcttg aatcagaagc actttagtcc tgtatctgtt   14340
cagtgtcagc ctttcataca tcattttaaa tcccatttga ctttaagtaa gtcacttaat   14400
ctctctacat gtcaatttct tcagctataa aatgatggta tttcaataaa taaatacatt   14460
aattaaatga tattatactg actaattggg ctgttttaag gctcaataag aaaatttctg   14520
tgaaaggtct ctagaaaatg taggttccta tacaaataaa agataacatt gtgcttatag   14580
cttcggtgtt tatcatataa agctattctg agttatttga agagctcacc tactttttt   14640 tgttttagt ttgttaaatt gttttatagg caatgttttt aatctgtttt ctttaactta   14700
cagtgccatc agctcacact tgcaaacctg tggctgttcc gttgtagtag gtagcagtgc   14760
agagaaagta aataaggtag tttatttat aatctagcaa atgatttgac tctttaagac   14820
tgatgatata tcatggattg tcatttaaat ggtaggttgc aattaaaatg atctagtagt   14880
ataaggaggc aatgtaatct catcaaattg ctaagacacc ttgtggcaac agtgagtttg   14940
aaataaactg agtaagaatc atttatcagt ttattttgat agctcggaaa taccagtgtc   15000
agtagtgtat aaatggtttt gagaatatat taaaatcaga tatataaaaa aaattactct   15060
tctatttccc aatgttatct ttaacaaatc tgaagatagt catgtacttt tggtagtagt   15120
tccaaagaaa tgttatttgt ttattcatct tgatttcatt gtcttcgctt tccttctaaa   15180
tctgtcccct ctagggagct attgggatta agtggtcatt gattattata ctttattcag   15240
taatgtttct gacccttttcc ttcagtgcta cttgagttaa ttaaggatta atgaacagtt   15300
acatttccaa gcattagcta ataaactaaa ggatttgca cttttcttca ctgaccatta   15360
gttagaaaga gttcagagat aagtatgtgt atctttcaat ttcagcaaac ctaatttttt   15420
```

```
aaaaaaagtt tacatagga aatatgttgg aaatgatact ttacaaagat attcataatt    15480
tttttttgta atcagctact ttgtatattt acatgagcct taatttatat ttctcatata    15540
accatttatg agagcttagt atacctgtgt cattatattg catctacgaa ctagtgacct    15600
tattccttct gttacctcaa acaggtggct ttccatctgt gatctccaaa gccttaggtt    15660
gcacagagtg actgccgagc tgctttatga agggagaaag gctccatagt tggagtgttt    15720
tttttttttt ttttaaacat ttttcccatc ctccatcctc ttgagggaga atagcttacc    15780
ttttatcttg ttttaatttg agaagaagt tgccaccact ctaggttgaa aaccactcct     15840
ttaacataat aactgtggat atggtttgaa tttcaagata gttacatgcc ttttattt      15900 tcctaataga gctgtaggtc aaatattatt agaatcagat ttctaaatcc cacccaatga    15960
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcacct gaagagtcac    16140
agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtcttttttac ttcatgtttt aatgctaaaa   16380
tattttcttt tatagatagt cagaacatta tgccttttttc tgactccagc agagagaaaa   16440
tgctccaggt tatgtgaagc agaatcatca tttaaatatg agtcagggct ctttgtacaa    16500
ggcctgctaa aggtatagtt tctagttatc acaagtgaaa ccacttttct aaaatcattt    16560
ttgagactct ttatagacaa atcttaaata ttagcattta atgtatctca tattgacatg    16620
cccagagact gacttccttt acacagttct gcacatagac tatatgtctt atggatttat    16680
agttagtatc atcagtgaaa caccatagaa taccctttgt gttccaggtg ggtccctgtt    16740
cctacatgtc tagcctcagg acttttttttt tttttaacaca tgcttaaatc aggttgcaca    16800
tcaaaaataa gatcatttct ttttaactaa atagatttga attttattga aaaaaatttt    16860
taaacatctt taagaagctt ataggattta agcaattcct atgtatgtgt actaaaatat    16920
atatatttct atatataata tatattagaa aaaaattgta ttttttctttt atttgagtct    16980 actgtcaagg agcaaaacag agaaatgtaa attagcaatt atttataata cttaaaggga    17040
agaaagttgt tcaccttgtt gaatctatta ttgttatttc aattatagtc ccaagacgtg    17100
aagaaatagc tttcctaatg gttatgtgat tgtctcatag tgactacttt cttgaggatg    17160
tagccacggc aaaatgaaat aaaaaaattt aaaaattgtt gcaaatacaa gttatattag    17220
gcttttgtgc atttcaata atgtgctgct atgaactcag aatgatagta tttaaatata     17280
gaaactagtt aaaggaaacg tagtttctat ttgagttata catatctgta aattagaact    17340
tctcctgtta aaggcataat aaagtgctta atacttttgt ttcctcagca ccctctcatt    17400
taattatata attttagttc tgaaagggac ctataccaga tgcctagagg aaatttcaaa    17460
actatgatct aatgaaaaaa tatttaatag ttctccatgc aaatacaaat catatagttt    17520
tccagaaaat acctttgaca ttatacaaag atgattatca cagcattata atagtaaaaa    17580
aatggaaata gcctctttct tctgttctgt tcatagcaca gtgcctcata cgcagtaggt    17640
tattattaca tggtaactgg ctaccccaac tgattaggaa agaagtaaat tgtttttata    17700
aaaatacata ctcattgagg tgcatagaat aattaagaaa ttaaaagaca cttgtaattt    17760
tgaatccagt gaatacccac tgttaatatt tggtatatct cttctagtc ttttttttccc     17820
```

```
ttttgcatgt attttctttta agactcccac ccccactgga tcatctctgc atgttctaat      17880
ctgctttttt cacagcagat tctaagcctc tttgaatatc aacacaaact tcaacaactt      17940
catctataga tgccaaataa taaattcatt tttatttact taaccacttc ctttggatgc      18000
ttaggtcatt ctgatgtttt gctattgaaa ccaatgctat actgaacact tctgtcacta      18060
aaactttgca cacactcatg aatagcttct taggataaat ttttagagat ggatttgcta      18120
aatcagagac cattttttaa aattaaaaaa caattattca tatcgtttgg catgtaagac      18180
agtaaatttt ccttttattt tgacaggatt caactggaag ctttgtgctg cctttccggc      18240
aagtcatgta tgctccatat cccaccacac acatagatgt ggatgtcaat actgtgaagc      18300
agatgccacc ctgtcatgaa catatttata atcagcgtag atacatgaga tccgagctga      18360
cagccttctg gagagccact tcagaagaag acatggctca ggatacgatc atctacactg      18420
acgaaagctt tactcctgat ttgtacgtaa tgctctgcct gctggtactg tagtcaagca      18480
atatgaaatt gtgtctttta cgaataaaaa caaaacagaa gttgcattta aaagaaaga      18540
aatattacca gcagaattat gcttgaagaa acatttaatc aagcattttt ttcttaaatg      18600
ttcttctttt tccatacaat tgtgtttacc ctaaaatagg taagattaac ccttaaagta      18660
aatatttaac tatttgttta ataaatatat attgagctcc taggcactgt tctaggtacc      18720
gggcttaata gtggccaacc agacagcccc agccccagcc cctacattgt gtatagtcta      18780
ttatgtaaca gttattgaat ggacttatta acaaaaccaa agaagtaatt ctaagtcttt      18840
tttttcttga catatgaata taaaatacag caaaactgtt aaaatatatt aatggaacat      18900
ttttttactt tgcattttat attgttattc acttcttatt ttttttttaaa aaaaaaagcc      18960
tgaacagtaa attcaaaagg aaaagtaatg ataattaatt gttgagcatg gacccaactt      19020
gaaaaaaaaa atgatgatga taaatctata atcctaaaac cctaagtaaa cacttaaaag      19080
atgttctgaa atcaggaaaa gaattatagt atacttttgt gtttctcttt tatcagttga      19140
aaaaaggcac agtagctcat gcctgtaaga acagagcttt gggagtgcaa ggcaggcgga      19200
tcacttgagg ccaggagttc cagaccagcc tgggcaacat agtgaaaccc catctctaca      19260
aaaaataaaa aagaattatt ggaatgtgtt tctgtgtgcc tgtaatccta gctattccga      19320
aagctgaggc aggaggatct tttgagccca ggagtttgag gttacaggga gttatgatgt      19380
gccagtgtac tccagcctgg ggaacaccga gactctgtct tatttaaaaa aaaaaaaaaa      19440
aaaatgcttg caataatgcc tggcacatag aaggtaacag taagtgttaa ctgtaataac      19500
ccaggtctaa gtgtgtaagg caatagaaaa attggggcaa ataagcctga cctatgtatc      19560
tacagaatca gtttgagctt aggtaacaga cctgtggagc accagtaatt acacagtaag      19620
tgttaaccaa aagcatagaa taggaatatc ttgttcaagg gacccccagc cttatacatc      19680
tcaaggtgca gaaagatgac ttaatatagg acccattttt tcctagttct ccagagtttt      19740
tattggttct tgagaaagta gtaggggaat gttttagaaa atgaattggt ccaactgaaa      19800
ttacatgtca gtaagttttt atatattggt aaatttagt agacatgtag aagttttcta      19860
attaatctgt gccttgaaac atttttcttt tcctaaagt gcttagtatt ttttccgttt      19920
tttgattggt tacttgggag ctttttttgag gaaatttagt gaactgcaga atgggtttgc      19980
aaccatttgg tattttttgtt ttgttttta gaggatgtat gtgtatttta acatttctta      20040
atcattttta gccagctatg tttgttttgc tgatttgaca aactacagtt agacagctat      20100
tctcattttg ctgatcatga caaaataata tcctgaattt ttaaatttg catccagctc      20160
```

-continued

| | | | | | |
|---|---|---|---|---|---|
| taaattttct | aaacataaaa | ttgtccaaaa | aatagtattt | tcagccacta | gattgtgtgt | 20220 |
| taagtctatt | gtcacagagt | cattttactt | ttaagtatat | gtttttacat | gttaattatg | 20280 |
| tttgttattt | ttaattttaa | cttttaaaa | taattccagt | cactgccaat | acatgaaaaa | 20340 |
| ttggtcactg | gaattttttt | tttgacttt | attttaggtt | catgtgtaca | tgtgcaggtg | 20400 |
| tgttatacag | gtaaattgcg | tgtcatgagg | gtttggtgta | caggtgattt | cattacccag | 20460 |
| gtaataagca | tagtacccaa | taggtagttt | tttgatcctc | acccttctcc | caccctcaag | 20520 |
| taggccctgg | tgttgctgtt | tccttctttg | tgtccatgta | tactcagtgt | ttagctccca | 20580 |
| cttagaagtg | agaacatgcg | gtagttggtt | ttctgttcct | ggattagttc | acttaggata | 20640 |
| atgacctcta | gctccatctg | gtttttatgg | ctgcatagta | ttccatggtg | tatatgtatc | 20700 |
| acattttctt | tatccagtct | accattgata | ggcattttagg | ttgattccct | gtctttgtta | 20760 |
| tcatgaatag | tgctgtgatg | aacatacaca | tgcatgtgtc | tttatggtag | aaaaatttgt | 20820 |
| attcctttag | gtacatatag | aataatgggg | ttgctagggt | gaatggtagt | tctattttca | 20880 |
| gttatttgag | aaatcttcaa | actgcttttc | ataatagcta | aactaattta | cagtcccgcc | 20940 |
| agcagtgtat | aagtgttccc | ttttctccac | aaccttgcca | acatctgtga | ttttttgact | 21000 |
| ttttaataat | agccattcct | agagaattga | tttgcaattc | tctattagtg | atattaagca | 21060 |
| ttttttcata | tgcttttag | ctgtctgtat | atattcttct | gaaaaatttt | catgtccttt | 21120 |
| gcccagtttg | tagtggggtg | ggtgttttt | tgcttgttaa | ttagtttaa | gttccttcca | 21180 |
| gattctgcat | atcccttgt | tggatacatg | gtttgcagat | attttctcc | cattgtgtag | 21240 |
| gttgtctttt | actctgttga | tagtttcttt | tgccatgcag | gagctcgtta | ggtcccattt | 21300 |
| gtgtttgttt | ttgttgcagt | tgcttttggc | gtcttcatca | taaaatctgt | gccagggcct | 21360 |
| atgtccagaa | tggtatttcc | taggttgtct | tccagggttt | ttacaatttt | agattttacg | 21420 |
| tttatgtctt | taatccatct | tgagttgatt | tttgtatatg | gcacaaggaa | ggggtccagt | 21480 |
| ttcactccaa | ttcctatggc | tagcaattat | cccagcacca | tttattgaat | acggagtcct | 21540 |
| ttccccattg | cttgtttttt | gtcaactttg | ttgaagatca | gatggttgta | agtgtgtggc | 21600 |
| tttatttctt | ggctctctat | tctccattgg | tctatgtgtc | tgttttttata | acagtaccct | 21660 |
| gctgttcagg | ttcctatagc | cttttagtat | aaaatcggct | aatgtgatgc | ctccagcttt | 21720 |
| gttcttttg | cttaggattg | ctttggctat | ttgggctcct | ttttgggtcc | atattaattt | 21780 |
| taaaacagtt | ttttctggtt | ttgtgaagga | tatcattggt | agtttatagg | aatagcattg | 21840 |
| aatctgtaga | ttgctttggg | cagtatggcc | attttaacaa | tattaattct | tcctatctat | 21900 |
| gaatatggaa | tgttttcca | tgtgtttgtg | tcatctcttt | atacctgatg | tataaagaaa | 21960 |
| agctggtatt | attcctactc | aatctgttcc | aaaaaattga | ggaggaggaa | ctcttcccta | 22020 |
| atgaggccag | catcattctg | ataccaaaac | ctggcagaga | cacaacagaa | aaaagaaaac | 22080 |
| ttcaggccaa | tatccttgat | gaatatagat | gcaaaatcc | tcaacaaaat | actagcaaac | 22140 |
| caaatccagc | agcacatcaa | aaagctgatc | tactttgatc | aagtaggctt | tatccctggg | 22200 |
| atgcaaggtt | ggttcaacat | acacaaatca | ataagtgtga | ttcatcacat | aaacagagct | 22260 |
| aaaaacaaaa | accacaagat | tatctcaata | ggtagagaaa | aggttgtcaa | taaaatttaa | 22320 |
| catcctccat | gttaaaaacc | ttcagtaggt | caggtgtagt | gactcacacc | tgtaatccca | 22380 |
| gcactttggg | aggccaaggc | gggcatatct | cttaagccca | ggagttcaag | acgagcctag | 22440 |
| gcagcatggt | gaaaccccat | ctctacaaaa | aaaaaaaaa | aaaaaatta | gcttggtatg | 22500 |
| gtgacatgca | cctatagtcc | cagctattca | ggaggttgag | gtgggaggat | tgtttgagcc | 22560 |

```
cgggaggcag aggttggcag cgagctgaga tcatgccacc gcactccagc ctgggcaacg   22620
gagtgagacc ctgtctcaaa aagaaaaat cacaaacaat cctaaacaaa ctaggcattg   22680
aaggaacatg cctcaaaaaa ataagaacca tctatgacag acccatagcc aatatcttac   22740
caaatgggca aaagctggaa gtattctcct tgagaaccgt aacaagacaa ggatgtccac   22800
tctcaccact cctttcagc atagttctgg aagtcctagc cagagcaatc aggaaagaga   22860
aagaaagaaa gacattcaga taggaagaga agaagtcaaa ctatttctgt ttgcaggcag   22920
tataattctg tacctagaaa atctcatagt ctctgcccag aaactcctaa atctgttaaa   22980
aatttcagca aagttttggc attctctata ctccaacacc ttccaaagtg agagcaaaat   23040
caagaacaca gtcccattca caatagccgc aaaacgaata aaatacctag gaatccagct   23100
aaccagggag gtgaaagatc tctatgagaa ttacaaaaca ctgctgaaag aaatcagaga   23160
tgacacaaac aaatggaaat gttctttttt aacaccttgc tttatctaat tcacttatga   23220
tgaagatact cattcagtgg aacaggtata ataagtccac tcgattaaat ataagcctta   23280
ttctctttcc agagcccaag aagggcact atcagtgccc agtcaataat gacgaaatgc   23340 taatatttt cccctttacg gtttctttct tctgtagtgt ggtacactcg tttcttaaga   23400
taaggaaact tgaactacct tcctgtttgc ttctacacat acccattctc ttttttgcc   23460 actctggtca ggtataggat gatccctacc actttcagtt aaaaactcct cctcttacta   23520
aatgttctct taccctctgg cctgagtaga acctagggaa aatggaagag aaaaagatga   23580
aagggaggtg gggcctggga agggaataag tagtcctgtt tgtttgtgtg tttgctttag   23640
cacctgctat atcctaggtg ctgtgttagg cacacattat tttaagtggc cattatatta   23700
ctactactca ctctggtcgt tgccaaggta ggtagtactt tcttggatag ttggttcatg   23760
ttacttacag atggtgggct tgttgaggca aacccagtgg ataatcatcg gagtgtgttc   23820
tctaatctca ctcaaatttt tcttcacatt ttttggtttg ttttggtttt tgatggtagt   23880
ggcttatttt tgttgctggt ttgttttttg tttttttg agatggcaag aattggtagt   23940
tttatttatt aattgcctaa gggtctctac tttttttaaa agatgagagt agtaaaatag   24000
attgatagat acatacatac ccttactggg gactgcttat attctttaga gaaaaaatta   24060
catattagcc tgacaaacac cagtaaaatg taaatatatc cttgagtaaa taaatgaatg   24120 tatatttgt gtctccaaat atatatct atattcttac aaatgtgttt atatgtaata   24180
tcaatttata agaacttaaa atgttggctc aagtgaggga ttgtggaagg tagcattata   24240
tggccatttc aacatttgaa cttttttctt ttcttcattt tcttcttttc ttcaggaata   24300 ttttcaaga tgtcttacac agagacactc tagtgaaagc cttcctggat caggtaaatg   24360
ttgaacttga gattgtcaga gtgaatgata tgacatgttt tcttttttaa tatatcctac   24420
aatgcctgtt ctatatattt atattcccct ggatcatgcc ccagagttct gctcagcaat   24480
tgcagttaag ttagttacac tacagttctc agaagagtct gtgagggcat gtcaagtgca   24540
tcattacatt ggttgcctct tgtcctagat ttatgcttcg ggaattcaga cctttgttta   24600
caatataata aatattattg ctatctttta aagatataat aataagatat aaagttgacc   24660
acaactactg ttttttgaaa catagaattc ctggtttaca tgtatcaaag tgaaatctga   24720
cttagctttt acagatataa tatatacata tatatatcct gcaatgcttg tactatatat   24780
gtagtacaag tatatatata tgtttgtgtg tgtatatata tatagtacga gcatatatac   24840
atattaccag cattgtagga tatatatatg tttatatatt aaaaaaaagt tataaactta   24900
```

```
aaaccctatt atgttatgta gagtatatgt tatatatgat atgtaaaata tataacatat    24960
actctatgat agagtgtaat atatttttta tatatatttt aacatttata aaatgataga    25020
attaagaatt gagtcctaat ctgttttatt aggtgctttt tgtagtgtct ggtctttcta    25080
aagtgtctaa atgatttttc cttttgactt attaatgggg aagagcctgt atattaacaa    25140
ttaagagtgc agcattccat acgtcaaaca acaaacattt taattcaagc attaacctat    25200
aacaagtaag tttttttttt tttttgaga aagggaggtt gtttatttgc ctgaaatgac     25260 tcaaaatat  ttttgaaaca tagtgtactt atttaaataa catctttatt gtttcattct    25320
tttaaaaaat atctacttaa ttacacagtt gaaggaaatc gtagattata tggaacttat    25380
ttcttaatat attacagttt gttataataa cattctgggg atcaggccag gaaactgtgt    25440
catagataaa gctttgaaat aatgagatcc ttatgtttac tagaaatttt ggattgagat    25500
ctatgaggtc tgtgacatat tgcgaagttc aaggaaaatt cgtaggcctg gaatttcatg    25560
cttctcaagc tgacataaaa tccctcccac tctccacctc atcatatgca cacattctac    25620
tcctacccac ccactccacc ccctgcaaaa gtacaggtat atgaatgtct caaaaccata    25680
ggctcatctt ctaggagctt caatgttatt tgaagatttg ggcagaaaaa attaagtaat    25740
acgaaataac ttatgtatga gttttaaaag tgaagtaaac atggatgtat tctgaagtag    25800
aatgcaaaat ttgaatgcat ttttaaagat aaattagaaa acttctaaaa actgtcagat    25860
tgtctgggcc tggtggctta tgcctgtaat cccagcactt tgggagtccg aggtgggtgg    25920
atcacaaggt caggagatcg agaccatcct gccaacatgg tgaaaccccg tctctactaa    25980
gtatacaaaa attagctggg cgtggcagcg tgtgcctgta atcccagcta cctgggaggc    26040
tgaggcagga gaatcgcttg aacccaggag gtgtaggttg cagtgagtca agatcgcgcc    26100
actgcacttt agcctggtga cagagctaga ctccgtctca aaaaaaaaa  aaaatatcag    26160 attgttccta cacctagtgc ttctatacca cactcctgtt agggggcatc agtggaaatg    26220
gttaaggaga tgtttagtgt gtattgtctg ccaagcactg tcaacactgt catagaaact    26280
tctgtacgag tagaatgtga gcaaattatg tgttgaaatg gttcctctcc ctgcaggtct    26340
ttcagctgaa acctggctta tctctcagaa gtactttcct tgcacagttt ctacttgtcc    26400
ttcacagaaa agccttgaca ctaataaaat atatagaaga cgatacgtga gtaaaactcc    26460
tacacggaag aaaaaccttt gtacattgtt tttttgtttt gtttcctttg tacatttttct   26520 atatcataat ttttgcgctt cttttttttt tttttttttt ttttttttcca ttattttttag 26580 gcagaaggga aaaagcccct ttaaatctct tcggaacctg aagatagacc ttgatttaac    26640
agcagagggc gatcttaaca taataatggc tctggctgag aaaattaaac caggcctaca    26700
ctcttttatc tttggaagac cttttctacac tagtgtgcaa gaacgagatg ttctaatgac   26760 ttttttaaatg tgtaacttaa taagcctatt ccatcacaat catgatcgct ggtaaagtag   26820
ctcagtggtg tggggaaacg ttcccctgga tcatactcca gaattctgct ctcagcaatt    26880
gcagttaagt aagttacact acagttctca caagagcctg tgaggggatg tcaggtgcat    26940
cattacattg ggtgtctctt ttcctagatt tatgcttttg ggatacagac ctatgtttac    27000
aatataataa atattattgc tatcttttaa agatataata ataggatgta aacttgacca    27060
caactactgt ttttttgaaa tacatgattc atggtttaca tgtgtcaagg tgaaatctga    27120
gttggctttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
```

```
attggaattg attattagat cctactttgt ggatttagtc cctgggattc agtctgtaga   27360
aatgtctaat agttctctat agtccttgtt cctggtgaac cacagttagg gtgttttgtt   27420
tattttattg ttcttgctat tgttgatatt ctatgtagtt gagctctgta aaaggaaatt   27480
gtattttatg ttttagtaat tgttgccaac ttttaaatt aattttcatt atttttgagc    27540
caaattgaaa tgtgcacctc ctgtgccttt tttctcctta gaaaatctaa ttacttggaa   27600
caagttcaga tttcactggt cagtcatttt catcttgttt tcttcttgct aagtcttacc   27660
atgtacctgc tttggcaatc attgcaactc tgagattata aaatgcctta gagaatatac   27720
taactaataa gatcttttt tcagaaacag aaaatagttc cttgagtact tccttcttgc    27780
atttctgcct atgttttga agttgttgct gtttgcctgc aataggctat aaggaatagc    27840
aggagaaatt ttactgaagt gctgttttcc taggtgctac tttggcagag ctaagttatc   27900
ttttgttttc ttaatgcgtt tggaccattt tgctggctat aaaataactg attaatataa   27960
ttctaacaca atgttgacat tgtagttaca caaacacaaa taaatatttt atttaaaatt   28020
ctggaagtaa tataaaaggg aaaatatatt tataagaaag ggataaaggt aatagagccc   28080
ttctgccccc cacccaccaa atttacacaa caaaatgaca tgttcgaatg tgaaaggtca   28140
taatagcttt cccatcatga atcagaaaga tgtggacagc ttgatgtttt agacaaccac   28200
tgaactagat gactgttgta ctgtagctca gtcatttaaa aaatatataa atactacctt   28260
gtagtgtccc atactgtgtt ttttacatgg tagattctta tttaagtgct aactggttat   28320 tttcttggc tggtttattg tactgttata cagaatgtaa gttgtacagt gaaataagtt    28380
attaaagcat gtgtaaacat tgttatatat cttttctcct aaatggagaa ttttgaataa   28440
aatatatttg aaattttgcc tctttcagtt gttcattcag aaaaaaatac tatgatattt   28500
gaagactgat cagcttctgt tcagctgaca gtcatgctgg atctaaactt ttttaaaat    28560 taattttgtc ttttcaaaga aaaatatttt aaagaagctt tataatataa tcttatgtta   28620
aaaaactttt ctgcttaact ctctggattt cattttgatt tttcaaatta tatattaata   28680
tttcaaatgt aaaatactat ttagataaat tgttttaaa cattcttatt attataaat     28740 taatataacc taaactgaag ttattcatcc caggtatcta atacatgtat ccaaagtaaa   28800
aatccaagga atctgaacac tttcatctgc aaagctagga ataggtttga cattttcact   28860
ccaagaaaaa gttttttttt gaaaatagaa tagttgggat gagaggtttc tttaaaagaa   28920
gactaactga tcacattact atgattctca aagaagaaac caaaacttca tataatacta   28980
taaagtaaat ataaaatagt tccttctata gtatatttct ataatgctac agtttaaaca   29040
gatcactctt atataatact attttgattt tgatgtagaa ttgcacaaat tgatatttct   29100
cctatgatct gcagggtata gcttaaagta acaaaaacag tcaaccacct ccatttaaca   29160
cacagtaaca ctatgggact agttttatta cttccatttt acaaatgagg aaactaaagc   29220
ttaaagatgt gtaatacacc gcccaaggtc acacagctgg taaaggtgga tttcatccca   29280
gacagttaca gtcattgcca tgggcacagc tcctaactta gtaactccat gtaactggta   29340
ctcagtgtag ctgaattgaa aggagagtaa ggaagcaggt tttacaggtc tacttgcact   29400
attcagagcc cgagtgtgaa tccctgctgt gctgcttgga gaagttactt aacctatgca   29460
aggttcattt tgtaaatatt ggaaatggag tgataatacg tacttcacca gaggatttaa   29520 tgagaccttta tacgatccttt agttcagtac ctgactagtg cttcataaat gcttttcat   29580 ccaatctgac aatctccagc ttgtaattgg ggcatttaga acatttaata tgattattgg   29640
```

| | |
|---|---|
| catggtaggt taaagctgtc atcttgctgt tttctatttg ttcttttgt tttctcctta | 29700 |
| cttttggatt tttttattct actatgtctt ttctattgtc ttattaacta tactctttga | 29760 |
| tttatttag tggttgtttt agggttatac ctctttctaa tttaccagtt tataaccagt | 29820 |
| ttatatacta cttgacatat agcttaagaa acttactgtt gttgtctttt tgctgttatg | 29880 |
| gtcttaacgt ttttatttct acaaacatta taaactccac actttattgt ttttttaattt | 29940 |
| tacttataca gtcaattatc ttttaaagat atttaaatat aaacattcaa aacaccccaa | 30000 |
| t | 30001 |

<210> SEQ ID NO 3
<211> LENGTH: 1031
<212> TYPE: DNA
<213> ORGANISM: Homo sapiens

<400> SEQUENCE: 3

| | |
|---|---|
| attcccggga tacgtaacct acggtgtccc gctaggaaag agaggtgcgt caaacagcga | 60 |
| caagttccgc ccacgtaaaa gatgacgctt ggtgtgtcag ccgtccctgc tgcccggttg | 120 |
| cttctctttt gggggcgggg tctagcaaga gcaggtgtgg gtttaggaga tatctccgga | 180 |
| gcatttggat aatgtgacag ttggaatgca gtgatgtcga ctctttgccc accgccatct | 240 |
| ccagctgttg ccaagacaga gattgcttta agtggcaaat cacctttatt agcagctact | 300 |
| tttgcttact gggacaatat tcttggtcct agagtaaggc acatttgggc tccaaagaca | 360 |
| gaacaggtac ttctcagtga tggagaaata acttttcttg ccaaccacac tctaaatgga | 420 |
| gaaatccttc gaaatgcaga gagtggtgct atagatgtaa agttttttgt cttgtctgaa | 480 |
| aagggagtga ttattgtttc attaatcttt gatggaaact ggaatgggga tcgcagcaca | 540 |
| tatggactat caattatact tccacagaca gaacttagtt tctacctccc acttcataga | 600 |
| gtgtgtgttg atagattaac acatataatc cggaaggaa gaatatggat gcataaggaa | 660 |
| agacaagaaa aatgtccaga agattatctt agaaggcaca gagagaatgg aagatcaggg | 720 |
| tcagagtatt attccaatgc ttactggaga agtgattcct gtaatggaaa ctgctttcct | 780 |
| ctatgaaatt ccccccgggtt cctggaggaa atagatatag gctgatacag ttacccaatg | 840 |
| atggatgaat attgggggac cgcctggtca ttgaaaggct ttcttttctc caggaaagaa | 900 |
| attttttcc ttttccataa aaagcttggg aatggaagac aacaattccc attctttttt | 960 |
| tgcgttccac ccctatgtga acagaaaat ttttggggaa acaacaacga aaaaatttta | 1020 |
| tcccgcgcgc a | 1031 |

<210> SEQ ID NO 4
<211> LENGTH: 3244
<212> TYPE: DNA
<213> ORGANISM: Homo sapiens

<400> SEQUENCE: 4

| | |
|---|---|
| gggcggggct gcggttgcgg tgcctgcgcc cgcggcggcg gaggcgcagg cggtggcgag | 60 |
| tggatatctc cggagcattt ggataatgtg acagttggaa tgcagtgatg tcgactcttt | 120 |
| gcccaccgcc atctccagct gttgccaaga cagagattgc tttaagtggc aaatcacctt | 180 |
| tattagcagc tacttttgct tactgggaca atattcttgg tcctagagta aggcacattt | 240 |
| gggctccaaa gacagaacag gtacttctca gtgatggaga ataacttttt cttgccaacc | 300 |
| acactctaaa tggagaaatc cttcgaaatg cagagagtgg tgctatagat gtaaagtttt | 360 |
| ttgtcttgtc tgaaaaggga gtgattattg tttcattaat ctttgatgga aactggaatg | 420 |

```
gggatcgcag cacatatgga ctatcaatta tacttccaca gacagaactt agtttctacc    480
tcccacttca tagagtgtgt gttgatagat taacacatat aatccggaaa ggaagaatat    540
ggatgcataa ggaaagacaa gaaaatgtcc agaagattat cttagaaggc acagagagaa    600
tggaagatca gggtcagagt attattccaa tgcttactgg agaagtgatt cctgtaatgg    660
aactgctttc atctatgaaa tcacacagtg ttcctgaaga aatagatata gctgatacag    720
tactcaatga tgatgatatt ggtgacagct gtcatgaagg cttccttctc aatgccatca    780
gctcacactt gcaaacctgt ggctgttccg ttgtagtagg tagcagtgca gagaaagtaa    840
ataagatagt cagaacatta tgcctttttc tgactccagc agagagaaaa tgctccaggt    900
tatgtgaagc agaatcatca tttaaatatg agtcagggct cttttgtacaa ggcctgctaa    960
aggattcaac tggaagcttt gtgctgcctt tccggcaagt catgtatgct ccatatccca   1020
ccacacacat agatgtggat gtcaatactg tgaagcagat gccaccctgt catgaacata   1080
tttataatca gcgtagatac atgagatccg agctgacagc cttctggaga gccacttcag   1140
aagaagacat ggctcaggat acgatcatct acactgacga aagctttact cctgatttga   1200
atattttttca agatgtctta cacagagaca ctctagtgaa agccttcctg gatcaggtct   1260
ttcagctgaa acctggctta tctctcagaa gtactttcct tgcacagttt ctacttgtcc   1320
ttcacagaaa agccttgaca ctaataaaat atatagaaga cgatacgcag aagggaaaaa   1380
agcccttaa atctcttcgg aacctgaaga tagaccttga tttaacagca gagggcgatc   1440
ttaacataat aatggctctg gctgagaaaa ttaaaccagg cctacactct tttatctttg   1500
gaagaccttt ctacactagt gtgcaagaac gagatgttct aatgactttt taaatgtgta   1560
acttaataag cctattccat cacaatcatg atcgctggta aagtagctca gtggtgtggg   1620
gaaacgttcc cctggatcat actccagaat tctgctctca gcaattgcag ttaagtaagt   1680
tacactacag ttctcacaag agcctgtgag gggatgtcag gtgcatcatt acattgggtg   1740
tctcttttcc tagatttatg cttttgggat acagacctat gtttacaata taataaatat   1800
tattgctatc ttttaaagat ataataatag gatgtaaact tgaccacaac tactgttttt   1860
ttgaaataca tgattcatgg tttacatgtg tcaaggtgaa atctgagttg gcttttacag   1920
atagttgact ttctatcttt tggcattctt tggtgtgtag aattactgta atacttctgc   1980
aatcaactga aaactagagc cttaaaatga tttcaattcc acagaaagaa agtgagcttg   2040
aacataggat gagctttaga aagaaaattg atcaagcaga tgtttaattg gaattgatta   2100
ttagatccta ctttgtggat ttagtccctg ggattcagtc tgtagaaatg tctaatagtt   2160
ctctatagtc cttgttcctg gtgaaccaca gttagggtgt tttgtttatt ttattgttct   2220
tgctattgtt gatattctat gtagttgagc tctgtaaaag gaaattgtat tttatgtttt   2280
agtaattgtt gccaactttt taaattaatt ttcattattt ttgagccaaa ttgaaatgtg   2340
cacctcctgt gcctttttc tcctttagaaa atctaattac ttggaacaag ttcagatttc   2400
actggtcagt cattttcatc ttgttttctt cttgctaagt cttaccatgt acctgctttg   2460
gcaatcattg caactctgag attataaaat gccttagaga atatactaac taataagatc   2520
ttttttttcag aaacagaaaa tagttccttg agtacttcct tcttgcattt ctgcctatgt   2580
ttttgaagtt gttgctgttt gcctgcaata ggctataagg aatagcagga gaaattttac   2640
tgaagtgctg ttttcctagg tgctactttg gcagagctaa gttatctttt gttttcttaa   2700
tgcgtttgga ccatttttgct ggctataaaa taactgatta atataattct aacacaatgt   2760
```

| | |
|---|---|
| tgacattgta gttacacaaa cacaaataaa tattttattt aaaattctgg aagtaatata | 2820 |
| aaagggaaaa tatatttata agaaagggat aaaggtaata gagcccttct gccccccacc | 2880 |
| caccaaattt acacaacaaa atgacatgtt cgaatgtgaa aggtcataat agctttccca | 2940 |
| tcatgaatca gaaagatgtg gacagcttga tgttttagac aaccactgaa ctagatgact | 3000 |
| gttgtactgt agctcagtca tttaaaaaat atataaatac taccttgtag tgtcccatac | 3060 |
| tgtgtttttt acatggtaga ttcttattta agtgctaact ggttattttc tttggctggt | 3120 |
| ttattgtact gttatacaga atgtaagttg tacagtgaaa taagttatta aagcatgtgt | 3180 |
| aaacattgtt atatatcttt tctcctaaat ggagaatttt gaataaaata tatttgaaat | 3240 |
| tttg | 3244 |

<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5

| | |
|---|---|
| cacgaggctt tgatatttct tacaacgaat ttcatgtgta gacccactaa acagaagcta | 60 |
| taaaagttgc atggtcaaat aagtctgaga aagtctgcag atgatataat tcacctgaag | 120 |
| agtcacagta tgtagccaaa tgttaaaggt tttgagatgc catacagtaa atttaccaag | 180 |
| cattttctaa atttatttga ccacagaatc cctattttaa gcaacaactg ttacatccca | 240 |
| tggattccag gtgactaaag aatacttatt tcttaggata tgttttattg ataataacaa | 300 |
| ttaaaatttc agatatcttt cataagcaaa tcagtggtct ttttacttca tgttttaatg | 360 |
| ctaaaatatt ttcttttata gatagtcaga acattatgcc ttttctgac tccagcagag | 420 |
| agaaaatgct ccaggttatg tgaagcagaa tcatcattta aatatgagtc agggctcttt | 480 |
| gtacaaggcc tgctaaagga ttcaactgga agctttgtgc tgccttccg gcaagtcatg | 540 |
| tatgctccat atcccaccac acacatagat gtggatgtca atactgtgaa gcagatgcca | 600 |
| ccctgtcatg aacatattta taatcagcgt agatacatga gatccgagct gacagccttc | 660 |
| tggagagcca cttcagaaga agacatggct cangatacga tcatctacac tgacgaaagc | 720 |
| tntactcctg atttgaatat ttttcaagat gtcttacaca g | 761 |

<210> SEQ ID NO 6
<211> LENGTH: 1901
<212> TYPE: DNA
<213> ORGANISM: Homo sapiens

<400> SEQUENCE: 6

| | |
|---|---|
| acgtaaccta cggtgtcccg ctaggaaaga gaggtgcgtc aaacagcgac aagttccgcc | 60 |
| cacgtaaaag atgacgcttg atatctccgg agcatttgga taatgtgaca gttggaatgc | 120 |
| agtgatgtcg actctttgcc caccgccatc tccagctgtt gccaagacag agattgcttt | 180 |
| aagtggcaaa tcacctttat tagcagctac ttttgcttac tgggacaata ttcttggtcc | 240 |
| tagagtaagg cacatttggg ctccaaagac agaacaggta cttctcagtg atggagaaat | 300 |
| aacttttctt gccaaccaca ctctaaatgg agaaatcctt cgaaatgcag agagtggtgc | 360 |

```
tatagatgta aagttttttg tcttgtctga aaagggagtg attattgttt cattaatctt     420
tgatggaaac tggaatgggg atcgcagcac atatggacta tcaattatac ttccacagac     480
agaacttagt ttctacctcc cacttcatag agtgtgtgtt gatagattaa cacatataat     540
ccggaaagga agaatatgga tgcataagga aagacaagaa aatgtccaga agattatctt     600
agaaggcaca gagagaatgg aagatcaggg tcagagtatt attccaatgc ttactggaga     660
agtgattcct gtaatggaac tgctttcatc tatgaaatca cacagtgttc ctgaagaaat     720
agatatagct gatacagtac tcaatgatga tgatattggt gacagctgtc atgaaggctt     780
tcttctcaag taagaatttt tcttttcata aaagctggat gaagcagata ccatcttatg     840
ctcacctatg acaagatttg gaagaaagaa aataacagac tgtctactta gattgttcta     900
gggacattac gtatttgaac tgttgcttaa atttgtgtta ttttcactc attatatttc      960 tatatatatt tggtgttatt ccatttgcta tttaaagaaa ccgagtttcc atcccagaca    1020
agaaatcatg gccccttgct tgattctggt ttcttgtttt acttctcatt aaagctaaca    1080
gaatcctttc atattaagtt gtactgtaga tgaacttaag ttatttaggc gtagaacaaa    1140
attattcata tttatactga tcttttttcca tccagcagtg gagtttagta cttaagagtt    1200 tgtgcccttta aaccagactc cctggattaa tgctgtgtac ccgtgggcaa ggtgcctgaa    1260
ttctctatac acctatttcc tcatctgtaa aatggcaata atagtaatag tacctaatgt    1320
gtagggttgt tataagcatt gagtaagata aataatataa agcacttaga acagtgcctg    1380
gaacataaaa acacttaata atagctcata gctaacattt cctatttaca tttcttctag    1440
aaatagccag tatttgttga gtgcctacat gttagttcct ttactagttg ctttacatgt    1500
attatcttat attctgtttt aaagtttctt cacagttaca gattttcatg aaatttttact   1560 tttaataaaa gagaagtaaa agtataaagt attcactttt atgttcacag tcttttcctt    1620
taggctcatg atggagtatc agaggcatga gtgtgtttaa cctaagagcc ttaatggctt    1680
gaatcagaag cactttagtc ctgtatctgt tcagtgtcag cctttcatac atcattttaa    1740
atcccatttg actttaagta agtcacttaa tctctctaca tgtcaatttc ttcagctata    1800
aaatgatggt atttcaataa ataaatacat taattaaatg atattatact gactaattgg    1860
gctgttttaa ggcaaaaaaa aaaaaaaaaa aaaaaaaaa a                          1901
```

<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

```
agacgtaacc tacggtgtcc cgctaggaaa gagagatatc tccggagcat ttggataatg      60
tgacagttgg aatgcagtga tgtcgactct ttgcccaccg ccatctccag ctgttgccaa     120
gacagagatt gctttaagtg gcaaatcacc tttattagca gctacntttt gcttactggg     180
acaatattct tggtcctaga gtaaggcaca tttgggctcc aaagacagaa caggtacttc     240
tcagtgatgg agaaataact tttcttgcca accacactct aaatggagaa atccttcgaa     300
atgcagagag tggtgctata gatgtaaagt ttttttgtctt gtctgaaaag ggagtgatta    360
ttgtttcatt aatctttgat ggaaactgga atggggatcg cagcacatat ggactatcaa    420
```

| | |
|---|---|
| ttatacttcc acagacagaa cttagttct acctcccact tcatagagtg tgtgttgata | 480 |
| gattaacaca tataatccgg aaaggaagaa tatggatgca taaggaaaga caagaaaatg | 540 |
| tccagaagat tatcttagaa gg | 562 |

<210> SEQ ID NO 8
<211> LENGTH: 798
<212> TYPE: DNA
<213> ORGANISM: Homo sapiens

<400> SEQUENCE: 8

| | |
|---|---|
| gggctctctt ttgggggcgg ggtctagcaa gagcagatat ctccggagca tttggataat | 60 |
| gtgacagttg gaatgcagtg atgtcgactc tttgcccacc gccatctcca gctgttgcca | 120 |
| agacagagat tgctttaagt ggcaaatcac ctttattagc agctactttt gcttactggg | 180 |
| acaatattct tggtcctaga gtaaggcaca tttgggctcc aaagacagaa caggtacttc | 240 |
| tcagtgatgg agaaataact tttcttgcca accacactct aaatggagaa atccttcgaa | 300 |
| atgcagagag tggtgctata gatgtaaagt ttttgtctt gtctgaaaag ggagtgatta | 360 |
| ttgtttcatt aatctttgat ggaaactgga tggggatcg cagcacatat ggactatcaa | 420 |
| ttatacttcc acagacagaa cttagtttct acctcccact tcatagagtg tgtgttgata | 480 |
| gattaacaca tataatccgg aaaggaagaa tatggatgca taaggaaaga caagaaaatg | 540 |
| tccagaagat tatcttagaa ggcacagaga gaatggaaga tcagggtcag agtattattc | 600 |
| caatgcttac tggagaagtg attcctgtaa tgggactgct ttcatctatg aaatcacaca | 660 |
| gtgttcctga gaaatagat atagctgata cagtactcca tgatgatgat atttggtgac | 720 |
| agctgtcatg aaaggctttc ttctcaagta ggaattttt cttttcataa agctgggat | 780 |
| gaagccagat tcccatct | 798 |

<210> SEQ ID NO 9
<211> LENGTH: 169
<212> TYPE: DNA
<213> ORGANISM: Homo sapiens

<400> SEQUENCE: 9

| | |
|---|---|
| aaacagcgac aagttccgcc cacgtaaaag atgatgcttg gtgtgtcagc cgtccctgct | 60 |
| gcccggttgc ttctcttttg ggggcggggt ctagcaagag cagatatctc cggagcattt | 120 |
| ggataatgtg acagttggaa tgcggtgatg tcgactcttt gcccaccgc | 169 |

<210> SEQ ID NO 10
<211> LENGTH: 176
<212> TYPE: DNA
<213> ORGANISM: Homo sapiens

<400> SEQUENCE: 10

| | |
|---|---|
| aaaacgtcat cgcacataga aaacagacag acgtaaccta cggtgtcccg ctaggaaaga | 60 |
| gaggtgcgtc aaacagcgac aagttccgcc cacgtaaaag atgacgcttg atatctccgg | 120 |
| agcatttgga taatgtgaca gttggaatgc agtgatgtcg actctttgcc caccgc | 176 |

<210> SEQ ID NO 11
<211> LENGTH: 576
<212> TYPE: DNA
<213> ORGANISM: Homo sapiens

<400> SEQUENCE: 11

| | |
|---|---|
| agtcgctaga ggcgaaagcc cgacacccag cttcggtcag agaaatgaga gggaaagtaa | 60 |

```
aaatgcgtcg agctctgagg agagcccccg cttctacccg cgcctcttcc cggcagccga    120 acccaaaca gccacccgcc aggatgccgc ctcctcactc acccactcgc caccgcctgc    180
gcctccgccg ccgcgggcgc aggcaccgca accgcagccc cgccccgggc ccgccccgg    240 gcccgccccg accacgcccc ggccccggcc ccggccccta gcgcgcgact cctgagttcc    300
agagcttgct acaggctgcg gttgtttccc tccttgtttt cttctggtta atctttatca    360
ggtcttttct tgttcaccct cagcgagtac tgtgagagca agtagtgggg agagagggtg    420
ggaaaaacaa aaacacacac ctcctaaacc cacacctgct cttgctagac cccgccccca    480
aaagagaagc aaccgggcag cagggacggc tgacacacca agcgtcatct tttacgtggg    540
cggaacttgt cgctgtttga cgcacctctc tttcct                             576
```

<210> SEQ ID NO 12
<211> LENGTH: 43
<212> TYPE: DNA
<213> ORGANISM: Artificial sequence
<220> FEATURE:
<223> OTHER INFORMATION: Primer

<400> SEQUENCE: 12
cgactggagc acgaggacac tgaggaaaga gaggtgcgtc aaa                     43

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
tttttttttt tttttttt                                                  18

<210> SEQ ID NO 14
<211> LENGTH: 18
<212> TYPE: DNA
<213> ORGANISM: Artificial sequence
<220> FEATURE:
<223> OTHER INFORMATION: Primer

<400> SEQUENCE: 14
aaagagaagc aaccgggc                                                  18

<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15
cgactggagc acgaggacac tg                                             22

<210> SEQ ID NO 16
<211> LENGTH: 17
<212> TYPE: DNA
<213> ORGANISM: Artificial sequence
<220> FEATURE:
<223> OTHER INFORMATION: Primer

<400> SEQUENCE: 16
cagggacggc tgacaca                                                   17

```
<210> SEQ ID NO 17
<211> LENGTH: 22
<212> TYPE: DNA
<213> ORGANISM: Artificial sequence
<220> FEATURE:
<223> OTHER INFORMATION: Primer

<400> SEQUENCE: 17
gtcaacggat ttggtcgtat tg                                              22

<210> SEQ ID NO 18
<211> LENGTH: 21
<212> TYPE: DNA
<213> ORGANISM: Artificial sequence
<220> FEATURE:
<223> OTHER INFORMATION: Primer

<400> SEQUENCE: 18
tggaagatgg tgatgggatt t                                               21

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
ccttccctga aggttcctcc                                                 20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
gccttactct aggaccaaga                                                 20

<210> SEQ ID NO 21

<400> SEQUENCE: 21

000

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
ggaactcagg agtcgcgcgc                                                 20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
tctggaactc aggagtcgcg                                                 20
```

```
<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
gtagcaagct ctggaactca                                                   20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cctgtagcaa gctctggaac                                                   20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
cagcctgtag caagctctgg                                                   20

<210> SEQ ID NO 27

<400> SEQUENCE: 27

000

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
caaccgcagc ctgtagcaag                                                   20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
aaacaaccgc agcctgtagc                                                   20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
gggaaacaac cgcagcctgt                                                   20
```

```
<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
ggagggaaac aaccgcagcc                                               20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
caaggaggga acaaccgca                                                20

<210> SEQ ID NO 33

<400> SEQUENCE: 33

000

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
tgataaagat taaccagaag                                               20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
acctgataaa gattaaccag                                               20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
aagacctgat aaagattaac                                               20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
caagaaaaga cctgataaag                                               20
```

```
<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
gaacaagaaa agacctgata                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
ggtgaacaag aaaagacctg                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
gctgagggtg aacaagaaaa                                              20

<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
ctcgctgagg gtgaacaaga                                              20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
gtactcgctg agggtgaaca                                              20

<210> SEQ ID NO 43

<400> SEQUENCE: 43

000

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
ctcacagtac tcgctgaggg                                              20
```

<210> SEQ ID NO 45

<400> SEQUENCE: 45

000

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
cttgctctca cagtactcgc                                              20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 47
ctacttgctc tcacagtact                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
ccactacttg ctctcacagt                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49 tcccactac ttgctctcac                                               20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
ctctccccac tacttgctct                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
cctctctccc cactacttgc                                              20

```
<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
ttttgttttt cccaccctct                                                     20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ttaggaggtg tgtgttttg                                                      20

<210> SEQ ID NO 54
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 54
ggtttaggag gtgtgtgttt                                                     20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
gtgggtttag gaggtgtgtg                                                     20

<210> SEQ ID NO 56

<400> SEQUENCE: 56

000

<210> SEQ ID NO 57

<400> SEQUENCE: 57

000

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
agagcaggtg tgggtttagg                                                     20

<210> SEQ ID NO 59
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 59
gcaagagcag gtgtgggttt                                              20

<210> SEQ ID NO 60

<400> SEQUENCE: 60

000

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
ggtctagcaa gagcaggtgt                                              20

<210> SEQ ID NO 62

<400> SEQUENCE: 62

000

<210> SEQ ID NO 63

<400> SEQUENCE: 63

000

<210> SEQ ID NO 64

<400> SEQUENCE: 64

000

<210> SEQ ID NO 65

<400> SEQUENCE: 65

000

<210> SEQ ID NO 66

<400> SEQUENCE: 66

000

<210> SEQ ID NO 67

<400> SEQUENCE: 67

000

<210> SEQ ID NO 68

<400> SEQUENCE: 68

000

<210> SEQ ID NO 69

<400> SEQUENCE: 69

000

<210> SEQ ID NO 70

<400> SEQUENCE: 70

000

<210> SEQ ID NO 71

<400> SEQUENCE: 71

000

<210> SEQ ID NO 72

<400> SEQUENCE: 72

000

<210> SEQ ID NO 73

<400> SEQUENCE: 73

000

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92
<400> SEQUENCE: 92

000

<210> SEQ ID NO 93
<211> LENGTH: 38001
<212> TYPE: DNA
<213> ORGANISM: Mus musculus

<400> SEQUENCE: 93

| | | | | | |
|---|---|---|---|---|---|
| tgtctctagg | taaaattttg | aaggaaaaaa | aaaacactaa | gaaggtatat | tccttcaaag | 60 |
| ttccagtctt | attctgaagt | gtaatgttat | gttagtttga | ctcacagaca | ggttttaaag | 120 |
| aagggcttac | ttcaagagga | caccaaacaa | ataccttcta | ttcctagtgg | gctctggaat | 180 |
| cacagaaaac | tgacccaatc | aattacattg | atagctctgg | cttactacag | acaagcaaat | 240 |
| tatcttaagt | gtgcatgcat | gcgcgtgtat | gtgtgttagt | acctaacacc | cacctgggaa | 300 |
| cttttcagct | tttcagtgtg | ggatatagta | taaacgtcta | ttcctcgtgt | tgtggattag | 360 |
| ctgactggcc | tcactcagct | gccttcctta | cctgcaaact | cacccacttt | gactacagca | 420 |
| tcgcactctt | aaccctagcc | ttccaaacat | ggtcctatgc | tatttctgtg | tgtctggatg | 480 |
| tattttaac | tctcagatgt | atacttcatt | tatgagatat | acatctgaag | accacggtac | 540 |
| aaaacactgt | aagaacttga | tagaatgaca | actgctaggt | aaaaaaaaaa | aaaaaaaaaa | 600 |
| aaaaaaaaaa | aaaaaaagc | atacaatacc | tggtgagagt | tctattttta | ccgaaggtgg | 660 |
| tattgatagg | tattctgtta | ttaatgcctt | tcttttccct | ataaatgatg | aaagttgct | 720 |
| ggaaaataat | aaacactact | catctgtagt | gaaaagccac | aatacagtta | caaaccaatc | 780 |
| aatcaatcaa | taaatcagac | gtcatggtgt | tcttttccca | aaggttaaaa | aacaaagtgc | 840 |
| actgtgctat | ttggcaaaaa | tgacgtttag | aagaaaacac | ggtgactacg | cacagagggt | 900 |
| gggggaatca | ttgtgcttgt | tgcggagtga | acacgtacga | tgtgcacgca | gacttacggc | 960 |
| atttaaccgt | gtcatangga | ccaaaggaaa | tccactcact | cactaaatat | ttgttgagca | 1020 |
| cccactacct | gccaactccc | aaacaaaaca | aagcaaaact | acttacaacc | acaaactacg | 1080 |
| cttcgtaacc | tagatagata | acgcaggtga | cactatctat | ctaggttgag | ctcagctctg | 1140 |
| cccatgcttt | tcctgagcgg | ctcttggaag | aaaagctaca | aagcccatga | cagcctccgc | 1200 |
| ctggccagct | gccactggca | tctcaaggct | ggcaaagcaa | agtgaaagcg | ccaacccgga | 1260 |
| acttacggag | tcccacgagg | gaaccgcggc | gcgtcaagca | gagacgagtt | ccgcccacgt | 1320 |
| gaaagatggc | gtttgtagtg | acagccatcc | caattgccct | ttccttctag | gtggaaagtg | 1380 |
| gtgtctagac | agtccaggga | gggtgtgcga | gggaggtgcg | ttttggttgc | ctcagctcgc | 1440 |
| aacttaactc | cacaacggtg | accaaggaca | aaagaaggaa | acaagactgc | agagatccgc | 1500 |
| accggggagc | cctgcagatt | ctgggtctgc | tgtggactgg | gggcgggact | gcgactgggc | 1560 |
| gggcctgggg | gcgtgtccgg | ggcggggcgg | tcccggggcg | gggcccggag | cgggctgcgg | 1620 |
| ttgcggtccc | tgcgccggcg | gtgaaggcgc | agcagcggcg | agtgggtgag | tgagacgcgc | 1680 |
| gggcggaggg | gggctgctgc | cacggtcggc | tcgcgggccg | gccggctccg | ggtaccagcg | 1740 |
| gggttttttt | ctccttcgag | gtgaactcct | ccctgtcccc | cgggcgaaag | agcccttggc | 1800 |
| cttgcaggag | ttgcggggc | cgcgcggtg | cggaggggat | ggggatgggc | ctcatctttg | 1860 |
| ctgtccgccc | gcgctccccg | atcccgaccc | ggagcgtctc | ccgggccctt | gagggaaccc | 1920 |
| tccgggagta | cggcgagcgc | ggccccacc | gccacaagcc | tgggccccag | gggcctggcc | 1980 |

-continued

```
cggcgacagc tggtgggtcc tgcgacccag tcaggtctcc cgagggtccc cgcccgggag    2040
gagaaagcgc cggtgggatg gagtaaggac ggacagaaca acacgcaggc aggatttcgc    2100
agaagtttgc aaggagtgcg gatgcccact tacatgggct gctactctta ccaggttgtt    2160
ccccagttct gtgggacgtg acctggttgc ctcacagctc cgcggttgta cagacttatt    2220
aaaggaagtg accattgtga cttgggcatc acttgactga tggtaatcag ttgcagagag    2280
agaagtgcac tgattaagtc tgtccacaca gggtctgtct ggccaggagt gcatttgcct    2340
gggagggatt ggttgcgctt tctggtgtgg ggactattag gctcttgtag agttttgtcc    2400
cggcagatgg ataaatttct tgttacactg ttcccgttcg tcaccagttg agaaaaacgg    2460
gtacacagtc tgtctcagta gtacttttac tttatattaa gggcccaaaa gggactggaa    2520
aatactttaa gatagaatcg ttagtccact tggaaaactt aaaatatgag agagagaggg    2580 ggggggaga gagagagaga gagagagaga gaaaggaagg aagaaggagg aagaggagga    2640
ggaaagagat tgagattatg ttaataatat ggaatcagaa tatttgaaat atagtaagcg    2700 tccctcagt taaagaggac attccaggag gcccccagta tagcctgaaa tctcaggaaa    2760
cgcctacata cacccatcgt gtggatatag gtgttttccc ttcattacat ttcatacaca    2820
gatgttaaag tttagaaagt aggcacaata agagattaca aataactgat aataaagtcg    2880
agccattgca gctgctctgt aaaagtcctg tgaatgtgat cgctttgtgt ttcaaagtaa    2940
cttactgtac ttcacccctg ttaagcaaaa caagattcac ctgaacgcag gcaccttggt    3000
accttggcag acaccagatc tgataaccaa gaggatggag aagtagtggc agacagtgtg    3060
gagagcatga atatgctaga caaaagggtg aatcataacc taggagcaga aagcaggtat    3120
ttcatcatcc tccacagtaa aaacctatgt cacgtaaaaa acctacaagt agttttttctt    3180 ttactctttt tgaatgaaag cttgctacag gcactgaaag ttaaaataat ctgtggatca    3240
ggaggaacag gggttttctg tctgagtcac tgctgactag cacctcagtg accattggca    3300
ctgtgggaaa ccccagagtc agttggaaac ttcgaaacta aaggtgacgg tgttcttatt    3360
tcatagaaca caaaaaataa gaggggttac agcctgcgct gcagactgga cattcaacaa    3420
gcatttaaat ttctgggaga caaatgtaaa tataacttta aaagttggta aaatactctg    3480
tttggctatg ttggccatcc aatgtttgct tttagaaaat gactgaatgg ataaaacgtc    3540
tatcttttga gcctgcccta gacccccatg ttgagtgaat actgtccaag tgttaggtta    3600
gccggcctga gaaacttgga tctaggcaag atggcacagt cctggtgtca tgagtatgca    3660
tgtgagtttt ggctgaaatt gaacattgt agagaatgac aaaggctggt ctggcaagta    3720
gtccactgtc tttacagtgg tcttggttag ttcctgtttg gctgagaggg ctggttgatg    3780
gctgtcctgc ccctcttccc acaagtggaa gccttatggt ataattcttg atcacagtag    3840
cagtaggcaa atgaacttcc tcaaagcagc ctggaaagct gatttttttt tctttctttc    3900
tctttttttt tttttttca aaggttaaa gaaaaaacaa agggcttcaa atgtgccagt      3960
ctgctaacag tgttaacatg tttattaaca taaataaact ttattagttt ttggaagtat    4020
tggttaagcc ctcgtgaccc ctgaactcgg tttatagagt gatgagtcgt agcctcactc    4080
tggtttggac tctggcttct ctcagaagac tctgtggcta atgttaacct tctgaagtag    4140
ccagaaaaca tataagcaaa agtctgtgag gttgaaatga atttttggc cacatttgta     4200 tatgggttcc caccaatgct aacttcaggt gttagtaata tcagactcac agcttccctg    4260
attacacttc gctataagac tttattttt aggtcatagg aatttcccct ttttcatgat     4320
```

```
tcctaaatca tgaaataaca tagtctaaaa atacggtatt cctgaaataa acaatttcta    4380
agttttaagc tgcgtgctat tctgaacagt ctgatgccct cttgtagctt ttactgtgtc    4440
ctaccccggg catggttgat tcctttgtcc aaacatctgt ctgttgtatc cacactggat    4500
tgcaccacct gcgtgctagt cagtcactca gacattttag ttataaggta gcttatattt    4560
actccttatt ttatttaata atggcctcat agcaaggcgg taatgatact ggtaatttgg    4620
gtttgcttaa gaggagccat gaagtagttt taaatgaaaa ggtgaaaatt cccactatag    4680
tttggagggg gaggctatac tggtactact acgattcacg gtaagactaa atcttctgtg    4740
aaattatgaa ggagaaaaag ttacactggt ctggtcttgc tgttggatta attttatagt    4800
tataaccact gtacatgata aataacccta aaacaatgaa tttgtaggtg gatggcataa    4860
tctgaaaacc atgttctgag cagttgatgg cagcaggctg tgctggaagt gttaggcata    4920
tttatagatt tcagcccaag ttctgaagag gctggagaga tggctcagtg gttaagagtg    4980
cttgctattg cagaggacct aggttcctct acaggcacca ggcaagcgtg ggacacactg    5040
agatacatac agacaaaaca taaaattaaa taaattgtgc ataataatac tagtaatata    5100
tgagtaaaat aaggataaat acacatcata attaaataaa taaattgtaa agttccctag    5160
aagtgagggt caccaagcca ttcacaagat ggctgcgctg atgcagggat atatgtgaac    5220
tagaaaaagg tcaaacttaa cagagaagtt ccaaggcatg ctactgcagg cttggctagc    5280
atgcttgacc tgcagaaatg ctgacggcca ctgggaggtt ttcacaaatg aggaattaga    5340
agaacttttt ttactaatct ccagaaaaaa aaagggaag aagaaactga agcagcctgt    5400
gatgtggacc agaaacgcag tgacagtaac atgtgtgaca ttgcaaaggc atgaaaggac    5460
agagctgtgg aatacagacc tcaggtggag ctcagcatag agtcattcgg ggattatgcc    5520
tgctgcagca acaaaaggat gagctcaaaa gagacaccga cttctgaatg cagtgggtgt    5580
ttgttttgtt ttgtttcaaa tgaattgggc agaaaacttt ccagctgtgg aagcttctga    5640
accgtccctt gctgctgaca tctaagcgtc cgctgtgtcc cagctcagtg atctagggtc    5700
ttccaaacag atggtccggt gctgagcact ttgaatctca atcctgagtt tctaccacgc    5760
ctttggccat ttaattccca gataaaagac acatacaacc tttatattta aataaaacct    5820
tagtcagcac aagagctgag caaatatctg tcctctatgc tattatatct attacccagc    5880
caataacccc attctataat ttgctgtgct tcatctgggc tgctcttaac ttcagtcagc    5940
cagcccacgt ggccattatt ttaagatttt tttacccat agtgtcttct cactttactt    6000
tacattttc tctctctcct catggttctc ctctgacccc aagcctagga accctaaacc    6060
ccacccatgt ctcttctgcc catctattgg ctgtaggcat ctttattcac caatcaggat    6120
aacttggagg caaggttaag tagtctcctg ggtctaggtg ctgtctctgg gagcaaccag    6180
tatttagcat agcaaaagac cagacctcca caatgatcac tctgaccatc ggggcagaag    6240
gcacctacta gcctgtgcca ctcacctcac tttgttgaat cacatcttat cctgtagtgt    6300
gtatcactgc ctgttatcac aggaaaaagt gagtcccatc aaataagatg tttcagaaag    6360
agaccatgtt catataatta tcattctggt aagcttttaa tggttatatt ttgttattaa    6420
tctctttgtt cctattttgc aaattatacc ttacagtaaa tatatatgca tccaatgggg    6480
tctttgaatt cctccccggg gagtaggagg actctttgag gatgggctgc atttaaagct    6540
aaacaacgca acatgacctt tagtccttat agatagccta gagatgagac taaataaaag    6600
aaatggtata taatgcttta gtttcccaa tcagcttaaa agcttttcct ataaatcttt    6660
aagattatgc tctggggctc aatactgctt caagaagggc ttttctttg tatttagaat    6720
```

```
tattcacctt tttaaacaaa aggagaaaat ggaatagaaa tatgtttgca acataatttt   6780
atgactatgt gtttatttcg cgtgttctgt gggcctgcag tttgctgctg ttaatgagga   6840
caacagtggc accaatacag tttccactca gattacattc tctgttccct ttctgaaagc   6900
tgccctctcc actgggccca aaagagtcag tatcttaaac aagctgtaca acttagataa   6960
ccatggtctc ttcagactag ttaattgaca tatattaaaa agtaaatagt accaaagtga   7020
atttctgaaa ttaaaaatga acatttaaaa actctaggta aactattcct tagagttaag   7080
tgttttgcca agttctgtaa tcataatatg atagaaacgc tcactcagca ttctaaatat   7140
agaagttact ccttcgcatg acactctaat tcttgataag gtggagaaag agagagagag   7200 aggggagag acagaaaata tggtggttca aggaccattt gagggaatta gttatgttct     7260
tccgtcctct gtggatctta ggggttgaat acagtcattg agctcggtgg atggctgtcc   7320
tgttgaaagg tctgcccagc agagcaaata gactttttta tttacatgga catccgtttg   7380
tgactaatct aatgttcact cccaaagtaa tcacacagac agagaggtag cttccttcag   7440
tactcttacc ttacatgaat cctaccattt tgttatttt tttccacttt aaatctttga     7500
ttatgtgttt ttaattagaa aatttgcata caaatttcca tacagtatgt agaattgact   7560
gtgtttgaat gggtgaagat ccacatgtgt aaccctagct ctggactggc tctgagcttg   7620
tttgctcttc tcttttgtgt tctgagtaac tgaaactctt tcattttagc agcttagtat   7680
gcgcccttca cattgctgtg ctgcctgctg cactaacatt actcctttgc ttatgttccc   7740
cttcctgatt cagtgtcatt ttaagcagta gtactggacc tcagtaccct agccggagct   7800
cactgaggtg acagggctga ggctctgctg ctgtcttttg agcttacctc tttttaatgt   7860
tttatggtat ttctgctgcc aggttttgggg gttttgtttt gttttgtttt ttgtttttg   7920 ttttttttaa ttttctagga acacctagaa aacacaaact aggaaactta aaagagcagc   7980
gtcttgttcc ctgcgttcta gaaagtccaa gcctaatgcc agtgtcatgg ttgtcaggaa   8040
catgagcctc tgaaggcttc ttgggaaacc tttcttgtct caacacctct ggtggcaagc   8100
agtagtccat ggtactctct ctgtccacgg tcagcatccc agtccctgcc ctttatcttt   8160
gtgcagccga ccagctttgc tttagtctgt ctccttctca ggtctccttc cccgctcctc   8220
ttaagcacag cagtcattgg attagagccc atccttccct cggatggccc atttgaccta   8280
attttacgta tttgtaacta aggtcccatt tacttacaca gggccctccc cttcctgttt   8340
tgttctttag ctgaaatggt ttggagacca aatatccaat cattacaatt gtgcacaagc   8400
tatgttcatt tggaggtaat aaaggctcat tctttgcttc tattggtatg tgacattttt   8460
ctaagtcact tggggtttga tagatatctt taaatggctg aacctgatca ctgttctttt   8520
gtatgtccct gtttagctat tgcaagcgtt cggataatgt gagacctgga atgcagtgag   8580
acctgggatg cagggatgtc gactatctgc cccccaccat ctcctgctgt tgccaagaca   8640
gagattgctt taagtggtga atcacccttg ttggcggcta cctttgctta ctgggataat   8700
attcttggtc ctagagtaag gcatatttgg gctccaaaga cagaccaagt gcttctcagt   8760
gatggagaaa taacttttct tgccaaccac actctaaatg gagaaattct tcgaaatgca   8820
gagagtgggc ctatagatgt aaaatttttt gtcttatctg aaaaagggt aattattgtt      8880 tcattaatct tcgacggaaa ctggaatgga gatcggagca cttatggact atcaattata   8940
ctgccgcaga cagagctgag cttctacctc ccacttcaca gagtgtgtgt tgacaggcta   9000
acacacatta ttcgaaaagg aagaatatgg atgcataagg taagggggctt ttgagcttga   9060
```

```
tcatggtagc ctggccaatg aaagttttt  tctggtacag ttacacttaa gttttggaaa   9120
ttatatgctg ctaacaccag acagctgtta tgttgtgtct cctgggcaca gaaagccctg   9180
ctctcatgcc tggggtcttc acagtcctaa tggaaagtaa gatcttataa acattgtgtc   9240
tgagtttgtt ctggaagctg tgactctacc ttcttgtttt cctttccctg tgtgactttg   9300
tcctttgctt acaacagtgc aaaagtataa atattctcag attttgataa gctgtcagcc   9360
acacagcctt agtaactaag ctgctgtccc acgctcccag ttctgtataa cgaggatgga   9420
ccaattagat tctaaggagt tattccttc  aatttgcaaa tttagctaaa ggaaatattg    9480
ttttctcctg atatttacat tgcttttcat tttcagcata tctaaagaac aaacctaatt   9540
ctccttccta ctttctagtt taatataatc ctaaaaatcc attaaaacat gactaattct   9600
ataaggcctc taacctacaa agggaagtag cattttgaaa agaatagttt tctctattat   9660
acctattcat gcagacttcc ttccttattt ctgacatact taacaaaaat catttagatt   9720
caaacagttt agctgcaggt gatattacag acaagtaatc ccagtgctct atctagtctg   9780
aggcaaaagg atttgagctc agtgccagcc tgttctatct acctggtgag ttccagtccc   9840
ataaataaac aaactaaaac aaccgttcct ctgttcctca gatgcgagtc gatcttgttt   9900
gatttaaata gtgtgtaatt attttctttt gaagctgcag gtgttatgtg ggctgtttta   9960
gactaaattc tctctttact gtggagtaaa gggtgctgtg attgtatttc atgttctctg  10020
cgagagcttg aacttgttgg gctaatcgct tgtctccatc ctgtctcccc acctgcgtaa  10080
aaagtatttt cctgtgagct gtacatgata gagcatatct acattgaaaa atgaacgagc  10140
atcaaaatgg atttgttaaa gtaaattttc tttttcttag gaaagacaag aaaatgtcca  10200
gaaaattgtc ttggaaggca cagagaggat ggaagatcag gtacagtgca tatcacatgc  10260
tgcctgtggc aggtcctctt tgcttatgtc ggtataaagt tggtgggtac ttctggtaag  10320
gacctgagga tacattcatt tgacggaagg agcctgaaaa tgagtattct tgttaagctg  10380
tatagaatga actgaataaa aatttctgca gcctaagttt gaattttaaa aaaatttaat  10440
tacatctaca aattagtatt tggccaccct ttttcaatca gcaagaatat gtttgaggtc  10500
atttatttgt agtaaaattg catgcagttt atttatttta ttgaaaatag gtttttttaaa 10560 ctatattttc tgattatggt tttccctcct ctgaatcctc ctagaacctc cacctaccca  10620
aatctatatc tgttctttct ctctctcatt aggatacaat caggcatgta aaataatagt  10680
agtagtagta gtaataataa tgtaaaataa gttaaagtaa aaacaaacca gagtaggaca  10740
acataaatag aagtagaaaa gagccaaata agaaattcaa gaaacacata tagacacaga  10800
cacaatattt gcatacacag aaattgcata aaaccgcaag actggaaacc ataatatgta  10860
tgtaaggtgg agtgggaagc cctgacagca cagtgagtaa agcactttca aaaacaccac  10920
tgactttgtg ttgtgttgcc tgtctgctgg gcatgaggcc tggccttaga gagtggtgtg  10980
tatacccagg aagacttaca taaacactta gcttttcatt tgtgacctga tagcaattgg  11040
aaatagtgtc tgggctaggc attccggctt attgccactt cccctcagca ctgaggcccc  11100
atctgaatcg gatccgtgca acccttgtgc atatgcagtt ttaaaagtta tcccttctgc  11160
aactatgctc acaggagttg ccgtcttaag ggagtgagca caccctgag gcatggctcc   11220 aggggtgcag agccagccat aggcacagtt ttttttaaaa ggtttatgtt gtagttttga  11280
aactcaaatt tatgtgtatt tgtggcagat tgtttgaatg ttgaaatttg ccagtaacat  11340
cttttatctt cttcccttta gcctggcatg ccacccaccc tcatttgtcc ttgtcaaact  11400
ccagtaatta aacatggcta tgtggccttt tctctcattt tccttagcat ggctaaggag  11460
```

```
aatgggactt aaaaaataat aatcatcatt ttaagtatgt ctgagggttt gaggatatag   11520
tggtagaata tctgcctagc ttccatagct tgatcctaca tttgatccct ggcaaaacac   11580
acacacacac acatatacac acacataaaa tgacttttat aaagttagtg tgctgtgctg   11640
tgatgaacag tgccatagga aatattcttg gaaaagacct gaaactaaat gctctaaaag   11700
gtctaatctt tacttgcttg ctgatcgtta agcagagtct ccaagtataa agtcactttc   11760
accaacctct gcactggatt tctggagtaa ttagggagag tcatttcaat ataagaaaat   11820
ttagtaccaa ataaaatttt cattcagtga aattttgttt ttgaaagtaa gagcccactg   11880
tggtggtttg aatatgcttg gcccagggag tgtcctgtaa gattttttgtt gttgttgaac   11940 tccattgaga cttatgttga caataaatgc ctgagagtcc atgtctaaaa tgctgtacct   12000
gtctgaaccc aacggagata aaacttacca tttctgaaaa ggatgaggtg tttatttac    12060 atagctgatg taatgtgctt gcaacagctc tattatgaat cttaatacta cttcagtata   12120
tcacagcact tcaggaaatt taacatacat tgtttaattc catgtcttaa ttgtatttgt   12180
aaacagacat ttcagcagtt actctaaaaa gtagaaataa tgagtggttg cttctggtca   12240
ttaggatgaa atattgaaat gataaaattt tctgggctgg agagatggct cagaggttaa   12300
gagcactgac tgctcttcca gagatcctga gttcaattcc cagcaaccac atggtagctc   12360
acaaccatct gtaatgggga tctgatgccc tcttctggtg tgtctgaaga caactacagt   12420
gaactcatac aaataaaaat aaataaatct tttttttaaaa atctatatct gcataggcat   12480
ttctagatta ggataaattt tccaaaggaa ataagcacct ccatgataag ggcattggaa   12540
atgaagcccc cgcccccacc cccggtctgc acgtgtgttg aggatgagat ctagggcctc   12600
cttatacatg ccaggcagct gttctgtcac caagtggaat ataatcctca acccttaatt   12660
tgaggttcta actttaaaat agatgtgagg ggtttaaata atcatttcat gaaacttaaa   12720
tgagcaagtt tattactgag gtgagtataa gtaattgata attttaaata tatttagctg   12780
agattgatag acacttggca atgtcagcat cttatttagg tgatcataaa ctgatgggag   12840
aaatggtaaa tgttaggggg tgtcgctcat gtcacacacc gcagttatgc tgcaaacaag   12900
atgccgggaa atagaaattc aaggtcttgt tttgcgggtg cagactcttc tgtctcactg   12960
attctatgtg gtaacttcag tatgcatttg gatagattat gtcccatttt gaatgtggaa   13020
gctggctgtt gagaggagac ttcctggtga attccttttt ctaagcatta ccatctgtct   13080
tagtcagggt ttctattcct gcacaaacat tatgaccaag aagcacttgg ggaggaaagg   13140
gtttattcag cttacacttc cacactgctg ttcatcacca aggaagtcag gactggaact   13200
taagcaggtc aggaagcagg agctgatgca gaggccacgg agggatgttc tttactggct   13260
tgcttccctg gcttgctcag cctgctgtct tatagaaccc aagactacta gcctagggat   13320
ggcaccaccc acaatgggcc ctcccccctt gatcactaat tgagaaaatg ccccacagct   13380
ggatctcatg gaggcatttc ctcaactgaa actcctttct ctgtgataac tccagcctgt   13440
gtcaagttga cacacaaaac cagccagtac aacatctttt cacatttaat ttttctcact   13500
ttaaacgtgg cctttaacaa gcgcttataa aaatgcttaa gcttaaatgt tatttaagct   13560
taatatactt aatatacagc actgtagctt aaatgttgca tgtgagagta tatgataagc   13620
catgctcacc aaggaaaaga agcttaaaga gcataaaaac cctgacagcg gtttctgagt   13680
gggaggctcg gggactgtgc tgagcaattc caaccaaggg tgttttactc tctgcctcca   13740
tttgaaatgt ttttcctgca caacctaccc accctgtgat ttcgttcact cgattatgtt   13800
```

```
tgatctaggg tcagagtatc attcccatgc ttactgggga agtcattcct gtaatggagc    13860
tgcttgcatc tatgaaatcc cacagtgttc ctgaagacat tgatgtaagt gtcatgtatc    13920
ttttatgggt tcccttgagt ggtgagtggg tggatgtgtg gtgcatgtgc gtgtgtgtgc    13980
ttgcatactg ggaattgaac ccaagtcctc aggaagagca gccggtgctc ttaagcactg    14040
agccatctct tcagaacctc ttccaccagt ttctttgacc atttgttgag aatattccag    14100
tcacacattt tccgtgagta aatctctcta atgctgattt gtcattaagc tcagtctcct    14160
aattctgata gctaagaagg gtaaattatt aaaaagtgcc ctttactctt cctggccaat    14220 tccccttttgt tcttctgaaa agtgcataga cagcatcact ttatagatca ccttgatgct    14280
cgtgagaggg ctggctcgtg ctggctctag acttcggcac acttattaag agttctccca    14340
acactgtaaa cagactaatt tttatattgt gcattttaga tagctgatac agtgctcaat    14400
gatgatgaca ttggtgacag ctgtcacgaa ggctttcttc tcaagtaaga atttttacttc    14460 tttttctgaa tgctaagtaa agcagattaa aaatcttaat gctcacccat gacaagattt    14520
acagggaaaa gatggtagaa aacctacttc ctccaattat ttagggtcaa catggcacat    14580
ttgagcttac acgtgttgtt ctcacccata caacagtggc atatctgaca ttactcttcc    14640
cacagtctaa aaaggcagag tttccgtagt acccagggaa gttctggtct gtgtttgggt    14700
ctggtttctt ctttcaattc tcactaagta taaccctttag gaatctatca agttgagttg    14760
cattttaaat tcctgtgaat tcttcaggtc tagaaatgga aatcattcat attttagact    14820 gacattttc atcttcttgt gtaatttaac atttaagaac ttgagctcta atatcagact    14880
gtctaggtta caactgggaa aacttggtga agctacccaa agctgaacct ccattttctt    14940
acctgtgaaa tgtgaacagt gataacagct agtttcttgg gtccttgtag gcaccaaatg    15000
acaggataat ataagcacc taggacagtg gagccaatga gccaggagcc agtgtgccct    15060
attatatctg ctctaagaaa gacagtaagt ggaatagcca atactgactg tcttagtcag    15120
gctttctatt cctgaacaaa aaacatcatg accaagaagc aagctgggga ggaaagggtt    15180
tattcagctt acacttccac gttgctgttc ctcaccaaag gaagtcagga ctggaactca    15240
gatcaggaaa caggagcaga tgcagaggcc atggaggaat gttacttact agcttgcttt    15300
cttatagacc ccaagactac cagcccagag atggtcccac ccacaaggga ccctgccccc    15360
ttgatcacta attgagaaaa tgccccacag ctggatctca tggaggcatt tccccaactg    15420
aaactccttt ctctatgata actccagcct gtttcaagtt gacacaaaac cagccagtac    15480
gctgaccgag cagctgtgtg ttcctctgca gggctgtgtt ctctgtttgt ccctcatctc    15540
ctgttgtagt ctcctttaca gttacagact gtcatcagta acgagagaga agtgaatagg    15600
attttgttaa agtgtttact tctatgtcac attcccttcc tataataagc tcacagtgaa    15660
ataccaggtg accgtgctta acggcatcta ttacctaact ggggtatctt tttccttaaa    15720
atggatttaa ttttatgtgt gtttgaatac ctgcatatgt gtatgtacac catatttatg    15780
tatgcctggt acctgaaaaa gggaaaagag ggctttggct ttcttgaaac tagatggttg    15840
tgagtctcca tgtgggttct ggattgtctc tgcaagagcg gcaggcacac tttagcagtg    15900
agccgctcct gtcccgagtt gtcttaagac ctgtgaaagg tccctaaaaa atgcagggtt    15960
ttacccgaat aaaagatgac atcatgcaga tggctttggt gttcatcaag ctcttgtgtg    16020
ttgtcctaac cttgctgggc tttgtcgttg tgaagctgta actccgtcaa tgttttcctt    16080
acctacagtg ccatcagctc acacctgcag acctgtggct gttccgttgt agttggcagc    16140
agtgcagaga aagtaaataa ggtaattcgt tctacagttg aacatgatct gacttttatc    16200
```

```
atcactagca tatcatacat tatcatctaa acagtaggct gcaattgaaa taaccccata    16260
gtataaggaa gcaatgtaat tttaccaaat ttctctgaca ccctctagca gaactgactc    16320
taatagaatg agtaagaatt caattaccaa attaattttg atactctttt ttatttttgt    16380
tattactttt ttattttatt ttaattaggt attttcttca tttacatttc caatgctatc    16440
ccaaaagttt cccatacact cccacccact cccactcccc tatccaccca ctcccctttg    16500
gccttggcgt tcacctgtac tgagacatat aaaatttgca agaccaatgg gcctctcttt    16560
ccaatgatgg ccaactagac catcttctga tacatatgca gctagagaca cgagctccag    16620
ggggtactgg ttagttcata ttgttgttcc acctaaaggg ttgcagaccc ctttagctcc    16680
ttaggtactt tctctagctc ctccattggg ggccctgtga tccatccaat agctgactgt    16740
gagcatccac ttctctgttt gctaggcccc agcatagcct cacaagagac agctatatca    16800
gggtcctttt agcaaaatct tgctagtgtg tgcaatggtg tcagcgtttg gaagctgatt    16860
atgagatgga tccccaggat ggcagtatct agatcgtcca tcctttcgtc tcagttccaa    16920
actttgtctc tgtaactcct tccatggtgt gttttgttcc aattctaaga agggacaaag    16980
tgtccacact ttggttttca ttcttcttga atttcatgtg ttttgcaaat tgtatcttat    17040
atcttgggta tcctaagttt ctgggctaat atccacttat cagtgagtac atattgtgtg    17100
agttcctttg tgattgggtt acctcactca ggatgatgcc ctccaagtcc atccatttgc    17160
ctaggaattt cataaattca ttctttttaa tagctgagta gtactccatt gtataaatgt    17220
accacatttt ctgtatccat tcctctgttg aaggacatct gggttctttc cagcttctgg    17280
ctattataaa taaggctgct atgaacatag tggagcatgt gaccttctta ccggttggaa    17340
catcttctgg atatatgccc aggagaggta ttgtgggatc ctccggtagt actatgtcca    17400
attttctgag gaacggccag actgatttcc agagtggttg tacaagcttg caattccacg    17460
aacaatggag gagtattcct atttctccac atcctcgcca gcatctgctg tcacctgaat    17520
ttttcatcgt agccattctg actggtgtga ggtggaatct cagggttgtt ttgatttgca    17580
tttacctgat gattaaggat gctgagtttt tttttcaggt gcttctctgc cattcggtat    17640
tcctcaggtg agaattcttg gtttagctct gagccccatt tttaatgggg ttatttgatt    17700
ttctggagtc caccttcttg agttcttat atatattgga tattagtccc ctatctgatt    17760
taggataggt aaagatcctt tccaaatctg ttggtgacct ttttgtctta ttgatggtgt    17820
cttttgcctt acagaagctt tgcaatttta tgaggtacca tttgtcgatt ctcgctctta    17880
cagcacaagc cattgatgtt ctattcagga atttttcccc tgagccaata tcttcgaggc    17940
tgttccccac tctctcctct ataagcttca ctgtctctgg ttttatgtgg agttccttga    18000
tccacatgga tttgacatta gtacaaggaa ataggaatgg attaatttgc attcttctac    18060
atgatatccg ccagttgtgc tagcaccatt tgttgaaaat gcttttttcc actggatggt    18120
tttagctccc ttgtcaaaga tcaagtgacc ataggtgtgt gggttcattt ctgggtcttc    18180
aattctattc cattggtcta cttgtctgta tataccacta ccatgcagtt tttatcacaa    18240
ttgccctgta gtacagcttt aggtcaggca tggtgattcc accagaggat cttttatcct    18300
tgagaagagt ttttgctatc ctaggttttt tgttattcca gatgaatttg catattgccc    18360
tttctaattc gttgaagaat tgagttggaa ttttgatggg gattgcattg aatctgtaga    18420
ttgcttttgg caagatagcc attttttacaa tgttgatcct gccaatccat gagcatggga    18480
gatctttcca tcttctgaga tcttctttaa tttctttctt cagagacttt aagttcttgt    18540
```

```
catacagatc tttcacttcc ttagagtcac gccaaggtat tttatattat ttgtgactat   18600
tgagaagggt gttgttttcc taatttcttt ctcagcctgt ttatcctttg tatagagaaa   18660
ggccattact tgtttgagtt aattttatat ccagctactt cattgaagct gtttatcaga   18720
tttaggagtt ctctggtgga attcttaggg tcacttatat atactaccat atcatctgca   18780
aaaagtgata ttttgacttc ttcctttcca atttgtatcc ccttgatctc ctcttgttat   18840
cgaattgctc tggctaagac ttcaagtaca gtgttaata gggaggaaga aagtggacag    18900
ccttgtctag tccctgattt tagtggggtt gcttccagct tctcaccatt tactttgatg   18960
ttggctactg gtttgctgta gattgctttt atcatgttta ggtatgggcc ttgaattcct   19020
gatctttcca agacttttat catgaatggg tgttggattt tgacaaatgc tttctcctca   19080
tctaacgaga tgatcatgtg gtttttgtct ttgagtttat ataatggatt acattgatgg   19140
atttccgtat attgaaccat ctctgcatcc ctggaataaa acctacttgg tcaggatgga   19200
tgattgtttt gatgagttct tggattcagt tagtgagaat tttactgagt attttgcat    19260
caatattcat aagggaaatt ggtctgaagt tctctatctt tgttggttct ttctgtggtt   19320
taggtatcag agtaattgtg gcttcataga atgagttggg tagagtacct tctgcttctg   19380
ttttgtggaa tagtttgtga agaactggaa ttagatcttc tttgaaggtc tgatagaact   19440
ctgcactaaa cccatctggt cctgggattt ttttggttg ggagactatt aatgactgct     19500
tctatttctt taggggatat aggactgttt agatcattaa cctgatcttg atttaacttt   19560
ggtacctggt atctgtctag aaacttgtcc atttcatcca ggttctccag ttttgttgag   19620
tatagccttt tgtagaagga tctgatgtg ttttggattt cttcaggatc tgttgttatg    19680
tctccctttt catttctgat tttgttaatt agaatacttt ccctgtggcc tctagtgagt   19740
ctggctaagg gttatctat cttgttgatt ttctctaaga accagctcct tgattggttg    19800
attctttgaa tagttcttct tgtttccact tggttgattt caccccctgag tttgattgtt   19860
tcctgccgtc tactcctctt gggtgaattt gcttcttttt gttctagagc ttttaggtgt   19920
gttgtcaagc tgctaatgtg tgctctctct agtttccttt tggaggcact cagagctatg   19980
agttttcccc ttagaaatgc tatcattgtg tcccataagt ttgggtatgt agtggcttca   20040
ttttcattaa actccaaaaa gtccttaatt tctttcttca ttccttcctt gaccaaggta    20100
tcattgagaa gactgttgtt cagtttccac gtgaatgttg gctttctatt atttattttg   20160
ttattgaaga tcagccttag tccatggtga tctgatagga tgcatgggac aatttcaata   20220
tttttgtata tgttgaggct tgttttttctg accaattatg tggtcaattt tggagaaggt  20280
accatgaggt gctgagaaga aggtatatcc ttttgttta ggataaaatg ttctgtagat    20340
atctgtcaga tccatttgtt tcattacttc tgttagtttc actgtgtccc tgtttagttt   20400
ctgtttccac gatctgtcca ttggtgaaag tggccatctt tatagtcact gaagacatac   20460
aaatacatat tcatatcaac tggaacaaac ctaatttctt tttaaatgtt ttacatggaa   20520
ataagttagg ggttgttatt tgcattacaa agttactcat ccctttcctt cttttctttt   20580
tttttttttt tttttttttg agaacaagcc tgtgtactta tatgaacttt aatttgccaa   20640
attcataatt cttattcaat catttatgac agaatgctaa aactctcatt atattttagc   20700
taggcattta gagctgttat gtgtaacccc aaaaagtagc tttccacttg agatgctgaa   20760
ggccttgggt tccgtgggct gtcatcatgg ttggctgtat gaaaagagaa aggctccatt   20820
gtttgggcat cacttaaata tttttcacc tttcatcttc ttttaggtta agtagcttgt     20880
ccttgatcat ttcatttttg agagacaact tgccactact ctagttgaaa agtgctgtct   20940
```

```
tgacgctgtc tctggctgtg gtcagagtcc agcagagctg cacagctggt tacctttctc   21000
tgtacagctc taggccaact cttcttactg gcgaccattt ctaaatccac cattcacttg   21060
ttccccatga aagtgagtag ggttttttct gtggaagatt ttgggcagtc ctgttgccac   21120
tttgcatcag acaatagttc cctcattgaa acacgcagtt tattctccag agcggtctgc   21180
ccactccaaa ggcagtaggt gctgggtaga gatatgccaa gtatcacact aggctatgac   21240
tgctcactca gatcactcgg atgaagcttt catggccaaa tacagttgag aaagaacaaa   21300
tattcttcac ttagagagca acaagagtta ttcaagtgta acaagttctg agattccatg   21360
cagttgattt accagctact tcctaaactt aactggccac aaaatcccct tgtaagcagt   21420
atgttgtttt gacccatgcc ctgtcaaagg atactcctta cttgggaact gttttaatga   21480
tggcaacaaa aatttctatt taaatttatt tcataagcaa gcaaagatct ttttacttca   21540
cattccaatg ttgactcttt tcctctagat agtaagaacg ctgtgccttt ttctgacacc   21600
agcagagagg aaatgctcca ggctgtgtga agcagaatcg tcctttaagt acgaatcggg   21660
actctttgtg caaggcttgc taaaggtaca cttgccgatc atttatcatg tgtgacgcaa   21720
caagtagaga tggagggtac aaataatcac tgagaggctt tggaaagtat attgttagca   21780
tttaatgtct catagtttta gttgtctggg tactggtttg ttttcatcat tctgagcatg   21840
aagtgtatgt cttagggatt tatagttcgt atcatgtatg aaacaccatg gggtaatatt   21900
tatatttcac ttggttccct ctagctatgt gtctggcccc agtgctttcc ttgtaaatgc   21960
atgcttgaat cagactgagc tgatatgata atgttgatgc tccttttgct tactgagtgg   22020
ctatgaatat gcaccatact tactcattgt aagaaattaa aatgtctctt aaggatgtaa   22080
acatagcaaa atgaagcaaa acaaaagcga tgctgtttta ggtaccctaa ctgaccttgt   22140
gtattcaagg agcattccta cttctgtgat gcaaaagctg tctacactgg gcagatctac   22200
aaccagcatt aaaccaaata gggaatcact gaaatcacgt tatcaaagat gagaaacaag   22260
ataataatgt ctactttcac ggcttttatt caggtctagt gctataagtt tttgccaaaa   22320
caaaaatgaa aacatagact ctgggctgag gctttccctt agcagaaaag tgcttacttg   22380
ttgtgtccgg ccagcagatc acagcctggg ttctagcctg gaaaggcatt ttggaaacct   22440
ggaagagaag aggggctagg taacgagaga aagaacggag ccaagtcaaa agcaactctg   22500
atcaaagctc aattttacta tatcagcacg cagttataaa ggaggggaag gggggggccaa   22560
tagcaaggcg gcaggttcca gcagtgggcg tggcagaccg attgagccgg caagctcctt   22620
ccaggtgtaa acagtggagc cctaaggctg ggggagggga ggctacactt agcatgcctg   22680
atgccctaga tgccacctaa atgacaaatc cagtccagta caggatgtag agcaccccc   22740
cccaaaaaat tatttttttt gtataccaga aatgaaattg ctgagaaaaa aaatgaaga   22800
ccataattat actcccagta gctacaaact aaacagcccc atagatgaag tgagtgatgt   22860
ctgctgtgac aattatgaaa tgaaagaagt aaagatgaac aaatgaaggg aagacatcca   22920
gtactcagga ctgaaagact gctgctaaaa tgcctatcca acccagagct ctctgcagac   22980
tctggacaga tccgctctag atgtgaagat ggtctttttt tttttttttt ttttttggtt   23040
tttcgagaca gggtttctct gtgtagccct ggctgtccag gaactcactc tgtagaccag   23100
gctggcctcg aactcagaaa tccgcctgcc tctgcctccc gagtgctggg attaaaggcg   23160
tgcaccacca tacctggctt tttgtgaaga tgttcttaac agaactagaa agaagtaccc   23220
cttggtttgc tgcccttctg atgcagtatc cccaaaggct cgcatgcact gaacatttca   23280
```

```
tcttacctgg tgccactgtt gggaagtgat ggaaatgcga ggaattgtag cctcgttgag    23340
atgtttctca ttaaggcact gggggcatac ctatggagca tacagtagga acctggtttg    23400
caacctctcc cctctccatc caggctctcc cctgtgcacc tggccttggt gttctgccac    23460
tccatgaacc caaagtaaag tggactatgc ccttagactg taacagtgag tcagaagaaa    23520
catttcctct ttaaagctga gttttctggg tgctttgtca tgttaatgga gtctgattag    23580
tacagaccct gagtaggcag ggcaatctta tgcagaaaca tcaaagctgg tagcatagac    23640
atacctaatt tcacaataga cactgatgga ctcagtctgg agtacttaca gtaagaatat    23700
acagcagaga tacggagctc tcttacagtg gtgctctggg agaactggcc gtcctgtgaa    23760
gaaaagccag agtggctcat tctcaccaga cacaaactga gctcataaga cgcttgaacc    23820
tgagatcctg gtcagcagcc actagaagaa aacttaggag aaaccattca acacgtcagt    23880
ctggggaaaa gggtggtttt ggttttggtt ttggtttttt agtatattcc ccaaatcaaa    23940
aacaacaaaa cccaaacttg acagatgaca tcacactgca aagcttttgc acaaccaaga    24000
aagcaacctg cagagtgcag taataaccca cagaaggaga ggagatactt gtgggcagtt    24060
catcacacag gtcaatataa gcaagtactg atagtgtggc catctccaaa gaagatatga    24120
aaataactgg tatatatgaa gtagtactta gcattgctgc gtatatggta aattcaaaac    24180
catgatgaga tattgcccca cttagatgga tattatcaaa acaacatcaa aaagtgacaa    24240
atgctttcaa ggatatgggg aaagtgtact tgcaggaatt taaattatta atttgccatt    24300
caagaggata ggatggcagt ttaaattaaa aaactagaag tggtagagca gtcgcctaga    24360
acatacaagg ttcagcacta taataaatga gcaattagac atttgaagca acaatctcac    24420
cactaggcaa gtcctaaaag aaatggactc gcttcttctt cttcgggaaa acaccaaatg    24480
gcagatgacg ccggtgcagc gggagggccc agaggacctg ggggctcagg attaggaggc    24540
cgcggcggct tccacggagg attcggcagc ggtcttaggg gccgtggtcg tggccgaggc    24600
cgtggccgtg gtcgaggccg cggggctcgt ggaggtaaag ctgaagacaa ggagtggatc    24660
cccgtcacca agctgggccg cctggttaag gacatgaaga tcaagtcctt ggaggagatc    24720
tacctgttct ccctgcgcat taaggagtct gagatcattg atttcttcct gggtgcgtcc    24780
ctaaaggatg aggttctgaa aatcatgcca gtgcagaagc agactcgggc tggccagcgg    24840
accaggttca aggctttcgt cgctattggg gactacaatg gtcacgttgg tcttggtgtt    24900
aagtgctcca aggaggttgc tactgccatc cgagggccca tcatcttggc caagctttcc    24960
atcgtccctg tgcggagagg ctactggggg aacaagattg gcaagcccca cactgttcca    25020
tgcaaggtga caggccgctg tggctctgtg ctggtgcgtc tcatccctgc ccccagaggc    25080
actggcattg tctctgctcc tgaagctcct gatgatggcc ggtatagatg actgctacac    25140
ttcagccaga ggctgcactg ccaccctggg caactttgct aaggccacct ttgatgccat    25200
ctccaagact tacagctacc tgaccccccga cctctggaaa gagactgtct tcaccaagtc    25260
tccttatcag gaattcacgg atcatcttgt gaaaacccac accagagtct ctgttcagag    25320
gacccaggct ccagctgtgg ctaccacata agggttttta tatgagaaaa ataaaagaat    25380
taagtctgct gaaaaaaaaa aaaaagaaa gaaagaaaga aagaaatgg actcggtatg    25440 tggatgaagc ccaggcacct tcatctgtgt tgcagcacga gtcaccatgc aggatcagtc    25500
taaacgccca tgcacaaatg aatggtacat agccacagtg aagtgtttga ccacaaaaag    25560
gaaagtcagt tgtgataagt gaaacaagcc aggcacagaa agataaatgc tgcatgttat    25620
cattatgtgt aaaggctaaa acgtttatct catacaagta gaaggtaaat acggagacta    25680
```

```
ccagaactta taaagagttc taggaaaaag ctatagagag gctcagggtt gaataactaa    25740
aattatacct aaaataacta aaaggatagc ttacaatatt ctgtagcact gtagaataat    25800
tgtgacagtt tgttgtattt ttctggtttg tgtatgtggg agagaaagta tgtggacaga    25860
ggttgatatc aagtgtctga ctctgcactg cattatttta ggcagggtct ctctctaacc    25920
attgaatgga ctggctaggc agtggtgccc taacatctac ctgtccgtac atctcccaat    25980
actaggttat aagtacactg ggttttaagt acaggctata ggtatagata taggctacag    26040
gtatagatat aggctgctgc aactgattac atgggtgctg ggaacctaac ataggttggg    26100
tcctcatgtt tacacagaaa tcagtactgt gcctactgag tcatttcccc agttctagta    26160
tttgtttttt aaatagctag taattggaat tgtgaatgtt cctaacaaaa gaaaatgata    26220
actatctgag atgctagtta tgatacccctg agtgaatcac actttgtgtg catgtactga    26280
aattcattgt accctgaaaa tacaaaaatt gctctgtgtt gattggctag atgcatgtgt    26340
attagtcagc aatctctaga gtaataaaac ttagatatat gggatgtatt agacttttgg    26400
ccttacaggc caagatccag ctaatccatc agtggcaggc tgtgaacagt aagtctaaga    26460
atccaatagt tgttcagtcc acaaggccgg gtggctcagc tgccttctgt atacagtgga    26520
atcccaaaga aataggcgcc aaagctagtg aggaatggtc ttgctagcaa agcgaaggtg    26580
aaggtaatca ggcagaagac aagaccttcc tttttccgtg tccttatata ggctcctagc    26640
agaacaagtg gcccagacta gatgtggatt aaatgttttg ggtttggttt ggtttgattt    26700
ggtttggttt ggtttggttt ggtttggttt ggtttggttt ggtttggctt ttcgagacag    26760
ggtttctctg tatagccctg gctgtcctgg gttgtagacc aggctggcct caaactcaga    26820
aatctcttgc ctctgcttcc caagtgctgg gattaaaggc gtgcacacca ctacgcccgg    26880
ctcaatagca ttaaatggca tgtctttttcc tatctcaaat gatctggatt aaaagagtgt    26940
cttcctacct caaaggtctg gattagaagt ggatctttct acttcagatt aagttaaact    27000
ctctcacagg tgtgccctct acttttggat ttttggttct agatggagtc aacatgacaa    27060
ccaaaagtaa ctattacaag tccacccaat atcaacttga tacacaatca tatctcctta    27120
tgtcataatt aatttccaaa tgaaaacaat aaccatgtca taaaaacacc taaacatgaa    27180
taactattcc acatcaaatc agaaatgcat tcattatata tttaaccaag tcctaattat    27240
gcctaacgtg atataactat tcttcataca acagcaaaca tgataaattt acaataggtg    27300
gcaatgtctt attctttttaa tatctcaaac ttaaatatga taaccattga tgttatctta    27360
attgatgtta tatcatatga taaagaaatt gatgaaagaa agcacaaatg tctgtataaa    27420
tgctttctta agaaaatagg acagaaactc tgtcaattat aatcatcttt tctgcaacta    27480
gtcatgtggc cttagtattt ataactacct tcctctgcta aaccattttg tattttctcc    27540
acccttggca agaacctcag caggtcttgg ctcttttcct ggaggagtga cccatacctt    27600
cattccttac atgtatgtgc cctttgtcat cctgcctgga ccaggttgtt gtaacattga    27660
ctttaatcac aggacatcgt agcaccaaca catgcccccaa aggatctcct gccctataga    27720
cataaccttt cttacctcca tagtggggag gcagtcccag tcctccttgg tagtctgcat    27780
cagtcacgcc tcctaacact gttattcctt tcttagccgg ttgacttaag ggcatcgaaa    27840
ggccaaagtt gccagaggaa atctgagct tccagttcaa tgaatgtaat gttgttctag    27900
gcaagcagaa ctgaaggtct caggaatagg aagcaaacac ttcccatgga tcactacagg    27960
gtgagagtga gtagaattat tctcttttct accacttgac tcctggacct atggatcctg    28020
```

```
gtatcaaaga aaatgtctca tatattgtac actgattcag agcatgcctt ctggaaaacc   28080
ctgccccagc ccttcatact gctgccatca aattgtcacc tgtgtcttcc tggtaccaac   28140
ttttgtcctg gttagggtta ctattgctgt gaggaaacac catgagcacc aaagcaactt   28200
ggggagaaat gggtttattc agcttatgcg tctacatcac agctcatcat caaaggaagt   28260
cagaacagga gctcaagcag ggcaggaatc tggaggccgt ggaggaaagc tgctgactgg   28320
ctcgctccct aggcttgctc agactgctta tagaactcag gaccaccagc tccagggtgg   28380
ccccaccccg caatggattg ggccctccct caggaatcac aattgcccca cagacttacc   28440
tacagcctag gcattttgga ggctttgagt ctgcctcctc tctgatgatt ctagcttttg   28500
tcaagttgaa gcaaaagtag acaggcctta aactcacaac aacccacctg cctcaatttt   28560
ctgagtgcta atattatatc aatttaaaat ttaaatataa catataaagg gcaatagaaa   28620
ggactagatt catgtaatgg atacaagtta tggaagatgt gtgtgtgtgt gtctgtctgt   28680
ctgtgtgtgt gtttctagtt taattctgtc atgattttt tcttgtaggt ggtaggtgag    28740
tgcatggaat acatttgata ctgaaagggt aaattgaatg tggagcctca cagcttctgt   28800
tccacatgcc tatgataacc gtagaaattc atggattagt atagacgttg agtctggtta   28860
attttggtgt gtgatattta tatatatatg tatatatata tgtgtgtgta tgtatgtatg   28920
tatgtatata tatatatgta tatgtgtata tatatatata tatatatata tatgcaagat   28980
ttcttataat taagtttaca aaattaaaaa ctatcttaaa aattgaattc ttgcaaataa   29040
aaatttagct tttggtgatt ggattcttaa tatggttgat gtttacctag aaagttaaaa   29100
gccctgagtt cagtctccac tttcacccc aaaatgaaaa tcagctttg ggtttcagat     29160
catgagctca gaattaaaga aaacacattt ctaactttgc ttttacaaat cttaatttta   29220
ccaatttcct ttaaagtcac aatgagatac acagtacttc ctagcacccc ttgttcaatt   29280
agataatgtg atttctgaaa gagctccctc tacacagggc acagggcagg tgcaaaactg   29340
tgattgggtg aaatacctgc gagctctcca agcaaagcca ggcctatttg ctttagctgc   29400
cacatcgggt tcttagaccc gacatccctt cccacctgta tcctccctaa ttccttccaa   29460
ccccacaaca ctaggtagga gagaaagaag gttagtggtg gaagtttgca cacatctttt   29520
tagactatttc ctactgatt aggggtgtta ggtccttgag acaagtccag tcttcattgt   29580
caggatatct ccaacttctt cttctcatct ctttgctcac aaagtttatc acaagttgat   29640
aaactacaac aacaggaacc agcagtagca aggacatcag agttgtatag ctttccagaa   29700
aatactttga tatacagtaa ttatcctagc ctttaagagt gaaagatttg gcagcctctg   29760
tgttctacac tcagcataat accttgtata ctgcaggtat ttgctgcatg gtaagtggct   29820
gcccagctac ctagaaagag gtaaatactt ttctattaac atacatattc atttagatat   29880
aggaagaaga taaacaatg gagaaaggca gtcataattt tacagaccag caagtaaacg    29940
cattaacttg gcataggtct ttgtagtctt tttctgcagt gcgtatttcc tgcagtgccc   30000
acaccctaca gttggattgc acgtggcatg ttctgaccca cttttttatgg tatactgtgt   30060
actgtcactg tcaacacaaa tggtagtggc tggattttta tacagtatca gcttgaaggt   30120
tatttctgaa caagccctgt accagattca caggaatatg catctcttat cattactata   30180
ttcttttaac aattgcttct ctcagttggc atgtggtcag tgagttctct cttccttctg   30240
acaggatgca acaggcagtt ttgtcctacc cttccggcaa gttatgtatg ccccgtaccc   30300
caccacgcac attgatgtgg atgtcaacac tgtcaagcag atgccaccgt gtcatgaaca   30360
tatttataat caacgcagat acatgaggtc agagctgaca gccttctgga gggcaacttc   30420
```

```
agaagaggac atggcgcagg acaccatcat ctacacagat gagagcttca ctcctgattt    30480
gtatgtgacg cttggcctta ggtgtcattg ttaaacaaca taaaacttct catttatgag    30540
taaaaacagt gcaagttgta tttaaaagaa aagaaatatg acaagcacat actcaggcac    30600
tttttcttta ttttcttaac tttaaggttt ttttttttt aagatttatt tattattata    30660
tctaagtaca ctgtagctgt cttcagacac accagaagag ggcgtcagat ctcattacaa    30720
atggttgtga gccaccatgt ggttgctggg atttgaactc aggacctttg gaagagcagt    30780
cagtgctctt acctgctgag ccatcttgcc accccaact ttaaatttt tatactatta    30840 tttttagaca gtctcactgg gcctaatgac ttacataggt ggcctggaac tcactatata    30900
gatcaggcta gccttcaact cccagatatc cacctgcctc tgccacccaa atacttggat    30960
taaaggcgtg tgcctccata cctagcctaa atcttcattt cttaaaatac tgttttgcta    31020
agataggtaa agatttcctc ttaaaaataa atacttagca aatatatacc gatctcctaa    31080
ttacttaatg aagggccagc ttaatagtta tcagtcagtt atcagtgcca gcccctactg    31140
ctgggaattt agtgtataac gttcattgta tggtagactg aagtaattct aagtattttt    31200
ttcttgggtg tgactatcaa acacagaaaa gtatttgaaa tttataaaga gaacaggttt    31260
tttctttgca ttttatattt tgctatttat ttcttaccag aagatgcgag cagcaaagta    31320
aaaggcagta agtgctgatg ggtttggagg aacttgggat tttaattata aaacttcaag    31380
aaagcatttc aatggtgttc tagagtctaa aaaagaatag tgagaccca ttcctgttct    31440 ctccgatcaa ccaagagctt gaaatggtgc tagtccttag tatacactga aaagacgcta    31500
agtgtggtca tcccggttgg agggctttag gaagcagtga ccctggacca atgggtgtca    31560
ccgtgtgtct gaagaagaaa gcagagctga acaagaggc gcatggtagg gacaccagca    31620
gccacagtaa actgctgccc agaggtccct gtgtggggct gcagaattaa aagaacccat    31680
tctacacagc tctgctgtgc tctgttagtg ctgagaaagg ttgagaggaa ttgtttcaga    31740
agaggaatcg ttcaaattga actcttatgt cactagttca catactggca atcttggaaa    31800
acatagaaat tttctcactg agtctgcgtg cctgcgtctt cctcgtgact aatatacttg    31860
aagtcctgtt tattttttta gttgattgtt tagaatctct tctcaggaaa tgaggtaaac    31920
ttgaatggat ttgcaccatg ttagtgtttt tgttttgaat atgtttgttt ggaagatttg    31980
aagaaaaagc aattgttcag ctattctggc atgacaaaat catgtcatga attttagaat    32040
tttatttcca gttctaagta aatgttttga atataaaatt gtcagaaata ttttcagcca    32100
caagattata tcttctatta ttgtgggctc atgatagtat cagtgtggtt taaataatat    32160
tcacttttga gtctgggagg tttgaggttt cagattcagg gactcacaca ctgggcaatt    32220
actgtaccac tatgcagttg cttattagta ccacagagta attcccagtt aagttacttt    32280
taattttaac cttttaaga taaaagcagt ctgatgatac attaaagtcg gacatttcct    32340
tgaagatagt ctttcctttt ccagcttttg tgatccagat ctcattcagt aaagcagaaa    32400
ttgggaaata gtggacttaa gttctaaggg acccacaaac cccgtgactg tgctgtccgt    32460
tttcagccag taaccatgaa gtgctggcgt cccttccagc gcccctttct ccatttggtg    32520
cactcatccc tcaaggctga gaggcgtgct gctctcctgt ctatttccct cttccccatg    32580
gttcctgggc agtgatgttg tgatctctac catctgagtc ttgctttgca tttatcttac    32640
tgtgaaaaat gttatatttt ccctctgaca tgaatataat agcctaggga aagacagaag    32700
taaaacactg aagggaatg ggggctgaga aaaaaacagt cattagcttc tgtctggcca    32760
```

```
gcatgctgaa gtgggtcacc tcagttggcc attttgtctg aacgttacat gccagccaac   32820
cttagctgcg gtagtaataa gttatgctgc tggctcatac ttacagatgg taagtctctt   32880
gacctgaggc aaacgtgtaa ggtgacggtt ctaaacacac tgatggacag gcacatgccc   32940
tgcctggata gcctcaaaac acaaacagtg tacaaatgta cccttgcgtt aaagtggatc   33000
tatgtgcgtt tgtgtttatt ttctgtgcat taagtatgta tatgtatgtg tgtttatatt   33060
gtgcacattg agtatatgca tgtgtgttta cactgaatac tgaacccacg gcctcctgca   33120
aactaagtat gcattccaaa tgcacacatc tgtcttctta cacatctgtt tataaaactt   33180
caactttttt actagagcaa gaagttgtgg aatgtaactc tgtaaaaccg tttaatatct   33240
gaaccttttt cttcttagga atattttcca agatgtctta cacagagaca ctctagtgaa   33300
agccttcctg gatcaggtaa atatgatgcc acccattgcc agacaaaaga acatcatata   33360
ttttctttta aaatatgtcc cacagtgcct acagaatata taaaaagcac caaagaatta   33420
aagtgctaga ggccttttcta aagtctgtaa acgattcct ctttgaatta ttaatgggaa   33480
atagcctgta tattaaccgt taaagcagca ttctccatcc tagtggctgc ttcaggtcca   33540
accctctgcc tttagaattt ttgtggttgg tgaagacagg ggtgtgcttt catttgtgtt   33600
aattgaattg aaaatattct taaaacttag gttgcttctg cttaaatggt agcatcctta   33660
ttgtctctgt ttttaaaagt atctgatgag taaacatctg gagatggtac tggattctat   33720
gcgacttgtt tctatacgta agcagagctt tgtcataata gcatgctggg aatcaggcca   33780
agatcctgtg ccatagacat agagttgaga tgaggagaac ctcgtgttca ctgggacttg   33840
tgggtctggg tctgtgtgag gtgaggacag cctgtaatcc caagtctctg aagctgaaaa   33900
gtcccctcct ctactccaca caacctgaag tcattgactt agttatttcc ataataaaat   33960
aaggagatat tttaaggtag aatacaagat ctaagtgcat taaactaggg aatctgaaaa   34020
ggggacagtg ggtttccaga catttgccgc taccagagtc ttgcccttg gaaatcggaa   34080 gaaatggctg taatgggtgt tgtgtgtcag atcctgtcaa caatgtcgcg gaagctgcac   34140
tgtcttgtgt ccctgcaggt cttccatttg aagcctggcc tgtctctcag gagtactttc   34200
cttgcacagt tcctcctcat tcttcacaga aaagccttga cactaatcaa gtacatcgag   34260
gatgatacgt gagtcctgct cctctagagg aaagccttta tgcattgaca gttgctgttc   34320
gttccctttg aacattgtct gtattataat gcggggtttt ttgtctcttt tgttttgttt   34380
ataggcagaa ggggaaaaag ccctttaagt ctcttcggaa cctgaagata gatcttgatt   34440
taacagcaga gggcgatctt aacataataa tggctctagc tgagaaaatt aagccaggcc   34500
tacactcttt catctttggg agacctttct acactagtgt acaagaacgt gatgttctaa   34560
tgaccttttg accgtgtggt ttgctgtgtc tgtctcttca cagtcacacc tgctgttaca   34620
gtgtctcagc agtgtgtggg cacatccttc ctcccgagtc ctgctgcagg acagggtaca   34680
ctacacttgt cagtagaagt ctgtacctga tgtcaggtgc atcgttacag tgaatgactc   34740
ttcctagaat agatgtactc ttttagggcc ttatgtttac aattatccta agtactattg   34800
ctgtctttta aagatatgaa tgatggaata tacacttgac cataactgct gattggtttt   34860
ttgttttgtt ttgtttgttt tcttggaaac ttatgattcc tggtttacat gtaccacact   34920
gaaaccctcg ttagctttac agataaagtg tgagttgact tcctgcccct ctgtgttctg   34980
tggtatgtcc gattacttct gccacagcta acattagag catttaaagt ttgcagttcc   35040
tcagaaagga acttagtctg actacagatt agttcttgag agaagacact gatagggcag   35100
agctgtaggt gaaatcagtt gttagccctt cctttataga cgtagtcctt cagattcggt   35160
```

```
ctgtacagaa atgccgaggg gtcatgcatg ggccctgagt atcgtgacct gtgacaagtt   35220
ttttgttggt ttattgtagt tctgtcaaag aaagtggcat ttgttttat aattgttgcc    35280 aactttaag gttaatttc attatttttg agccgaatta aaatgcgcac ctcctgtgcc     35340
tttcccaatc ttggaaaata taatttcttg cagagggtc agatttcagg gcccagtcac   35400
tttcatctga ccacccttg cacggctgcc gtgtgcctgg cttagattag aagtccttgt   35460
taagtatgtc agagtacatt cgctgataag atctttgaag agcagggaag cgtcttgcct   35520 cttccttg gtttctgcct gtactctggt gtttcccgtg tcacctgcat cataggaaca    35580
gcagagaaat ctgacccagt gctattttc taggtgctac tatggcaaac tcaagtggtc   35640
tgtttctgtt cctgtaacgt tcgactatct cgctagctgt gaagtactga ttagtggagt   35700
tctgtgcaac agcagtgtag gagtatacac aaacacaaat atgtgtttct atttaaaact   35760
gtggacttag cataaaaagg gagaatatat ttattttta caaagggat aaaaatgggc    35820 cccgttcctc acccaccaga tttagcgaga aaaagcttc tattctgaaa ggtcacggtg   35880
gctttggcat tacaaatcag aacaacacac actgaccatg atggcttgtg aactaactgc   35940
aaggcactcc gtcatggtaa gcgagtaggt cccacctcct agtgtgccgc tcattgcttt   36000
acacagtaga atcttatttg agtgctaatt gttgtctttg ctgctttact gtgttgttat   36060
agaaaatgta agctgtacag tgaataagtt attgaagcat gtgtaaacac tgttatatat   36120
cttttctcct agatggggaa ttttgaataa ataccttg aaattctgtg tatgttttag    36180
ttcattattt agggaaaacg ctgctgtgaa aggggcgtg atcagcttcc tattctgcga   36240
cagtcgtgtt gaacggaacc cattggtttt catcttcgct ccccccccct tggtttttcg   36300 agacagggt tctctgtata gccctggctg tcctggacct cactctgtag accaggctgg   36360
cctcgaactc agaaatctac ctgcctctgc ctcccaagtg ctgggaggca gttgccccac   36420
caactagtct tcttttttca aagaagatat ttaaagctaa cgaataatgc tagactctta   36480
catcttaaaa aaaaagaag agaaaagaaa agaaaaggta atcacactgc ccagtgtgta   36540
gtgcatgctt ctacttccgg tccttgggag atggggcag gatgagacgc tccagaccgg    36600
cttccaatac agagttcaag acccactgag ctacgtgagg ctacacgagc ctgccttaa    36660 aaacataaag ctaaagcttt cttcttaact tccagtattg caccttgatt ccccttcaa    36720 atttcacata caaaataatt cttaaattct cttttgaaaa atgttctact gaggccagag   36780
agacagttcg cttggtaaag gtgcctgttg ccaaacgtga taacctgagt taaatcatag   36840
ccccacatgg gggaggaaga aaccccgca gcttgccctc tgatgccatg tatgcactaa   36900
aacacgcacg tgtgtgcgca cacattttt aagttcctat tacattgata gtaatataat   36960
ttaaactgat ttattctccc caagtcattg atacgggtgt ccaacgtaaa atccagcggc   37020
tgaacaaagc acttttaggc gctttaagtt ggaaagcaag aaacggagat tgacactgtc   37080
actccaagag aaaactcttc gtagtagcga gatcggctgt ggagtgaaga tgctcagagg   37140
ctgggaacgc acacagctca ggagtggata gcatccccca gcctcaactc ctaacactgg   37200
gaaagcgtag ggctctcaga tgaggaaaca aaaccataca aagctgctgc aagctaaaca   37260
gaaaaatagt ggcattacac taactgttgt ggaattgtac agaccgattc tcctcccaat   37320
ctgccgagtg tgggcggctt gagagaatga agagagctac tggcctcagg taacagtgct   37380
tcccacagga ctgtctcagg ctgccaccac cataaatagc atttagacg tgacagagct    37440 aaggcttgac acacagccaa aagctactca cattccattt catccccagc tgttctgtca   37500
```

| | |
|---|---:|
| tcgctaagca cagagcattc agcacagctc ttccctgtgg tgggtactca gcactgttga | 37560 |
| gttgaaagga ttgaaaaaac tcaagactat gttctcaaac atttttttaa gctctttta | 37620 |
| aaaccacctt agaatgaaag cttttgactt cttattaaca tgcactaact tcatatacac | 37680 |
| atttagtgtt attgtacagg cacgaagcat actctggtca gaacctgtct cctttggtcc | 37740 |
| accctcccca ccgttttcag cttctattcc accttccata cgtctcaaga tccacatgtg | 37800 |
| agagggaaca ctcagagcct tgtctttctg tatctgggat atctcactta acatgatatt | 37860 |
| ctccagttct gttccatcca tttcattgca aagagcaaga tttcactcta cagccaaata | 37920 |
| acacatttgt ccatgtatat ccgtattttt ccttattcat ctgttgaatg gcacaagact | 37980 |
| gatatcatgg gtaatatcta t | 38001 |

<210> SEQ ID NO 94
<211> LENGTH: 3435
<212> TYPE: DNA
<213> ORGANISM: Rattus norvegicus

<400> SEQUENCE: 94

| | |
|---|---:|
| cgtttgtagt gtcagccatc ccaattgcct gttccttctc tgtgggagtg gtgtctagac | 60 |
| agtccaggca gggtatgcta ggcaggtgcg ttttggttgc ctcagatcgc aacttgactc | 120 |
| cataacggtg accaaagaca aagaaggaa accagattaa aaagaaccgg acacagaccc | 180 |
| ctgcagaatc tggagcggcc gtggttgggg gcggggctac gacggggcgg actcgggggc | 240 |
| gtgggagggc ggggccgggg cggggcccgg agccggctgc ggttgcggtc cctgcgccgg | 300 |
| cggtgaaggc gcagcggcgg cgagtggcta ttgcaagcgt ttggataatg tgagacctgg | 360 |
| gatgcaggga tgtcgactat ctgccccccca ccatctcctg ctgttgccaa gacagagatt | 420 |
| gctttaagtg gtgaatcacc cttgttggcg gctacctttg cttactggga taatattctt | 480 |
| ggtcctagag taaggcacat ttgggctcca agacagacc aagtactcct cagtgatgga | 540 |
| gaaatcactt ttcttgccaa ccacactctg aatgagaaa ttcttcggaa tgcggagagt | 600 |
| ggggcaatag atgtaaagtt ttttgtctta tctgaaaagg gcgtcattat tgtttcatta | 660 |
| atcttcgacg ggaactggaa cggagatcgg agcacttacg gactatcaat tatactgccg | 720 |
| cagacggagc tgagtttcta cctcccactg cacagagtgt gtgttgacag gctaacgcac | 780 |
| atcattcgaa aaggaaggat atggatgcac aaggaaagac aagaaaatgt ccagaaaatt | 840 |
| gtcttggaag gcaccgagag gatggaagat cagggtcaga gtatcatccc tatgcttact | 900 |
| ggggaggtca tccctgtgat ggagctgctt gcgtctatga gatcacacag tgttcctgaa | 960 |
| gacctcgata tagctgatac agtactcaat gatgatgaca ttggtgacag ctgtcatgaa | 1020 |
| ggctttcttc tcaatgccat cagctcacat ctgcagacct gcggctgttc tgtggtggta | 1080 |
| ggcagcagtg cagagaaagt aaataagata gtaagaacac tgtgccttttt tctgacacca | 1140 |
| gcagagagga agtgctccag gctgtgtgaa gccgaatcgt cctttaaata cgaatctgga | 1200 |
| ctctttgtac aaggcttgct aaaggatgcg actggcagtt ttgtactacc tttccggcaa | 1260 |
| gttatgtatg cccccttatcc caccacacac atcgatgtgg atgtcaacac tgtcaagcag | 1320 |
| atgccaccgt gtcatgaaca tatttataat caacgcagat acatgaggtc agagctgaca | 1380 |
| gccttctgga gggcaacttc agaagaggac atggctcagg acaccatcat ctacacagat | 1440 |
| gagagcttca ctcctgattt gaatattttc caagatgtct tacacagaga cactctagtg | 1500 |
| aaagcctttc tggatcaggt cttccatttg aagcctggcc tgtctctcag gagtactttc | 1560 |
| cttgcacagt tcctcctcat tcttcacaga aaagccttga cactaatcaa gtacatagag | 1620 |

```
gatgacacgc agaaggggaa aaagcccttt aagtctcttc ggaacctgaa gatagatctt    1680
gatttaacag cagagggcga ccttaacata ataatggctc tagctgagaa aattaagcca    1740
ggcctacact ctttcatctt cgggagacct ttctacacta gtgtccaaga acgtgatgtt    1800
ctaatgactt tttaaacatg tggtttgctc cgtgtgtctc atgacagtca cacttgctgt    1860
tacagtgtct cagcgctttg gacacatcct tcctccaggg tcctgccgca ggacacgtta    1920
cactacactt gtcagtagag gtctgtacca gatgtcaggt acatcgttgt agtgaatgtc    1980
tcttttccta gactagatgt accctcgtag ggacttatgt ttacaaccct cctaagtact    2040
agtgctgtct tgtaaggata cgaatgaagg gatgtaaact tcaccacaac tgctggttgg    2100
ttttgttgtt tttgtttttt gaaacttata attcatggtt tacatgcatc acactgaaac    2160
cctagttagc tttttacagg taagctgtga gttgactgcc tgtccctgtg ttctctggcc    2220
tgtacgatct gtggcgtgta ggatcacttt tgcaacaact aaaaactaaa gcactttgtt    2280
tgcagttcta cagaaagcaa cttagtctgt ctgcagattc gttttgaaa gaagacatga     2340 gaaagcggag ttttaggtga agtcagttgt tggatcttcc tttatagact tagtccttta    2400
gatgtggtct gtatagacat gcccaaccat catgcatggg cactgaatat cgtgaactgt    2460
ggtatgcttt ttgttggttt attgtacttc tgtcaaagaa agtggcattg gtttttataa    2520
ttgttgccaa gttttaaggt taattttcat tattttgag ccaaattaaa atgtgcacct     2580
cctgtgcctt tcccaatctt ggaaaatata atttcttggc agaaggtcag atttcagggc    2640
ccagtcactt tcgtctgact tccctttgca cagtccgcca tgggcctggc ttagaagttc    2700
ttgtaaacta tgccagagag tacattcgct gataaaatct tctttgcaga gcaggagagc    2760
ttcttgcctc tttcctttca tttctgcctg gactttggtg ttctccacgt tccctgcatc    2820
ctaaggacag caggagaact ctgaccccag tgctatttct ctaggtgcta ttgtggcaaa    2880
ctcaagcggt ccgtctctgt ccctgtaacg ttcgtacctt gctggctgtg aagtactgac    2940
tggtaaagct ccgtgctaca gcagtgtagg gtatacacaa acacaagtaa gtgtttatt    3000 taaaactgtg gacttagcat aaaaagggag actatattta tttttacaa aagggataaa    3060 aatggaaccc tttcctcacc caccagattt agtcagaaaa aaacattcta ttctgaaagg    3120
tcacagtggt tttgacatga cacatcagaa caacgcacac tgtccatgat ggcttatgaa    3180
ctccaagtca ctccatcatg gtaaatgggt agatccctcc ttctagtgtg ccacaccatt    3240
gcttcccaca gtagaatctt atttaagtgc taagtgttgt ctctgctggt ttactctgtt    3300
gttttagaga atgtaagttg tatagtgaat aagttattga agcatgtgta aacactgtta    3360
tacatctttt ctcctagatg gggaatttgg aataaaatac ctttaaaatt caaaaaaaaa    3420 aaaaaaaaa aaaaa                                                      3435
```

COMPOSITIONS FOR MODULATING EXPRESSION OF C9ORF72 ANTISENSE TRANSCRIPT

CROSS-REFERENCE TO RELATED APPLICATIONS

This application is a divisional of U.S. application Ser. No. 15/848,389, filed Dec. 20, 2017, which is a continuation-in-part of U.S. application Ser. No. 15/029,210, filed Apr. 13, 2016, which is a national stage of International Application No. PCT/US2014/60530, filed Oct. 14, 2014, which claims the benefit of priority of U.S. Provisional Application No. 61/890,852, filed Oct. 14, 2013; U.S. application Ser. No. 15/848,389 is also a continuation-in-part of U.S. application Ser. No. 15/029,039, filed Apr. 13, 2016, which is a national stage of International Application No. PCT/US2014/60512, filed Oct. 14, 2014, which claims the benefit of priority of U.S. Provisional Application No. 61/890,849, filed Oct. 14, 2013. Each of the foregoing applications is incorporated by reference herein in its entirety for any purpose.

SEQUENCE LISTING

The present application is being filed along with a Sequence Listing in electronic format. The Sequence Listing is provided as a file entitled BIOL0237USD1SEQ_ST25.txt created Aug. 24, 2019, which is 118 Kb in size. The information in the electronic format of the sequence listing is incorporated herein by reference in its entirety.

FIELD

Provided are compositions and methods for inhibiting expression of C9ORF72 antisense transcript in an animal. Such compositions and methods are useful to treat, prevent, or ameliorate neurodegenerative diseases, including amyotrophic lateral sclerosis (ALS), frontotemporal dementia (FTD), corticalbasal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). This mutation has been found to be the most common genetic cause of ALS and FTD. It is postulated that the ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

There are currently no effective therapies to treat such neurodegenerative diseases. Therefore, it is an object to provide compositions and methods for the treatment of such neurodegenerative diseases.

SUMMARY

Provided herein are compositions and methods for modulating levels of C9ORF72 antisense transcript in cells, tissues, and animals. In certain embodiments, C9ORF72 antisense transcript specific inhibitors modulate expression of C9ORF72 antisense transcript. In certain embodiments, C9ORF72 antisense transcript specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 antisense transcript levels are reduced. In certain embodiments, C9ORF72 antisense transcript associated RAN translation products are reduced. In certain embodiments, the C9ORF72 antisense transcript associated RAN translation products are poly-(proline-alanine), poly-(proline-arginine), and poly-(proline-glycine). In certain embodiments, the C9ORF72 antisense transcript contains a hexanucleotide repeat expansion. In certain embodiments, the hexanucleotide repeat is transcribed in the antisense direction from the C9ORF72 gene. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 24 GGCCCC, CCCCCC, GCCCCC, and/or CGCCCC repeats. In certain embodiments, the hexanucleotide repeat expansion is associated with nuclear foci. In certain embodiments, C9ORF72 antisense transcript associated RAN translation products are associated with nuclear foci. In certain embodiments, the antisense transcript associated RAN translation products are poly-(proline-alanine) and/or poly-(proline-arginine). In certain embodiments, the compositions and methods described herein are useful for reducing C9ORF72 antisense transcript levels, C9ORF72 antisense transcript associated RAN translation products, and nuclear foci. Such reduction can occur in a time-dependent manner or in a dose-dependent manner.

Also provided are methods useful for preventing, treating, ameliorating, and slowing progression of diseases and conditions associated with C9ORF72. In certain embodiments, such diseases and conditions associated with C9ORF72 are neurodegenerative diseases. In certain embodiments, the neurodegenerative disease is amyotrophic lateral sclerosis (ALS), frontotemporal dementia (FTD), corticalbasal degeneration syndrome (CBD), atypical Parkinsonian syndrome, or olivopontocerellar degeneration (OPCD).

Such diseases and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 antisense transcript specific inhibitor to an individual in need thereof. In certain embodiments, the C9ORF72 antisense transcript specific inhibitor is a nucleic acid. In certain embodiments, the nucleic acid is an antisense compound. In certain embodiments, the antisense compound is an antisense oligonucleotide. In certain embodiments, the antisense oligonucleotide is complementary to a C9ORF72 antisense transcript. In certain embodiments, the antisense oligonucleotide is a modified antisense oligonucleotide.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxy-ethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a MOE modified sugar moiety.

"2'-substituted nucleoside" means a nucleoside comprising a substituent at the 2'-position of the furanose ring other than H or OH. In certain embodiments, 2'-substituted nucleosides include nucleosides with bicyclic sugar modifications.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of C9ORF72 antisense trascript", it is implied that the C9ORF72 antisense transcript levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein product encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 antisense transcript" means transcripts produced from the non-coding strand (also antisense strand and template strand) of the C9ORF72 gene. The C9ORF72 antisense transcript differs from the canonically transcribed "C9ORF72 sense transcript", which is produced from the coding strand (also sense strand) of the C9ORF72 gene.

"C9ORF72 antisense transcript associated RAN translation products" means aberrant peptide or di-peptide polymers translated through RAN translation (i.e., repeat-associated, and non-ATG-dependent translation). In certain embodiments, the C9ORF72 antisense transcript associated RAN translation products are any of poly-(proline-alanine), poly-(proline-arginine), and poly-(proline-glycine).

"C9ORF72 antisense transcript specific inhibitor" refers to any agent capable of specifically inhibiting the expression of C9ORF72 antisense transcript and/or its expression products at the molecular level. For example, C9ORF72 specific antisense transcript inhibitors include nucleic acids (including antisense compounds), siRNAs, aptamers, antibodies, peptides, small molecules, and other agents capable of inhibiting the expression of C9ORF72 antisense transcript and/or its expression products, such as C9ORF72 antisense transcript associated RAN translation products.

"C9ORF72 associated disease" means any disease associated with any C9ORF72 nucleic acid or expression product thereof, regardless of which DNA strand the C9ORF72 nucleic acid or expression product thereof is derived from. Such diseases may include a neurodegenerative disease. Such neurodegenerative diseases may include ALS and FTD.

"C9ORF72 foci" means nuclear foci comprising a C9ORF72 transcript. In certain embodiments, a C9ORF72 foci comprises at least one C9ORF72 sense transcript (herein "C9ORF72 sense foci"). In certain embodiments, C9ORF72 sense foci comprise C9ORF72 sense transcripts comprising any of the following hexanucleotide repeats: GGGGCC, GGGGGG, GGGGGC, and/or GGGGCG. In certain embodiments, a C9ORF72 foci comprises at least one C9ORF72 antisense transcript (herein "C9ORF72 antisense foci"). In certain embodiments, C9ORF72 antisense foci comprise C9ORF72 antisense transcripts comprising any of the following hexanucleotide repeats: GGCCCC, CCCCCC, GCCCCC, and/or CGCCCC. In certain embodiments, C9ORF72 foci comprise both C9ORF72 sense transcripts and C9ORF72 antisense transcripts.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise any of the following hexanucleotide repeats: GGGGCC, GGGGGG, GGGGGC, GGGGCG, GGCCCC, CCCCCC, GCCCCC, and/or CGCCCC. In certain embodiments, the hexanucleotide repeat is repeated at least 24 times. Such diseases may include a neurodegenerative disease. Such neurodegenerative diseases may include ALS and FTD.

"C9ORF72 nucleic acid" means any nucleic acid derived from the C9ORF72 locus, regardless of which DNA strand the C9ORF72 nucleic acid is derived from. In certain embodiments, a C9ORF72 nucleic acid includes a DNA sequence encoding C9ORF72, an RNA sequence transcribed from DNA encoding C9ORF72 including genomic DNA comprising introns and exons (i.e., pre-mRNA), and an mRNA sequence encoding C9ORF72. "C9ORF72 mRNA" means an mRNA encoding a C9ORF72 protein. In certain embodiments, a C9ORF72 nucleic acid includes transcripts produced from the coding strand of the C9ORF72 gene. C9ORF72 sense transcripts are examples of C9ORF72 nucleic acids. In certain embodiments, a C9ORF72 nucleic acid includes transcripts produced from the non-coding strand of the C9ORF72 gene. C9ORF72 antisense transcripts are examples of C9ORF72 nucleic acids.

"C9ORF72 pathogenic associated mRNA variant" means the C9ORF72 mRNA variant processed from a C9ORF72 pre-mRNA variant containing the hexanucleotide repeat. A C9ORF72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). In certain embodiments, the level of a C9ORF72 pathogenic associated mRNA variant is measured to determine the level of a C9ORF72 pre-mRNA containing the hexanucleotide repeat in a sample.

"C9ORF72 transcript" means an RNA transcribed from C9ORF72. In certain embodiments, a C9ORF72 transcript is a C9ORF72 sense transcript. In certain embodiments, a C9ORF72 transcript is a C9ORF72 antisense transcript.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information, regardless of which DNA strand the coded information is derived from, is converted into structures present and operating in a cell. Such structures include, but are not limited to the products of transcription and translation, including RAN translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" means a series of six bases (for example, GGGGCC, GGGGGC, GGGGCG, GGCCCC, CCCCCC, GCCCCC, and/or CGCCCC) repeated at least twice. In certain embodiments, the hexanucleotide repeat expansion may be located in intron 1 of a C9ORF72 nucleic acid. In certain embodiments, the hexanucleotide repeat may be transcribed in the antisense direction from the C9ORF72 gene. In certain embodiments, a pathogenic hexanucleotide repeat expansion includes at least 24 repeats of GGGGCC, GGGGGG, GGGGCG, GGCCCC, CCCCCC, GCCCCC, and/or CGCCCC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, GGCCCC, CCCCCC, GCCCCC, and/or CGCCCC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. In certain embodiments, the C9ORF72 associated disease is a C9ORF72 hexanucleotide repeat expansion associated disease. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting expression of a C9ORF72 antisense transcript" means reducing the level or expression of a C9ORF72 antisense transcript and/or its expression products (e.g., RAN translation products). In certain embodiments, C9ORF72 antisense transcripts are inhibited in the presence of an antisense compound targeting a C9ORF72 antisense transcript, including an antisense oligonucleotide targeting a C9ORF72 antisense transcript, as compared to expression of C9ORF72 antisense transcript levels in the absence of a C9ORF72 antisense compound, such as an antisense oligonucleotide.

"Inhibiting expression of a C9ORF72 sense transcript" means reducing the level or expression of a C9ORF72 sense transcript and/or its expression products (e.g., a C9ORF72 mRNA and/or protein). In certain embodiments, C9ORF72 sense transcripts are inhibited in the presence of an antisense compound targeting a C9ORF72 sense transcript, including an antisense oligonucleotide targeting a C9ORF72 sense transcript, as compared to expression of C9ORF72 sense transcript levels in the absence of a C9ORF72 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2' position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

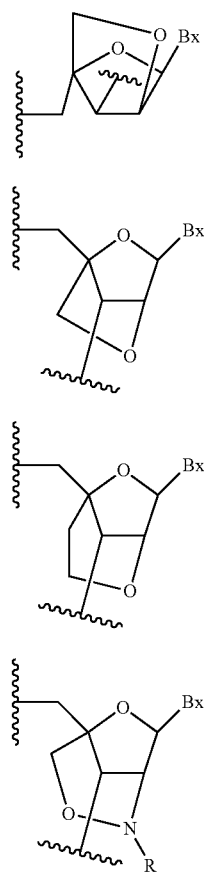

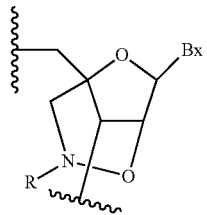

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$— and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-(CH$_2$)$_2$—O-2', 4'-(CH$_2$)$_2$—O-2', 4'—CH$_2$—O—N(R$_1$)-2' and 4'-CH$_2$—N(R$_1$)—O-2'- bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicylic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleoside in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. In certain embodiments, an antisense oligonucleotide targeted to C9ORF72sense transcript is a pharmaceutical agent. In certain embodiments, an antisense oligonucleotide targeted to C9ORF72antisense transcript is a pharmaceutical agent.

"Pharmaceutical composition" means a mixture of substances suitable for administering to as subject. For example, a pharmaceutical composition may comprise an antisense oliognucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form within the body or cells thereof by the action of endogenous enzymes or other chemicals or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" means administering a composition to effect an alteration or improvement of a disease or condition.

"Unmodified nucleobases" means the purine bases adenine (A) and guanine (G), and the pyrimidine bases (T), cytosine (C), and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. (3-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Provided herein are compounds comprising a C9ORF72 antisense transcript specific inhibitor.

In certain embodiments, the C9ORF72 antisense transcript specific inhibitor is a C9ORF72 antisense transcript specific antisense compound.

In certain embodiments, the C9ORF72 antisense transcript specific antisense compound comprises an antisense oligonucleotide.

In certain embodiments, the antisense oligonucleotide consists of 12-30 linked nucleosides.

In certain embodiments, the antisense oligonucleotide consists of 16-25 linked nucleosides.

In certain embodiments, the antisense oligonucleotide consists of 18-22 linked nucleosides In certain embodiments, the antisense oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

In certain embodiments, the antisense oligonucleotide has a nucleobase sequence that is at least 90% complementary to a C9ORF72 antisense transcript.

In certain embodiments, the antisense oligonucleotide has a nucleobase sequence that is at least 95% complementary to a C9ORF72 antisense transcript.

In certain embodiments, the antisense oligonucleotide has a nucleobase sequence that is 100% complementary to a C9ORF72 antisense transcript.

In certain embodiments, the C9ORF72 antisense transcript is SEQ ID NO: 11.

In certain embodiments, the antisense oligonucleotide has a nucleobase sequence comprising at least 8, at least 9, at least 10, at least 11, at least 12, at least 13, at least 14, at least 15, at least 16, at least 17, at least 18, at least 19, or 20 contiguous nucleobases of a sequence selected from among SEQ ID NO: 19-20, 22-26, 28-32, 34-42, 44, 46-55, 58-59, and 61.

In certain embodiments, the antisense oligonucleotide is a modified antisense oligonucleotide.

In certain embodiments, the modified antisense oligonucleotide comprises at least one modified internucleoside linkage.

In certain embodiments, the at least one modified internucleoside linkage is a phosphorothioate internucleoside linkage.

In certain embodiments, each modified internucleoside linkage is a phosphorothioate internucleoside linkage.

In certain embodiments, the modified antisense oligonucleotide comprises at least one phosphodiester internucleoside linkage.

In certain embodiments, the at least one nucleoside of the modified antisense oligonucleotide comprises a modified nucleobase.

In certain embodiments, the modified nucleobase is a 5-methylcytosine.

In certain embodiments, the at least one nucleoside of the modified antisense oligonucleotide comprises a modified sugar.

In certain embodiments, the at least one modified sugar is a bicyclic sugar.

In certain embodiments, the bicyclic sugar comprises a chemical bridge between the 2' and 4' position of the sugar, wherein the chemical bridge is selected from: 4'-CH$_2$—O-2'; 4'-CH(CH$_3$)—O-2'; 4'-(CH$_2$)$_2$—O-2'; and 4'-CH$_2$—N(R)—O-2' wherein R is, independently, H, C$_1$-C$_{12}$ alkyl, or a protecting group.

In certain embodiments, the at least one modified sugar comprises a 2'-O-methoxyethyl group.

In certain embodiments, the antisense oligonucleotide is a gapmer.

In certain embodiments, the C9ORF72 antisense transcript specific antisense compound comprises at least one conjugate.

In certain embodiments, the C9ORF72 antisense transcript specific antisense compound consists of an antisense oligonucleotide.

Provided herein are pharmaceutical compositions comprising any compound described herein and a pharmaceutically acceptable diluent or carrier.

Provided herein are pharmaceutical compositions comprising a C9ORF72 antisense transcript specific inhibitor.

Provided herein are pharmaceutical compositions comprising a C9ORF72 antisense transcript specific inhibitor and a C9ORF sense transcript specific inhibitor.

In certain embodiments, the C9ORF72 sense transcript specific inhibitor is a C9ORF72 sense transcript specific antisense compound.

In certain embodiments, the C9ORF72 antisense transcript specific inhibitor is a C9ORF72 antisense transcript specific antisense compound.

In certain embodiments, the C9ORF72 sense transcript specific antisense compound is an antisense oligonucleotide.

In certain embodiments, the C9ORF72 antisense transcript specific antisense compound is an antisense oligonucleotide.

In certain embodiments, the sense transcript is any of SEQ ID NO: 1-10.

Provided herein are uses of any compound described herein for the manufacture of a medicament for treating a neurodegenerative disease.

Provided herein are methods, comprising contacting a cell with any of SEQ ID NOs: 19-20, 22-26, 28-32, 34-42, 44, 46-55, 58-59, and 61.

Provided herein are methods, comprising contacting a cell with a C9ORF72 antisense transcript specific inhibitor.

Provided herein are methods, comprising contacting a cell with a C9ORF72 antisense transcript specific inhibitor and a C9ORF72 sense transcript specific inhibitor.

Provided herein are methods, comprising contacting a cell with a C9ORF72 antisense transcript specific inhibitor; and thereby reducing the level or expression of C9ORF72 antisense transcript in the cell.

Provided herein are methods, comprising contacting a cell with a C9ORF72 antisense transcript specific inhibitor and a C9ORF72 sense transcript specific inhibitor; and thereby reducing the level or expression of both C9ORF72 antisense transcript and C9ORF72 sense transcript in the cell.

In certain embodiments, the C9ORF72 antisense specific inhibitor is an antisense compound.

In certain embodiments, the C9ORF72 antisense transcript specific inhibitor is an antisense compound.

In certain embodiments, the cell is in vitro.

In certain embodiments, the cell is in an animal.

Provided herein are methods, comprising administering to an animal in need thereof a therapeutically effective amount of a C9ORF72 antisense transcript specific inhibitor.

In certain embodiments the amount is effective to reduce the level or expression of the C9ORF72 antisense transcript.

Provided herein are methods, comprising coadministering to an animal in need thereof a therapeutically effective amount of a C9ORF72 antisense transcript inhibitor and a therapeutically effective amount of a C9ORF72 sense transcript inhibitor.

In certain embodiments the amount is effective to reduce the level or expression of the C9ORF72 antisense transcript and the C9ORF72 sense transcript.

In certain embodiments, wherein the C9ORF72 antisense transcript inhibitor is a C9ORF72 antisense transcript specific antisense compound.

In certain embodiments, the C9ORF72 sense transcript inhibitor is a C9ORF72 sense transcript specific antisense compound.

Provided herein are methods, comprising:
identifying an animal having a C9ORF72 associated disease; and
administering to the animal a therapeutically effective amount of a C9ORF72 antisense transcript specific inhibitor.

In certain embodiments the amount is effective to reduce the level or expression of the C9OR72 antisense transcript.

Provided herein are methods, comprising:
identifying an animal having a C9ORF72 associated disease; and
coadministering to the animal a therapeutically effective amount of a C9ORF72 antisense transcript specific inhibitor and a therapeutically effective amount of a C9ORF72 sense transcript inhibitor.

In certain embodiments the amount is effective to reduce the level or expression of the C9ORF72 antisense transcript and the C9ORF72 sense transcript.

In certain embodiments the C9ORF72 antisense transcript specific inhibitor is a C9ORF72 antisense transcript specific antisense compound.

In certain embodiments the C9ORF72 sense transcript inhibitor is a C9ORF72 sense transcript specific antisense compound.

In certain embodiments the C9ORF72 antisense transcript specific antisense compound is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

In certain embodiments the C9ORF72 sense transcript specific antisense compound is at least 80%, at least 85%, at least 90%, at least 91%, at least 92%, at least 93%, at least 94%, at least 95%, at least 96%, at least 97%, at least 98%, at least 99%, or 100% complementary to a C9ORF72 sense transcript.

In certain embodiments the C9ORF72 antisense transcript is SEQ ID NO: 11.

In certain embodiments the C9ORF72 sense transcript is any of SEQ ID NO: 1-10.

In certain embodiments the C9ORF72 associated disease is a C9ORF72 hexanucleotide repeat expansion associated disease.

In certain embodiments the C9ORF72 associated disease or C9ORF72 hexanucleotide repeat expansion associated disease is amyotrophic lateral sclerosis (ALS), frontotemporal dementia (FTD), corticalbasal degeneration syndrome (CBD), atypical Parkinsonian syndrome, or olivopontocerellar degeneration (OPCD).

In certain embodiments the amyotrophic lateral sclerosis (ALS) is familial ALS or sporadic ALS.

In certain embodiments the contacting or administering reduces C9ORF72 antisense transcript associated RAN translation products.

In certain embodiments the C9ORF72 antisense transcript associated RAN translation products are any of poly-(proline-alanine), poly-(proline-arginine), and poly-(proline-glycine).

In certain embodiments the administering and coadminstering is parenteral administration.

In certain embodiments the parental administration is any of injection or infusion.

In certain embodiments the parenteral administration is any of intrathecal administration or intracerebroventricular administration.

In certain embodiments at least one symptom of a C9ORF72 associated disease or a C9ORF72 hexanucleotide repeat expansion associated disease is slowed, ameliorated, or prevented.

In certain embodiments the at least one symptom is any of motor function, respiration, muscle weakness, fasciculation and cramping of muscles, difficulty in projecting the voice, shortness of breath, difficulty in breathing and swallowing, inappropriate social behavior, lack of empathy, distractibility, changes in food preferences, agitation, blunted emotions, neglect of personal hygiene, repetitive or compulsive behavior, and decreased energy and motivation.

In certain embodiments the C9ORF72 antisense transcript specific antisense compound is an antisense oligonucleotide.

In certain embodiments the C9ORF72 sense transcript specific antisense compound is an antisense oligonucleotide.

In certain embodiments the antisense oligonucleotide is a modified antisense oligonucleotide.

In certain embodiments at least one internucleoside linkage of the antisense oligonucleotide is a modified internucleoside linkage.

In certain embodiments at least one modified internucleoside linkage is a phosphorothioate internucleoside linkage.

In certain embodiments each modified internucleoside linkage is a phosphorothioate internucleoside linkage.

In certain embodiments at least one nucleoside of the modified antisense oligonucleotide comprises a modified nucleobase.

In certain embodiments the modified nucleobase is a 5-methylcytosine.

In certain embodiments at least one nucleoside of the modified antisense oligonucleotide comprises a modified sugar.

In certain embodiments at least one modified sugar is a bicyclic sugar.

In certain embodiments the bicyclic sugar comprises a chemical bridge between the 2' and 4' position of the sugar, wherein the chemical bridge is selected from: 4'-CH2-O-2'; 4'-CH(CH3)-O-2'; 4'-(CH2)2-O-2'; and 4'-CH2-N(R)—O-2' wherein R is, independently, H, C1-C12 alkyl, or a protecting group.

In certain embodiments at least one modified sugar comprises a 2'-O-methoxyethyl group.

In certain embodiments the antisense oligonucleotide is a gapmer.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)$_n$—O-2' bridge, where n=1 or n=2 and 4'-CH$_2$—O—CH$_2$-2'). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH$_2$)$_n$—O-2' bridge, wherein n is 1 or 2; and 4'-CH$_2$—O—CH$_2$-2'. In certain embodiments, the bicyclic sugar is comprises a 4'-CH (CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

Nucleotide sequences that encode the C9ORF72 antisense transcript include, without limitation, the following: SEQ ID NO: 11 is a sequence that is complementary to nucleotides 1159 to 1734 of SEQ ID NO: 2 (the complement of GENBANK Accession No. NT_008413.18 truncated from nucleotides 27535000 to 27565000).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage. In certain embodiments, the antisense compounds targeted to a C9ORF72 nucleic acid comprise at least one phosphodiester linkage and at least one phosphorothioate linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—$C_1$-$C_{10}$ alkyl, OCF$_3$, OCH$_2$F, O(CH$_2$)$_2$SCH$_3$, O(CH$_2$)$_2$—O—N($R_m$)($R_n$), O—CH$_2$—C(=O)—N($R_m$)($R_n$), and O—CH$_2$—C(=O)—N($R_l$)—(CH$_2$)$_2$—N($R_m$)($R_n$), where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, $C_1$-$C_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D- ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-CH$_2$-2', 4'-(CH$_2$)$_2$-2', 4'-(CH$_2$)$_3$-2', 4'—CH$_2$—O-2', 4'-(CH$_2$)$_2$—O-2', 4'—CH$_2$—O—N(R)-2' and 4'-CH$_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

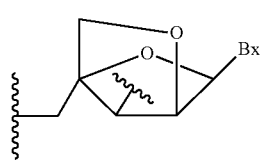

(A)

-continued

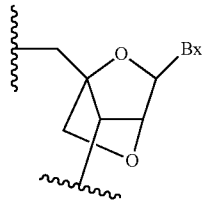

(B)

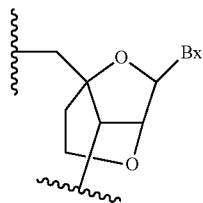

(C)

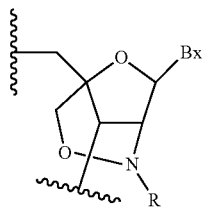

(D)

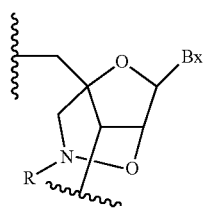

(E)

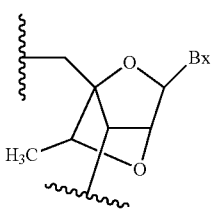

(F)

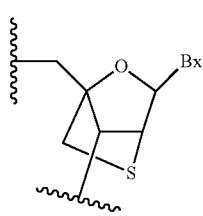

(G)

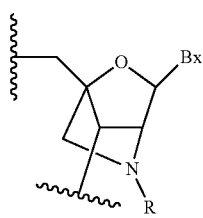

(H)

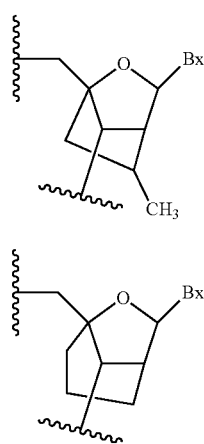

wherein Bx is the base moiety and R is independently H, a protecting group or $C_1$-$C_{12}$ alkyl.

In certain embodiments, bicyclic nucleosides are provided having Formula I:

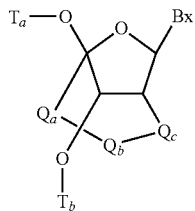

wherein:
Bx is a heterocyclic base moiety;
-$Q_a$-$Q_b$-$Q_c$- is —$CH_2$—$N(R_c)$—$CH_2$—, —$C(=O)$—$N(R_c)$—$CH_2$—, —$CH_2$—$O$—$N(R_c)$—, —$CH_2$—$N(R_c)$—$O$— or —$N(R_c)$—$O$—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

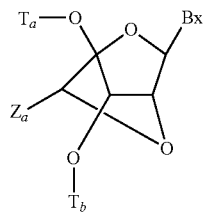

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

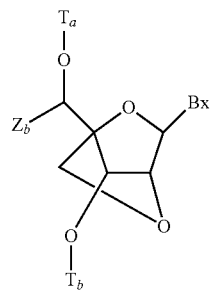

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl ($C(=O)$—).

In certain embodiments, bicyclic nucleosides are provided having Formula IV:

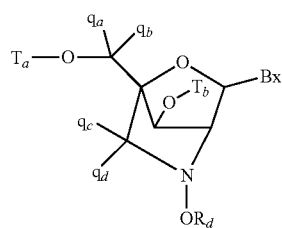

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

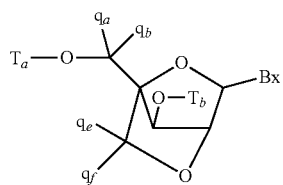

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

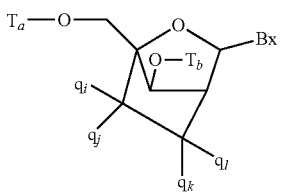

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[($CH_2$)$_n$O]$_m$$CH_3$, O($CH_2$)$_n$$NH_2$, O($CH_2$)$_n$$CH_3$, O($CH_2$)$_n$F, O($CH_2$)$_n$$ONH_2$, $OCH_2$C(=O)N(H)$CH_3$, and O($CH_2$)$_n$ON[($CH_2$)$_n$$CH_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

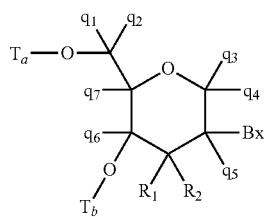

wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH($CH_3$)—O-2') bridging group. In certain embodiments, the (4'-CH($CH_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Strand Specific Semi-Quantitative PCR Analysis of Target RNA Levels

Analysis of specific, low abundance target RNA strand levels may be accomplished by reverse transcription, PCR, and gel densitometry analysis using the Gel Logic 200 Imaging System and Kodak MI software (Kodak Scientific Imaging Systems, Rochester, N.Y., USA) according to manufacturer's instructions.

RT-PCR reactions are carried out as taught in Ladd, P. D., et al, (Human Molecular Genetics, 2007, 16, 3174-3187) and in Sopher, B. L., et al, (Neuron, 2011, 70, 1071-1084) and such methods are well known in the art.

The PCR amplification products are loaded onto gels, stained with ethidium bromide, and subjected to densitometry analysis. Mean intensities from regions of interest (ROI) that correspond to the bands of interest in the gel are measured.

Gene (or RNA) target quantities obtained by PCR are normalized using the expression level of a housekeeping gene whose expression is constant, such as GAPDH. Expression of the housekeeping gene (or RNA) is analyzed and measured using the same methods as the target.

Probes and primers are designed to hybridize to a C9ORF72 nucleic acid. Methods for designing RT-PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid derived from either DNA strand. For example, antisense oligonucleotides described herein may hybridize to a C9ORF72 antisense transcript or a C9ORF72 sense transcript. Antisense oligonucleotides described herein may hybridize to a C9ORF72 nucleic acid in any stage of RNA processing. Described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72 derived from the sense strand. In certain embodiments, the antisense oligonucleotides described herein selectively hybridize to certain variants of C9ORF72 derived from the sense strand. In certain embodiments, the antisense oligonucleotides described herein selectively hybridize to variants of C9ORF72 derived from the sense strand containing a hexanucleotide repeat expansion. In certain embodiments, the antisense oliognucleotides described herein selectively hybridize to pre-mRNA variants containing a hexanucleotide repeat. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG.

In certain embodiments, the antisense oligonucleotides described herein inhibit expression of all variants of C9ORF72 derived from the sense strand. In certain embodiments, the antisense oligonucleotides described herein inhibit expression of all variants of C9ORF72 derived from the sense strand equally. In certain embodiments, the antisense oligonucleotides described herein preferentially inhibit expression of one or more variants of C9ORF72 derived from the sense strand. In certain embodiments, the antisense oligonucleotides described herein preferentially inhibit expression of variants of C9ORF72 derived from the sense strand containing a hexanucleotide repeat expansion. In certain embodiments, the antisense oliognucleotides described herein selectively inhibit expression of pre-mRNA variants containing the hexanucleotide repeat. In certain embodiments, the antisense oliognucleotides described herein selectively inhibit expression of C9ORF72 pathogenic associated mRNA variants. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG. In certain embodiments, the hexanucleotide repeat expansion forms C9ORF72 sense foci. In certain embodiments, antisense oligonucleotides described herein are useful for reducing C9ORF72 sense foci. C9ORF72 sense foci may be reduced in terms of percent of cells with foci as well as number of foci per cell.

C9OFF72 Features

Antisense oligonucleotides described herein may hybridize to any C9ORF72 nucleic acid at any state of processing within any element of the C9ORF72 gene. In certain embodiments, antisense oligonucleotides described herein may target the antisense transcript, e.g., SEQ ID NO: 11. In certain embodiments, antisense oligonucleotides described herein may hybridize to an exon, an intron, the 5' UTR, the 3' UTR, a repeat region, a hexanucleotide repeat expansion, a splice junction, an exon:exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 described below. Antisense oligonucleotides described herein may also target nucleic acids not characterized below and such nucleic acid may be characterized in GENBANK. Moreover, antisense oligonucleotides described herein may also target elements other than exons and such elements as characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
| --- | --- | --- | --- | --- |
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
| --- | --- | --- | --- | --- |
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
| --- | --- | --- | --- | --- |
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
| --- | --- | --- | --- | --- |
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
| --- | --- | --- | --- | --- |
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, administration of an antisense compound targeted to a C9ORF72 antisense transcript results in reduction of C9ORF72 antisense transcript expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 antisense transcript results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values. In certain embodiments, administration of a C9ORF72 antisense compound reduces the number of cells with C9ORF72 antisense foci and/or the number of C9ORF72 antisense foci per cell.

In certain embodiments, administration of an antisense compound targeted to a C9ORF72 sense transcript results in reduction of a C9ORF72 sense transcript expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 sense transcript results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values. In certain embodiments, administration of a C9ORF72 antisense compound reduces the number of cells with C9ORF72 sense foci and/or the number of C9ORF72 sense foci per cell.

In certain embodiments, pharmaceutical compositions comprising an antisense compound targeted to a C9ORF72 nucleic are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 antisense transcript specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Certain Human Therapeutics

The human C9ORF72 antisense transcript specific antisense compounds described herein are being evaluated as possible human therapeutics. Various parameters of potency, efficacy, and/or tolerability are being examined. Such parameters include in vitro inhibition of C9ORF72 antisense transcript; in vitro dose response (IC50); in vivo inhibition of of C9ORF72 antisense transcript in a transgenic animal containing a human C9ORF72 transgene in relevant tissues (e.g., brain and/or spinal cord); and/or tolerability in mouse, rat, dog, and/or primate. Tolerability markers that may be measured include blood and serum chemistry parameters, CSF chemistry parameters, body and organ weights, general observations and/or behavioral tests, and/or biochemical markers such as GFAP and/or AIF1. Acute or long term tolerability may be measured.

Certain Assays for Measuring C9ORF72 Antisense Transcripts

Certain assays described herein are directed to the reduction of C9ORF72 antisense transcript. Additional assays may be used to measure the reduction of C9ORF72 antisense transcript. Additional controls may be used as a baseline for measuring the reduction of C9ORF72 transcript.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of C9ORF72 Antisense Transcript

Antisense oligonucleotides targeted to C9ORF72 antisense transcript were tested for their effects on C9ORF72 antisense transcript expression in vitro. Cultured HepG2 cells were transfected with 50 nM antisense oligonucleotide or water for untransfected controls.

Total RNA was isolated from the cells 24 hours after transfection using TRIzol (Life Technologies) according to the manufacturer's directions. Two DNase reactions were performed, one on the column during RNA purification, and one after purification using amplification grade DNase. The isolated RNA was reverse transcribed to generate cDNA from the C9ORF72 antisense transcript using a primer of the sequence (SEQ ID NO: 12)
CGACTGGAGCACGAGGACACTGAGGAAAGAGAGGTGCGTCAAA.

GAPDH cDNA was reverse transcribed as a control using a primer of the sequence (SEQ ID NO: 13)
TTTTTTTTTTTTTTTTTTTT.

Two PCR amplification steps were completed for the C9ORF72 antisense cDNA. The first PCR amplification was completed using outer forward primer AAAGAGAAGCAACCGGGC (SEQ ID NO: 14) and reverse primer CGACTGGAGCACGAGGACACTG (SEQ ID NO: 15). The PCR product of the first PCR amplification was subjected to a nested PCR using nested forward primer CAGGGACGGCTGACACA (SEQ ID NO: 16) and reverse primer SEQ ID 15. One PCR amplification of GAPDH was performed with forward primer GTCAACGGATTTGGTCGTATTG (SEQ ID NO: 17) and reverse primer TGGAAGATGGTGATGGGATTT (SEQ ID NO:18). The amplified cDNA was then loaded onto 5% acrylamide gels and stained with ethidium bromide. Densitometry analysis was performed using Gel Logic 200 and Kodak MI software (Kodak Scientific Imaging Systems, Rochester, N.Y., USA). The mean intensities from regions of interest (ROI) that corresponded to the C9ORF72 antisense cDNA and GAPDH cDNA bands were measured. The intensity of each C9ORF72 antisense cDNA band was normalized to its corresponding GAPDH cDNA band. These normalized values for the C9ORF72 antisense transcript expression for cells treated with antisense oligonucleotide were then compared to the normalized values for C9ORF72 antisense transcript expression in an untransfected control that was run in the same gel. The final value for band intensities obtained was used to calculate the % inhibition.

The table below lists the antisense oligonucleotides designed and tested for C9ORF72 antisense transcript expression in vitro. ISIS No. 141923 is a negative control that is mismatched to the target. Although ISIS No. 141923 is a negative control in that it is mismatched to the target, it does not necessarily represent a baseline for comparing C9ORF72 ASOs targeting the antisense transcript because it causes reduction of antisense transcript. ISIS No. 576816 is a negative control that is complementary to C9ORF72 sense transcript. ISIS No. 576816 causes no activity and represents a baseline for comparing the ASOs targeting the C9ORF72 antisense transcript. All of the oligonucleotides in the table are 5-10-5 gapmers, 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to a putative antisense transcript sequence (designated herein as SEQ ID NO: 11). SEQ ID NO: 11 is a sequence that is complementary to nucleotides 1159 to 1734 of SEQ ID NO: 2 (the complement of GENBANK Accession No. NT_008413.18 truncated from nucleotides 27535000 to 27565000).

TABLE 6

Inhibition of C9ORF72 Antisense Transcript by Antisense Oligonucleotides

| ISIS NO. | Start Site | Stop Site | Sequence 5' to 3' | % Inhibition | SEQ ID NO |
|---|---|---|---|---|---|
| 141923 | n/a | n/a | CCTTCCCTGAAGGTTCCTCC | 27 | 19 |
| 576816 | n/a | n/a | GCCTTACTCTAGGACCAAGA | 0 | 20 |
| 664634 | 281 | 300 | GGAACTCAGGAGTCGCGCGC | 21 | 22 |
| 664633 | 284 | 303 | TCTGGAACTCAGGAGTCGCG | 14 | 23 |
| 664632 | 293 | 312 | GTAGCAAGCTCTGGAACTCA | 25 | 24 |
| 664631 | 296 | 315 | CCTGTAGCAAGCTCTGGAAC | 40 | 25 |
| 664630 | 299 | 318 | CAGCCTGTAGCAAGCTCTGG | 58 | 26 |
| 664628 | 305 | 324 | CAACCGCAGCCTGTAGCAAG | 51 | 28 |
| 664627 | 308 | 327 | AAACAACCGCAGCCTGTAGC | 24 | 29 |
| 664626 | 311 | 330 | GGGAAACAACCGCAGCCTGT | 35 | 30 |
| 664625 | 314 | 333 | GGAGGGAAACAACCGCAGCC | 22 | 31 |
| 664624 | 317 | 336 | CAAGGAGGGAAACAACCGCA | 14 | 32 |
| 664622 | 341 | 360 | TGATAAAGATTAACCAGAAG | 18 | 34 |
| 664621 | 344 | 363 | ACCTGATAAAGATTAACCAG | 2 | 35 |
| 664620 | 347 | 366 | AAGACCTGATAAAGATTAAC | 14 | 36 |
| 664619 | 353 | 372 | CAAGAAAAGACCTGATAAAG | 34 | 37 |
| 664618 | 356 | 375 | GAACAAGAAAAGACCTGATA | 4 | 38 |
| 664617 | 359 | 378 | GGTGAACAAGAAAGACCTG | 16 | 39 |
| 664616 | 365 | 384 | GCTGAGGGTGAACAAGAAAA | 15 | 40 |
| 664615 | 368 | 387 | CTCGCTGAGGGTGAACAAGA | 37 | 41 |
| 664614 | 371 | 390 | GTACTCGCTGAGGGTGAACA | 31 | 42 |
| 664612 | 377 | 396 | CTCACAGTACTCGCTGAGGG | 11 | 44 |
| 664610 | 383 | 402 | CTTGCTCTCACAGTACTCGC | 79 | 46 |
| 664609 | 386 | 405 | CTACTTGCTCTCACAGTACT | 87 | 47 |
| 664608 | 389 | 408 | CCACTACTTGCTCTCACAGT | 73 | 48 |
| 664607 | 392 | 411 | TCCCCACTACTTGCTCTCAC | 66 | 49 |
| 664606 | 395 | 414 | CTCTCCCCACTACTTGCTCT | 91 | 50 |
| 664605 | 398 | 417 | CCTCTCTCCCCACTACTTGC | 50 | 51 |
| 664604 | 413 | 432 | TTTTGTTTTCCCACCCTCT | 71 | 52 |
| 664603 | 428 | 447 | TTAGGAGGTGTGTGTTTTTG | 66 | 53 |
| 664602 | 431 | 450 | GGTTTAGGAGGTGTGTGTTT | 52 | 54 |
| 664601 | 434 | 453 | GTGGGTTTAGGAGGTGTGTG | 62 | 55 |
| 664598 | 443 | 462 | AGAGCAGGTGTGGGTTTAGG | 34 | 58 |

TABLE 6-continued

Inhibition of C9ORF72 Antisense Transcript by Antisense Oligonucleotides

| ISIS NO. | Start Site | Stop Site | Sequence 5' to 3' | % Inhibition | SEQ ID NO |
|---|---|---|---|---|---|
| 664597 | 446 | 465 | GCAAGAGCAGGTGTGGGTTT | 29 | 59 |
| 664595 | 452 | 471 | GGTCTAGCAAGAGCAGGTGT | 36 | 61 |

Example 2: In Vivo Rodent Inhibition and Tolerability With Treatment of C9ORF72 Antisense Oligonucleotides In order to assess the tolerability of inhibition of C9ORF72 expression in vivo, antisense oligonucleotides targeting a murine C9ORF72 nucleic acid were designed and assessed in mouse and rat models.

ISIS 571883 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are phosphorothioate linkages. All cytosine residues throughout the gapmer are 5-methylcytosines. ISIS 571883 has a target start site of nucleoside 33704 on the murine C9ORF72 genomic sequence, designated herein as SEQ ID NO: 93 (the complement of GENBANK Accession No. NT_166289.1 truncated from nucleosides 3587000 to 3625000).

ISIS 603538 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are either phosphorothioate linkages or phosphate ester linkages (Gs Ao Co Co Gs Cs Ts Ts Gs As Gs Ts Ts Ts Gs Co Co Ao Cs A; wherein 's' denotes a phosphorothioate internucleoside linkage, 'o' denotes a phosphate ester linkage; and A, G, C, T denote the relevant nucleosides). All cytosine residues throughout the gapmer are 5-methylcytosines. ISIS 603538 has a target start site of nucleoside 2872 on the rat C9ORF72 mRNA sequence, designated herein as SEQ ID NO: 94 (GENBANK Accession No. NM_001007702.1).

Mouse Experiment 1

Groups of 4 C57BL/6 mice each were injected with 50 µg, 100 µg, 300 µg, 500 µg, or 700 µg of ISIS 571883 administered via an intracerebroventricular bolus injection. A control group of four C57/BL6 mice were similarly treated with PBS. Animals were anesthetized with 3% isoflourane and placed in a stereotactic frame. After sterilizing the surgical site, each mouse was injected −0.2 mm anterioposterior from the bregma and 3 mm dorsoventral to the bregma with the above-mentioned doses of ISIS 571883 using a Hamilton syringe. The incision was closed with sutures. The mice were allowed to recover for 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely five sections using a mouse brain matrix.

RNA Analysis

RNA was extracted from a 2-3 mm brain section posterior to the injection site, from brain frontal cortex and from the lumbar section of the spinal cord tissue for analysis of C9ORF72 mRNA expression. C9ORF72 mRNA expression was measured by RT-PCR. The data is presented in Table 7. The results indicate that treatment with increasing doses of ISIS 571883 resulted in dose-dependent inhibition of C9ORF72 mRNA expression.

The induction of the microglial marker AIF-1 as a measure of CNS toxicity was also assessed. The data is presented in Table 8. The results indicate that treatment with increasing doses of ISIS 571883 did not result in significant increases in AIF-1 mRNA expression. Hence, the injection of ISIS 571883 was deemed tolerable in this model.

TABLE 7

Percentage inhibition of C9ORF72 mRNA expression compared to the PBS control

| Dose (µg) | Posterior brain | Cortex | Spinal cord |
|---|---|---|---|
| 50 | 22 | 8 | 46 |
| 100 | 22 | 12 | 47 |
| 300 | 55 | 47 | 67 |
| 500 | 61 | 56 | 78 |
| 700 | 65 | 65 | 79 |

TABLE 8

Percentage expression of AIF-1 mRNA expression compared to the PBS control

| Dose (µg) | Posterior brain | Spinal cord |
|---|---|---|
| 50 | 102 | 89 |
| 100 | 105 | 111 |
| 300 | 107 | 98 |
| 500 | 131 | 124 |
| 700 | 122 | 116 |

Mouse Experiment 2

Groups of 4 C57BL/6 mice each were injected with 500 µg of ISIS 571883 administered via an intracerebroventricular bolus injection in a procedure similar to that described above. A control group of four C57/BL6 mice were similarly treated with PBS. The mice were tested at regular time points after ICV administration.

Behavior Analysis

Two standard assays to assess motor behavior were employed; the rotarod assay and grip strength assay. In case of the rotarod assays, the time of latency to fall was measured. The data for the assays is presented in Tables 9 and 10. The results indicate that there were no significant changes in the motor behavior of the mice as a result of antisense inhibition of ISIS 571883 or due to the ICV injection. Hence, antisense inhibition of C9ORF72 was deemed tolerable in this model.

TABLE 9

Latency to fall (sec) in the rotarod assay

| Weeks after injection | PBS | ISIS 571883 |
|---|---|---|
| 0 | 66 | 66 |
| 4 | 91 | 70 |
| 8 | 94 | 84 |

TABLE 10

Mean hindlimb grip strength (g) in the grip strength assay

| Weeks after injection | PBS | ISIS 571883 |
|---|---|---|
| 0 | 57 | 63 |
| 1 | 65 | 51 |
| 2 | 51 | 52 |
| 3 | 51 | 51 |
| 4 | 59 | 72 |
| 5 | 60 | 64 |
| 6 | 61 | 72 |
| 7 | 67 | 68 |
| 8 | 66 | 70 |
| 9 | 63 | 61 |
| 10 | 48 | 46 |

Rat Experiment

Groups of 4 Sprague-Dawley rats each were injected with 700 μg, 1,000 μg, or 3,000 μg of ISIS 603538 administered via an intrathecal bolus injection. A control group of four Sprague-Dawley rats was similarly treated with PBS. Animals were anesthetized with 3% isofluorane and placed in a stereotactic frame. After sterilizing the surgical site, each rat was injected with 30 μL of ASO solution administered via 8 cm intrathecal catheter 2 cm into the spinal canal with a 50 μL flush. The rats were allowed to recover for 4 weeks, after which animals were euthanized according to a humane protocol approved by the Institutional Animal Care and Use Committee.

RNA Analysis

RNA was extracted from a 2-3 mm brain section posterior to the injection site, from brain frontal cortex, and from the cervical and lumbar sections of the spinal cord tissue for analysis of C9ORF72 mRNA expression. C9ORF72 mRNA expression was measured by RT-PCR. The data is presented in Table 11. The results indicate that treatment with increasing doses of ISIS 603538 resulted in dose-dependent inhibition of C9ORF72 mRNA expression.

The induction of the microglial marker AIF-1 as a measure of CNS toxicity was also assessed. The data is presented in Table 12. The results indicate that treatment with increasing doses of ISIS 603538 did not result in significant increases in AIF-1 mRNA expression. Hence, the injection of ISIS 603538 was deemed tolerable in this model.

TABLE 11

Percentage inhibition of C9ORF72 mRNA expression compared to the PBS control

| Dose (μg) | Brain (1 mm section) | Cortex | Spinal cord (lumbar) | Spinal cord (cervical) |
|---|---|---|---|---|
| 700 | 21 | 4 | 86 | 74 |
| 1000 | 53 | 49 | 88 | 82 |
| 3000 | 64 | 62 | 88 | 80 |

TABLE 12

Percentage expression of AIF-1 mRNA expression compared to the PBS control

| Dose (μg) | Brain (1 mm section) | Cortex | Spinal cord (lumbar) | Spinal cord (cervical) |
|---|---|---|---|---|
| 700 | 97 | 119 | 98 | 89 |
| 1000 | 105 | 113 | 122 | 96 |
| 3000 | 109 | 141 | 156 | 115 |

Body Weight Analysis

Body weights of the rats were measured at regular time point intervals. The data is presented in Table 13. The results indicate that treatment with increasing doses of ISIS 603538 did not have any significant changes in the body weights of the rats.

TABLE 13

Body weights of the rats (% initial body weight)

| | Dose (μg) | Week 1 | Week 2 | Week 3 | Week 4 | Week 5 |
|---|---|---|---|---|---|---|
| PBS | | 100 | 94 | 103 | 105 | 109 |
| ISIS 603538 | 700 | 100 | 94 | 98 | 103 | 107 |
| | 1000 | 100 | 95 | 97 | 101 | 103 |
| | 3000 | 100 | 92 | 98 | 102 | 105 |

Example 3: Dose Response Screens of Antisense Oligonucleotides Targeting Human C9ORF72 Sense Transcript in Two Patient Fibroblast Lines Two different fibroblast cell lines from human patients (F09-152 and F09-229) were analyzed with antisense oligonucleotides that target the C9ORF72 sense transcript before exon 1B; i.e. antisense oligonucleotides that target the hexanucleotide repeat expansion containing transcript and antisense oligonucleotides that target downstream of exon 1. The target start and stop sites and the target regions with respect to SEQ ID NOs: 1 and 2 for each oligonucleotide are provided in Table 14. ISIS 577061 and ISIS 577065 target C9ORF72 upstream of exon 1B and just upstream of the hexanucleotide repeat. The rest of the ISIS oligonucleotides of Table 15 target C9ORF72 downstream of exon 1B and the hexanucleotide repeat.

TABLE 14

Target Start and Stop sites of ISIS oligonucleotides used in a dose response assay in C9ORF72 patient fibroblasts

| ISIS No | Target Start Site at SEQ ID NO: 1 | Target Start Site at SEQ ID NO: 2 | Target Region |
|---|---|---|---|
| 577061 | n/a | 1406 | Upstream of exon 1B |
| 577065 | n/a | 1446 | Upstream of exon 1B |
| 577083 | n/a | 3452 | Downstream of exon 1B |
| 576816 | 232 | 7990 | Exon 2 |
| 576974 | 3132 | 28251 | Exon 11 |

Cells were plated at a density of 20,000 cells per well and transfected using electroporation with 246.9 nM, 740.7 nM, 2,222.2 nM, 6,666.7 nM, and 20,000.0 nM concentrations of antisense oligonucleotide. After a treatment period of approximately 16 hours, RNA was isolated from the cells and C9ORF72 mRNA levels were measured by quantitative real-time PCR. Two primer probe sets were used: (1) human C9ORF72 primer probe set RTS3750, which measures total mRNA levels, and (2) RTS3905, which targets the hexanucleotide repeat expansion containing transcript, which measures only mRNA transcripts that contain the hexanucleotide repeat expansion. C9ORF72 mRNA levels were adjusted according to total RNA content, as measured by RIBOGREEN®. Results are presented as percent inhibition of C9ORF72, relative to untreated control cells.

As illustrated in Tables 15-18, below, the two oligonucleotides that target upstream of exon 1B and, therefore, target mRNA transcripts containing the hexanucleotide repeat expansion (ISIS 577061 and ISIS 577065), do not inhibit total mRNA levels of C9ORF72 (as measured by RTS3750) as well as ISIS 576974, 576816, and 577083, which target downstream of exon 1B and, therefore, do not target the mRNA transcript containing the hexanucleotide repeat expansion. Expression levels of the C9ORF72 mRNA transcript containing the hexanucleotide repeat expansion are low (about 10% of the total C9ORF72 expression products), therefore, oligonucleotides targeting the mRNA transcript containing the hexanucleotide repeat expansion do not robustly inhibit total C9ORF72 mRNA (as measured by RTS3905), as suggested by Tables 16 and 18 below. Thus, ISIS 577061 and ISIS 577065 preferentially inhibit expression of mRNA transcripts containing the hexanucleotide repeat expansion.

TABLE 15

Percent inhibition of C9ORF72 total mRNA in F09-152 patient fibroblasts in a dose response assay as measured with RTS3750

| ISIS No | 246.9 nM | 740.7 nM | 2222.2 nM | 6666.7 nM | 20000.0 nM |
|---|---|---|---|---|---|
| 577061 | 6 | 11 | 0 | 18 | 10 |
| 577065 | 10 | 11 | 30 | 29 | 0 |
| 576974 | 61 | 69 | 72 | 83 | 83 |
| 576816 | 35 | 76 | 82 | 91 | 93 |
| 577083 | 28 | 38 | 52 | 75 | 80 |

TABLE 16

Percent inhibition of C9ORF72 mRNA transcripts containing the hexanucleotide repeat expansion in F09-152 patient fibroblasts in a dose response assay as measured with RTS3905

| ISIS No | 246.9 nM | 740.7 nM | 2222.2 nM | 6666.7 nM | 20000.0 nM |
|---|---|---|---|---|---|
| 577061 | 4 | 28 | 58 | 81 | 87 |
| 577065 | 25 | 54 | 70 | 90 | 94 |
| 576974 | 57 | 77 | 81 | 93 | 92 |
| 576816 | 37 | 77 | 91 | 97 | 98 |
| 577083 | 37 | 53 | 74 | 93 | 94 |

TABLE 17

Percent inhibition of C9ORF72 total mRNA in F09-229 patient fibroblasts in a dose response assay as measured with RTS3750

| ISIS No | 246.9 nM | 740.7 nM | 2222.2 nM | 6666.7 nM | 20000.0 nM |
|---|---|---|---|---|---|
| 577061 | 0 | 0 | 0 | 17 | 7 |
| 577065 | 8 | 17 | 17 | 16 | 3 |
| 576974 | 43 | 58 | 85 | 85 | 74 |
| 576816 | 45 | 70 | 85 | 81 | 89 |
| 577083 | 22 | 45 | 56 | 76 | 78 |

TABLE 18

Percent inhibition of C9ORF72 mRNA transcripts containing the hexanucleotide repeat expansion in F09-229 patient fibroblasts in a dose response assay as measured with RTS3905

| ISIS No | 246.9 nM | 740.7 nM | 2222.2 nM | 6666.7 nM | 20000.0 nM |
|---|---|---|---|---|---|
| 577061 | 14 | 36 | 70 | 87 | 89 |
| 577065 | 26 | 48 | 92 | 91 | 98 |
| 576974 | 63 | 87 | 91 | 92 | 91 |
| 576816 | 62 | 81 | 96 | 98 | 100 |
| 577083 | 36 | 64 | 82 | 98 | 96 |

What is claimed is:

1. A compound comprising a modified oligonucleotide consisting of 18 to 50 linked nucleosides wherein the nucleobase sequence of the modified oligonucleotide is at least 90% complementary to an equal length portion of a C9ORF72 antisense transcript, wherein the modified oligonucleotide has a nucleobase sequence comprising at least 18 contiguous nucleobases of a sequence selected from SEQ ID NOs: 47-52, and wherein the modified oligonucleotide comprises at least one modification selected from a modified sugar, a sugar surrogate, and a modified internucleoside linkage.

2. The compound of claim 1, wherein the nucleobase sequence of the modified oligonucleotide is 100% complementary to an equal length portion of a C9ORF72 antisense transcript.

3. The compound of claim 2, wherein the C9ORF72 antisense transcript has the nucleobase sequence of SEQ ID NO: 11.

4. A compound comprising a modified oligonucleotide consisting of 12 to 50 linked nucleosides wherein the nucleobase sequence of the modified oligonucleotide is at least 90% complementary to an equal length portion of a C9ORF72 antisense transcript, wherein the modified oligonucleotide has a nucleobase sequence comprising at least 12 contiguous nucleobases of a sequence selected from SEQ ID NOs: 47 and 50.

5. The compound of claim 1, wherein the modified oligonucleotide is single-stranded.

6. The compound of claim 5, wherein the single-stranded modified oligonucleotide is a gapmer.

7. The compound of claim 1, wherein at least one internucleoside linkage of the modified oligonucleotide is a modified internucleoside linkage.

8. The compound of claim 7, wherein the at least one modified internucleoside linkage is a phosphorothioate internucleoside linkage.

9. The compound of claim 1, wherein at least one nucleobase of the modified oligonucleotide is a modified nucleobase.

10. The compound of claim 9, wherein the modified nucleobase is a 5-methylcytosine.

11. The compound of claim 1, wherein at least one nucleoside of the modified oligonucleotide comprises a modified sugar.

12. The compound of claim 11, wherein each nucleoside of the modified oligonucleotide comprises a modified sugar.

13. The compound of claim 11, wherein at least one modified sugar is a bicyclic sugar.

14. The compound of claim 13, wherein each bicyclic sugar comprises a chemical bridge between the 2' and 4' positions of the sugar, wherein each chemical bridge is independently selected from: 4'-CH(R)—O-2' and 4'-CH$_2$—N—O-2', wherein each R is independently selected from H, $C_1$-$C_{12}$ alkyl, and a protecting group.

15. The compound of claim 14, wherein at least one bicyclic sugar comprises the chemical bridge 4'-CH(R)—O-2' wherein R is methyl.

16. The compound of claim 14, wherein at least one bicyclic sugar comprises the chemical bridge 4'-CH(R)—O-2' wherein R is H.

17. The compound of claim 14, wherein at least one bicyclic sugar comprises the chemical bridge 4'-CH(R)—O-2' wherein R is —CH$_2$—O—CH$_3$.

18. The compound of claim 11, wherein at least one modified sugar comprises a 2'-O-methoxyethyl group or a 2'-O-methyl group.

19. The compound of claim 12, wherein at least one modified sugar comprises a 2'-O-methoxyethyl group or a 2'-O-methyl group.

20. The compound of claim 1, wherein the sugar surrogate is a morpholino or peptide nucleic acid.

21. The compound of claim 1, wherein the compound comprises a conjugate group.

22. The compound of claim 1, consisting of the modified oligonucleotide.

23. A composition comprising the compound of according to claim 1 and a pharmaceutically acceptable carrier or diluent.

24. A double-stranded compound comprising the compound of claim 1.

25. The double-stranded compound of claim 24, wherein the double-stranded compound comprises a conjugate group.

26. A modified oligonucleotide consisting of 18 to 50 linked nucleosides and having a nucleobase sequence comprising at least 18 contiguous nucleobases of a sequence selected from SEQ ID Nos: 47-52, and wherein the modified oligonucleotide comprises at least one modification selected from a modified sugar, a sugar surrogate, and a modified internucleoside linkage.

27. The modified oligonucleotide of claim 26, wherein the modified oligonucleotide is single-stranded.

28. The modified oligonucleotide of claim 27, wherein the single-stranded modified oligonucleotide is a gapmer.

29. The modified oligonucleotide of claim 26, wherein at least one internucleoside linkage of the modified oligonucleotide is a modified internucleoside linkage.

30. The modified oligonucleotide of claim 29, wherein the modified internucleoside linkage is a phosphorothioate internucleoside linkage.

31. The modified oligonucleotide of claim 26, wherein at least one nucleobase of the modified oligonucleotide is a modified nucleobase.

32. The modified oligonucleotide of claim 31, wherein the modified nucleobase is a 5-methylcytosine.

33. The modified oligonucleotide of claim 26, wherein at least one nucleoside of the modified oligonucleotide comprises a modified sugar.

34. The modified oligonucleotide of claim 33, wherein each nucleoside of the modified oligonucleotide comprises a modified sugar.

35. The modified oligonucleotide of claim 33, wherein at least one modified sugar is a bicyclic sugar.

36. The modified oligonucleotide of claim 35, wherein each bicyclic sugar comprises a chemical bridge between the 4' and 2' positions of the sugar, wherein each chemical bridge is independently selected from: 4'-CH(R)—O-2' and 4'-(CH$_2$)$_2$—O-2', wherein each R is independently selected from H, $C_1$-$C_6$ alkyl, and $C_1$-$C_6$ alkoxy.

37. The modified oligonucleotide of claim 36, wherein at least one bicyclic sugar comprises the chemical bridge 4'-CH(R)—O-2' wherein R is methyl.

38. The modified oligonucleotide of claim 36 wherein at least one bicyclic sugar comprises the chemical bridge 4'-CH(R)—O-2' wherein R is H.

39. The modified oligonucleotide of claim 36, wherein at least one bicyclic sugar comprises the chemical bridge 4'-CH(R)—O-2' wherein R is —CH$_2$—O—CH$_3$.

40. The modified oligonucleotide of claim 33, wherein at least one modified sugar comprises a 2'-O-methoxyethyl group or a 2'-O-methyl group.

41. The modified oligonucleotide of claim 34, wherein at least one modified sugar comprises a 2'-O-methoxyethyl group or a 2'-O-methyl group.

42. The modified oligonucleotide of claim 26, wherein at least one nucleoside comprises a sugar surrogate.

43. The modified oligonucleotide of claim 42, wherein the sugar surrogate is a morpholino or a peptide nucleic acid.

44. The modified oligonucleotide of claim 26, wherein the nucleobase sequence of the modified oligonucleotide is at least 90% complementary to an equal length portion of nucleobases 383-453 of SEQ ID NO: 11.

* * * * *